United States Patent
Bouboulis

(10) Patent No.: US 6,974,701 B2
(45) Date of Patent: Dec. 13, 2005

(54) ERYTHROCYTE SEDIMENTATION RATE (ESR) TEST MEASUREMENT INSTRUMENT OF UNITARY DESIGN AND METHOD OF USING THE SAME

(75) Inventor: Denis A. Bouboulis, Darien, CT (US)

(73) Assignee: Hemovations, LLC, Greenwich, CT (US)

( * ) Notice: Subject to any disclaimer, the term of this patent is extended or adjusted under 35 U.S.C. 154(b) by 0 days.

(21) Appl. No.: 10/395,860

(22) Filed: Mar. 21, 2003

(65) Prior Publication Data

US 2004/0185570 A1 Sep. 23, 2004

(51) Int. Cl.$^7$ ............................................. G01N 33/86
(52) U.S. Cl. ............................. 436/70; 436/63; 422/73; 422/99; 422/102
(58) Field of Search ........................... 436/63, 70, 174, 436/180; 422/61, 73, 99, 100, 102, 103, 104, 939–940, 946; 435/2

(56) References Cited

U.S. PATENT DOCUMENTS

| | | |
|---|---|---|
| 3,373,601 A | 3/1968 | Monn |
| 3,660,037 A | 5/1972 | Sokol |
| 3,734,079 A * | 5/1973 | Weber ........................ 600/370 |
| 3,910,103 A | 10/1975 | Rose |
| 3,938,370 A | 2/1976 | Kirsch et al. |
| 3,952,579 A | 4/1976 | Nakajima |
| 4,041,502 A | 8/1977 | Williams et al. |
| 4,118,974 A | 10/1978 | Nozaki et al. |
| 4,187,462 A | 2/1980 | Haker et al. |
| 4,187,719 A | 2/1980 | Brethauer |
| 4,197,735 A | 4/1980 | Munzer et al. |
| 4,200,434 A | 4/1980 | Okochi et al. |
| 4,353,246 A | 10/1982 | Farber |
| 4,392,497 A * | 7/1983 | Ghaussy ...................... 600/370 |
| 4,434,802 A | 3/1984 | Rilliet |
| 4,472,180 A | 9/1984 | Montefiori |
| 4,566,315 A | 1/1986 | O'Brien et al. |
| 4,622,847 A | 11/1986 | Paoletti et al. |
| 4,669,486 A * | 6/1987 | Trell .......................... 600/584 |
| 4,701,305 A | 10/1987 | Hattori et al. |
| 4,774,056 A | 9/1988 | Ricci et al. |
| 4,801,428 A | 1/1989 | Homolko et al. |
| 5,003,488 A | 3/1991 | Hardy |
| 5,019,349 A | 5/1991 | Suzuki |
| 5,065,768 A | 11/1991 | Coleman et al. |
| 5,244,637 A | 9/1993 | Pratellesi et al. |
| 5,316,729 A | 5/1994 | Orth et al. |
| 5,328,822 A | 7/1994 | McKinney et al. |
| 5,487,870 A | 1/1996 | McKinney et al. |
| 5,506,145 A | 4/1996 | Bull et al. |
| 5,558,834 A | 9/1996 | Chu et al. |
| 5,575,977 A | 11/1996 | McKinney et al. |
| 5,594,164 A | 1/1997 | Bull |
| 5,731,513 A | 3/1998 | Bull |
| 5,745,227 A | 4/1998 | Dufresne et al. |
| 5,779,983 A | 7/1998 | Dufresne et al. |
| 5,844,128 A | 12/1998 | Bull |
| 5,914,272 A | 6/1999 | Dufresne et al. |
| 6,098,451 A | 8/2000 | Bull |
| 6,204,066 B1 | 3/2001 | Wardlaw |

FOREIGN PATENT DOCUMENTS

| | | |
|---|---|---|
| EP | 0 044 822 | 1/1982 |
| EP | 0 265 596 | 5/1988 |
| EP | 0 454 593 A1 | 10/1991 |
| FR | 2 566 126 | 12/1985 |
| GB | 2 048 836 A | 12/1980 |
| GB | 2 116 319 A | 9/1983 |
| GB | 2 153 072 A | 8/1985 |
| IT | 72140 | 11/1966 |

OTHER PUBLICATIONS

Web–based publication entitled "Erythrocyte Sedimentation Rate (ESR)" by Gregory C. Gardner, M.D., University of Washington School of Medicine, http://uscme.org/courses, Jul. 1, 1999, pp. 1–4.

Web–based publication entitled "Ask A Doctor" by MDAdvice.com, http://www.mdadvice.com/ask–a–doctor/2/1.html, Sep. 12, 1999, pp. 1–2.

Web–based product brochure for the MICROTEST $1_{EC}$ Electronic Calibration, ALIFAX S.P.A., www.alifax.com, 1 page.

Web–based product brochure for the AnalysInstrument AB Sedimatic 10 by AnalysInstrument AB, www.analysinstrument.com, Apr. 26, 2000, pp. 1–2.

Web–based publication entitled "Erythrocyte Sedimentation Rate Apparatus" by Guest Medical, www.guest–medical.co.uk/HTMLesr.htm, pp. 1–5.

Web–based product brochures for the ESR–10, ESR–100, ESR–8, ESR–Auto Plus, and ESR–Chex, by Streck Laboratories, Inc., www.streck.com, 2001, pp. 1–4.

Web–based product brochures for the Sed–Chek® 2, Sediplast™, and Sedimat® 15, by PolyMedCo, Inc., http://www.polymedco.com/sedcheck_2.html, pp. 1–5.

Web–based product brochures for the SEDI–RATE™ Autozero Westergren ESR System and SEDIGREN™ Autozero Westergren ESR System, by Globe Scientific Inc., www.globescientific.com, 1997, pp. 1–3.

Product brochure for the Sedisure–Rapid Sedimentation Rate Control, by Quantimetrix Corp., Redondo Beach, CA, May 2001, pp. 1–2.

Scientific publication entitled "Reference and Selected Procedure for the Erythrocyte Sedimentation Rate (ESR) Test; Approved Standard—Fourth Edition" by Koepke et al., NCCLS, Wayne, PA, vol. 20, No. 27, 2000, pp. 1–4.

\* cited by examiner

*Primary Examiner*—Maureen M. Wallenhorst
(74) *Attorney, Agent, or Firm*—Thomas J. Perkowski, Esq., P.C.

(57) ABSTRACT

An erythrocyte sedimentation rate (ESR) measurement instrument having a Blood Collection Configuration and an ESR Measurement Configuration. The ESR measurement instrument includes a sedimentation measurement tube having an hollow interior volume containing a predetermined quantity of blood sample diluting agent therewithin and being air/fluid sealed with respect to the ambient environment; and a blood collection tube having a hollow interior volume containing a predetermined quantity of anti-coagulant and being vacuum-sealed with respect to the ambient environment, and physically coupled to the air-sealed sedimentation measurement tube, by at least a portion of the sedimentation measurement tube being inserted within a portion of the hollow interior volume of the blood collection tube. The sedimentation measurement tube and the blood collection tube are maintained stationarily fixed relative to each other as a unitary assembly having a syringe-like form factor when the ESR measurement instrument is arranged in the Blood Collection Configuration. During this configuration, a needle-supporting connector can be connected to the blood collection tube and a sample of whole blood from a patient vacuum-drawn and injected into the blood collection tube. After the sample of anti-coagulated blood has been collected in the blood collection tube and the needle-supporting connector is disconnected therefrom, the air/fluid seal of the sedimentation measurement tube can be broken and then the sedimentation measurement tube can be manually plunged into and to the bottom of the hollow interior volume of said blood collection tube, using a single-handed operation to rearrange the ESR measurement instrument into the ESR Measurement Configuration. The anti-coagulated sample of blood fills up a substantially portion of the sedimentation measurement tube and mixes with the blood sample diluting agent to enable the blood plasma/erythrocyte cell (P/E) interface level within the sedimentation measurement tube to settle downwards toward the blood collection tube during a predetermined time period when said ESR measurement instrument is oriented in a gravity vertical position. By virtue of the present invention, the erythrocyte sedimentation rate (ESR) of the collected blood sample can be measured by determining how far the P/E interface level has moved against graduation markings formed along the length of the sedimentation measurement tube during the predetermined time period.

15 Claims, 59 Drawing Sheets

"Blood Collection Configuration"

A METHOD OF ESR MEASUREMENT (A) INJECTING THE NEEDLE OF BLOOD COLLECTING APPARATUS THROUGH A RUBBER CAP ASSOCIATED WITH A BLOOD COLLECTION TUBE THAT IS VACUUM-SEALED AND CONTAINS A PREDETERMINED QUANTITY OF ANTI-COAGULANT WITHIN THE HOLLOW INTERIOR VOLUME OF SAID BLOOD COLLECTION TUBE AND WHICH IS FURTHER INTEGRATED WITH A SEDIMENTATION MEASUREMENT TUBE THAT IS SEALED AND CONTAINS A PREDETERMINED QUANTITY OF BLOOD DILUTING AGENT WHEREIN A LIQUID SEAL IS DISPOSED BETWEEN THE INTERIOR VOLUME OF SAID BLOOD COLLECTION TUBE AND SAID SEDIMENTATION MEASURING TUBE.

(B) DRAWING A SAMPLE OF WHOLE BLOOD FROM A PATIENT'S BODY AND COLLECTING SAID SAMPLE THROUGH SAID NEEDLE AND INTO SAID BLOOD COLLECTION TUBE, WHEREIN THE COLLECTED SAMPLE OF WHOLE BLOOD MIXES WITH SAID PREDETERMINED QUANTITY OF ANTICOAGULANT WITHIN SAID BLOOD COLLECTION TUBE.

(C) WITHDRAWING SAID NEEDLE FROM SAID BLOOD COLLECTING DEVICE.

(D) BREAKING THE SEAL OF SAID SEDIMENTATION MEASURING DEVICE.

(E) BREAKING THE LIQUID SEAL BETWEEN SAID SEDIMENTATION MEASUREMENT TUBE AND SAID BLOOD COLLECTION TUBE BY HANDLING SAID ESR INSTRUMENT LIKE A SYRINGE-LIKE INSTRUMENT AND MANUALLY PUSHING SAID SEDIMENTATION MEASUREMENT TUBE INTO THE HOLLOW INTERIOR VOLUME OF SAID BLOOD COLLECTION TUBE, THEREBY CAUSING THE SAMPLE OF ANTI-COAGULATED BLOOD TO FILL UP A SUBSTANTIAL PORTION OF SAID SEDIMENTATION MEASUREMENT TUBE, AND MIX WITH SAID PREDETERMINED QUANTITY OF BLOOD DILUTING AGENT, AND WHEREBY THE P/E INTERFACE LEVEL IS PERMITTED TO FLOW DOWN TOWARDS SAID BLOOD COLLECTING TUBE OVER A PREDETERMINED TIME PERIOD WHEN SAID ESR INSTRUMENT IS SUPPORTED IN A GRAVITY VERTICAL DIRECTION DURING SAID PREDETERMINED TIME PERIOD, SO THAT THE ERYTHROCYTE SEDIMENTATION RATE (ESR) OF SAID COLLECTED BLOOD SAMPLE CAN BE MEASURED AGAINST GRADUATION MARKINGS FORMED ALONG THE LENGTH OF SAID SEDIMENTATION MEASURING TUBE.

FIG. 2

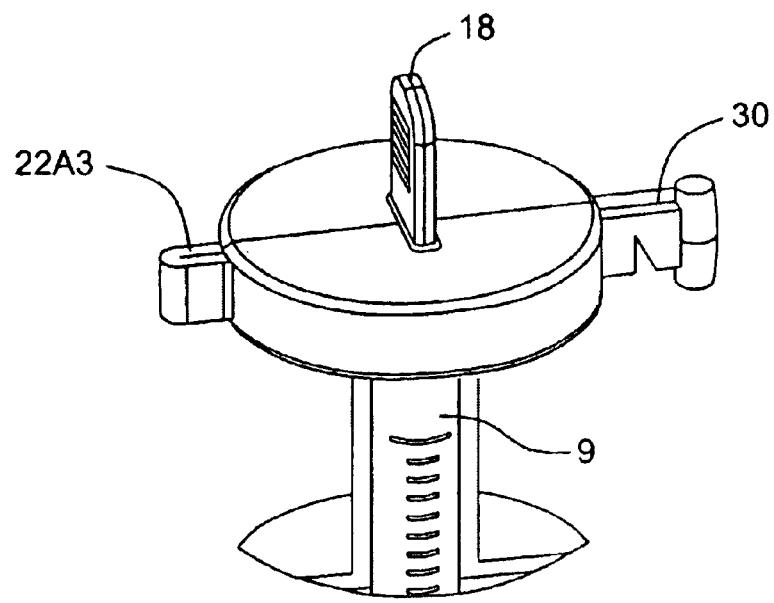
FIG. 4B1
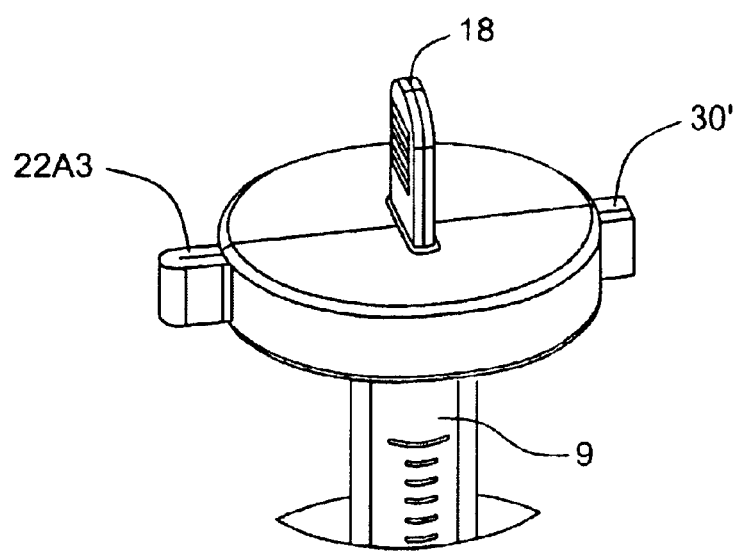
FIG. 4B2

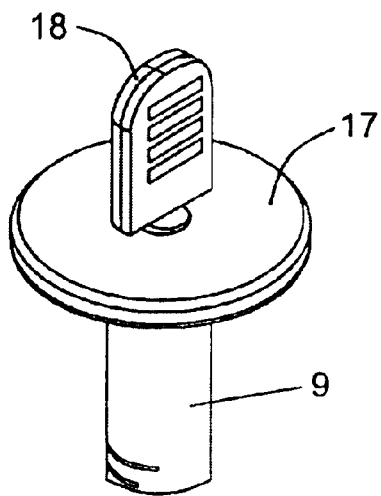
FIG. 5D1
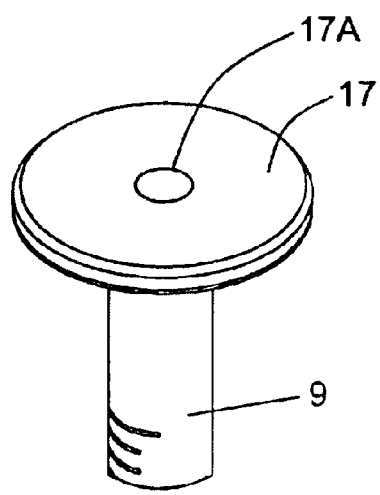
FIG. 5D2

A METHOD OF ESR MEASUREMENT (A) INJECTING THE NEEDLE OF BLOOD COLLECTING APPARATUS THROUGH A RUBBER CAP ASSOCIATED WITH A BLOOD COLLECTION TUBE THAT IS VACUUM-SEALED AND CONTAINS A PREDETERMINED QUANTITY OF ANTI-COAGULANT WITHIN THE HOLLOW INTERIOR VOLUME OF SAID BLOOD COLLECTION TUBE AND WHICH IS FURTHER INTEGRATED WITH A SEDIMENTATION MEASUREMENT TUBE THAT IS SEALED AND CONTAINS A PREDETERMINED QUANTITY OF BLOOD DILUTING AGENT WHEREIN A LIQUID SEAL IS DISPOSED BETWEEN THE INTERIOR VOLUME OF SAID BLOOD COLLECTION TUBE AND SAID SEDIMENTATION MEASURING TUBE.

↓

(B) DRAWING A SAMPLE OF WHOLE BLOOD FROM A PATIENT'S BODY AND COLLECTING SAID SAMPLE THROUGH SAID NEEDLE AND INTO SAID BLOOD COLLECTION TUBE, WHEREIN THE COLLECTED SAMPLE OF WHOLE BLOOD MIXES WITH SAID PREDETERMINED QUANTITY OF ANTICOAGULANT WITHIN SAID BLOOD COLLECTION TUBE.

↓

(C) WITHDRAWING SAID NEEDLE FROM SAID BLOOD COLLECTING DEVICE.

↓

(D) BREAKING THE SEAL OF SAID SEDIMENTATION MEASURING DEVICE.

↓

(E) BREAKING THE LIQUID SEAL BETWEEN SAID SEDIMENTATION MEASUREMENT TUBE AND SAID BLOOD COLLECTION TUBE BY HANDLING SAID ESR INSTRUMENT LIKE A SYRINGE-LIKE INSTRUMENT AND MANUALLY PUSHING SAID SEDIMENTATION MEASUREMENT TUBE INTO THE HOLLOW INTERIOR VOLUME OF SAID BLOOD COLLECTION TUBE, THEREBY CAUSING THE SAMPLE OF ANTI-COAGULATED BLOOD TO FILL UP A SUBSTANTIAL PORTION OF SAID SEDIMENTATION MEASUREMENT TUBE, AND MIX WITH SAID PREDETERMINED QUANTITY OF BLOOD DILUTING AGENT, AND WHEREBY THE P/E INTERFACE LEVEL IS PERMITTED TO FLOW DOWN TOWARDS SAID BLOOD COLLECTING TUBE OVER A PREDETERMINED TIME PERIOD WHEN SAID ESR INSTRUMENT IS SUPPORTED IN A GRAVITY VERTICAL DIRECTION DURING SAID PREDETERMINED TIME PERIOD, SO THAT THE ERYTHROCYTE SEDIMENTATION RATE (ESR) OF SAID COLLECTED BLOOD SAMPLE CAN BE MEASURED AGAINST GRADUATION MARKINGS FORMED ALONG THE LENGTH OF SAID SEDIMENTATION MEASURING TUBE.

FIG. 10

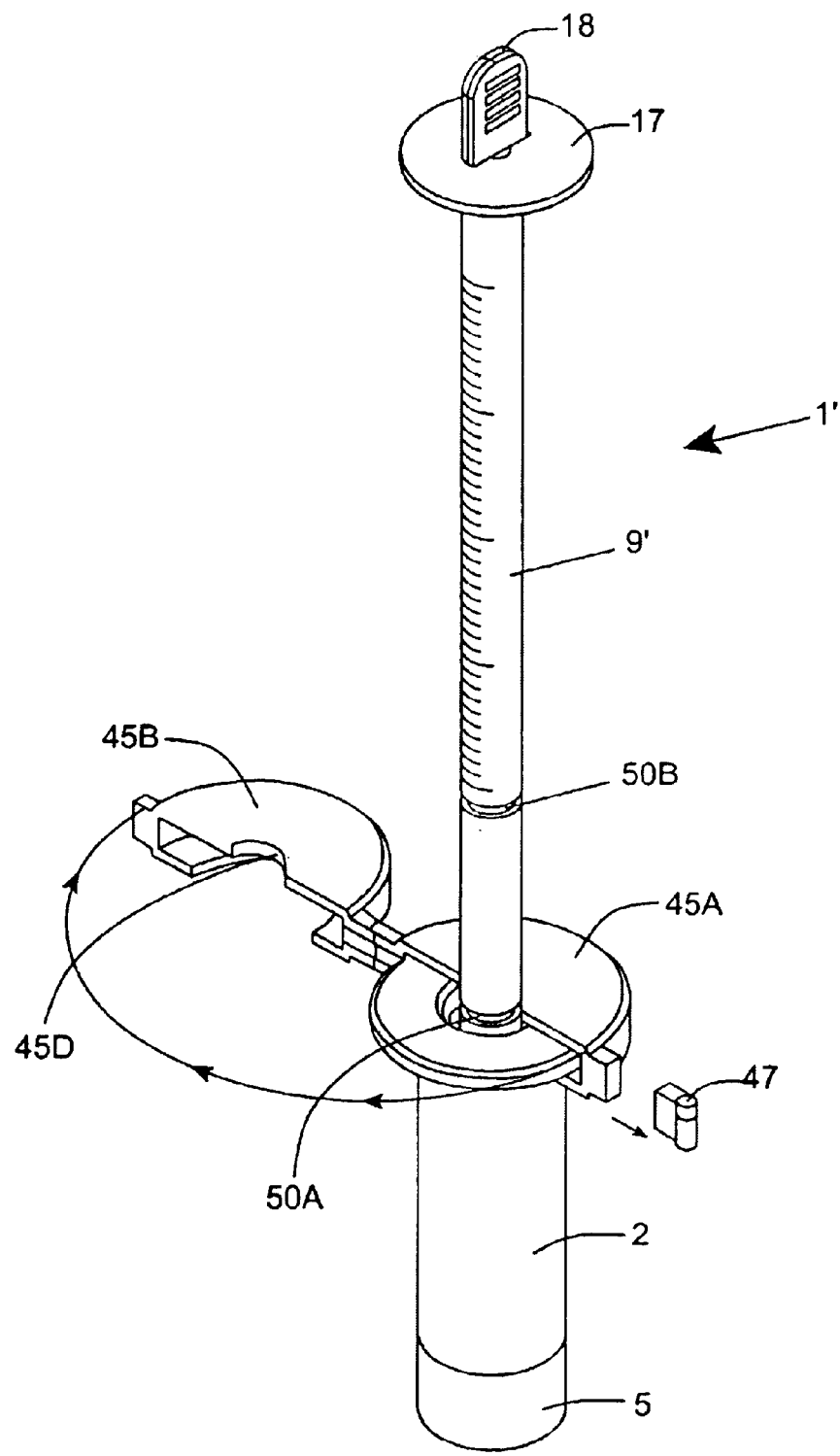
FIG. 12A1

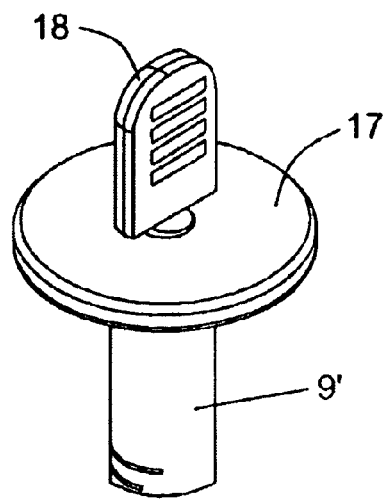
FIG. 12A2
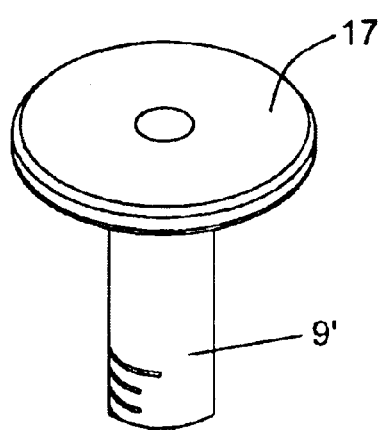
FIG. 12A3

ERYTHROCYTE SEDIMENTATION RATE (ESR) TEST MEASUREMENT INSTRUMENT OF UNITARY DESIGN AND METHOD OF USING THE SAME

BACKGROUND OF INVENTION

1. Field of Invention

The present invention relates to an improved method of, and a disposable test measurement instrument for, determining the Erythrocyte (or red blood cell) Sedimentation Rate (ERS) of a sample of anti-coagulated whole blood, in a safe, effective and inexpensive manner within diverse clinical settings.

2. Brief Description of the State of Knowledge in the Art in the Field of Invention In 1894, Edmund Biernacki (1866–1912), a Polish physician, first noted the increased sedimentation rate of blood from ill individuals and realized that this increase was due to the presence of fibrinogen in the individual's blood sample.

In 1918, Robin Fahraeus (1888–1968) furthered Biernacki's work. His initial motivation to study the ESR of blood was as a pregnancy test, but his interest expanded to the study of the ESR test in disease states of his patients.

In 1921, Alf Westergren (1881–1968) refined the technique of performing the ESR test and reported its usefulness in determining the prognosis of patients with tuberculosis.

In 1935, Maxwell M. Wintrobe (1901–1986) published a variation of the ESR methodology and, at one time, this method was in wide use.

In 1977, the International Committee for Standardization in Hematology (ICSH) recommended the adoption of the Westergren method as the worldwide standard of ESR testing.

In 1997, the NCCLS published the ICSH's most recent recommendations on ESR Testing in the NCCLS Publication No. H2-A4 entitled "Reference and Selected Procedure For The Erythrocyte Sedimentation Rate (ESR) Test; Approved Standard (Fourth Edition), incorporated herein by reference in its entirety.

Also, NCCLS has recently published a number of other important documents setting forth standards and guidelines in relation to ESR testing, namely: No. C28-A2 entitled "How to Define and Determine Reference Intervals in the Clinical Laboratory" which sets forth standard guidelines for determining reference values and reference intervals for quantitative clinical laboratory tests; No. H1-A4 entitled "Evacuated Tubes and Additives for Blood Specimen Collection" which sets forth standard requirements for blood collection tubes and additives including heparin, EDTA, and sodium citrate; No. H3-A4 entitled "Procedures for the Collection of Diagnostic Blood Specimens by Venipuncture" which sets forth standard procedures for the collection of diagnostic specimens by venipuncture, including line draws, blood culture collection, and venipuncture in children, and also includes recommendations on order of draw; No. H7-A3 entitled "Procedure for Determining Packed Cell Volume by the Microhematocrit Method" which sets forth the standard microhematocrit method for determining packed-cell volume, and addresses recommended materials and potential sources of error; No. H18-A2 entitled "Procedures for the Handling and Processing of Blood Specimens" which addresses the multiple factors associated with handling and processing specimens, as well as factors that can introduce imprecision or systematic bias into results; and also No. M29-A entitled "Protection of Laboratory Workers from Instrument Biohazards and Infectious Disease Transmitted by Blood, Body Fluids and Tissue" which sets forth guidance on the risk of transmission of hepatitis viruses and human immunodeficiency viruses in any laboratory setting, specific precautions for preventing the laboratory transmission of blood-borne infection from laboratory instruments and materials, and recommendations for the management of blood-borne exposure. Each of these NCCLS documents helps to indicate the state of knowledge in the art in this field, and is incorporated herein by reference in its entirety.

Today, the Erythrocyte Sedimentation Rate (ESR or Sed Rate) test is one of the most widely performed laboratory tests throughout the world, used to help screen for general illness by determining if a patient has a condition which is causing acute or chronic inflammation, indicated by elevated levels of fibrinogen in the patent's blood. While the ESR test is non-specific, it is still very helpful in following the course of some inflammatory diseases.

The Westergren ESR test method, which is the "Gold Standard" reference method for the ESR test, is performed by placing a diluted sample of anti-coagulated blood in a tall, perfectly vertical tube of 2.5 mm diameter and 200 mm length, and measuring how far in [mm/hr] the blood plasma/erythrocyte cell (P/E) interface level has settled under the influence of gravitational forces after the lapse of sixty (60) minutes (i.e. one hour). The collected whole blood sample is prevented from coagulation by the addition of K3EDTA, and the anti-coagulated blood sample is then diluted by adding four parts of whole anti-coagulated blood to one part dilutent (such as physiologic saline or trisodium citrate at a concentration of between 0.10 to 0.136 mol/litre). The test works because the proteins associated with inflammation, particularly fibrinogen, counteract the zeta potential of red blood cells, which is created by a negative surface charge on the erythrocytes. This negative charge on the erythrocytes serves to repel the individual erythrocytes from each other and thus prolong erythrocyte sedimentation. When systemic inflammation is present, the fibrinogen content of the blood increases, and the erythrocytes tend to aggregate, thereby decreasing their surface-to-mass ratio, and thus increasing their rate of sedimentation.

The Wintrobe ESR test method employs a shorter tube (100 mm) than that used in the Westergren ESR method, and also a different anti-coagulant (i.e. ammonium oxide and potassium oxalate) in smaller amounts so as to not function as a diluting agent. It is generally accepted that the Wintrobe method is more sensitive for mild elevations, but also has a higher false positive rate than the Westergren method. On the other hand the Westergren method is more sensitive for changes at the elevated levels and more useful where the ESR test is being used to evaluate the response to therapy, i.e. in diseases such as temporal arteritis.

Various types of prior art apparatus have been proposed for performing the ESR test using manual principles of operation. The following Patents describe such form of apparatus: U.S. Pat. No. 5,914,272; U.S. Pat. No. 5,779,983; U.S. Pat. No. 5,745,227; U.S. Pat. No. 5,244,637; U.S. Pat. No. 5,065,768; U.S. Pat. No. 4,701,305; U.S. Pat. No. 4,622,847; U.S. Pat. No. 4,434,802; U.S. Pat. No. 4,353,246; U.S. Pat. No. 4,187,719; U.S. Pat. No. 3,938,370; U.S. Pat. No. 3,910,103; U.S. Pat. No. 3,660,037; U.S. Pat. No. 3,373,601; UK Application No. GB 2 116 319 A; and UK Application No. GB 2 048 836 A, each patent being incorporated herein by reference.

However, the ESR test instrumentation disclosed in the above prior art references generally involves the handling of blood in a less than satisfactory manner, creates unnecessary risks to those performing the measurements and to those disposing of the collected blood samples, and requires the lab technician to possess a relatively high degree of skill and dexterity if the test results are to be measured accurately.

Various approaches to automating the ESR test have been attempted, notably using electronic and optical means for tracking the sedimentation of the erythrocytes and providing a result in less than the usual sixty minutes. Such techniques are illustrated in U.S. Pat. Nos. 5,914,272; No. 5,575,977; No. 5,316,729; No. 4,801,428; No. 4,744,056; No. 4,187,462; and No. 4,041,502, each being incorporated herein by reference.

While these prior art methods and apparatus have reduced ESR test times substantially below the standard 60 minute test time period, the results produced by such prior art methods and apparatus do not correlate well with the "reference" Westergren ESR method, and involve the use of expensive equipment.

Thus, there is a great need in the art for an improved method of and apparatus for measuring the rate of erythrocyte sedimentation in a sample of whole blood, while avoiding the shortcomings and drawbacks of prior art apparatus and methodologies.

SUMMARY AND OBJECTS OF INVENTION

Accordingly, it is an object of the present invention to provide an improved method of and apparatus for measuring the Erythrocyte Sedimentation Rate (ESR) in a sample of whole blood, while avoiding the shortcomings and drawbacks of prior art apparatus and methodologies.

It is a further object of the present invention to provide such apparatus in the form of an improved disposable ESR test measurement instrument having a syringe-like form factor, and unitary construction.

It is a further object of the present invention to provide such an ESR measurement instrument having a Blood Collection Configuration and an ESR measurement configuration.

It is another object of the present invention to provide such an ESR measurement instrument, wherein, during its Blood Collection Configuration, an air/fluid sealed sedimentation measurement tube containing a blood diluting agent (i.e. dilutent) is coupled to a vacuum-sealed blood collection tube containing an anti-coagulating agent (i.e. anti-coagulant), so that such sealed tubes are stationarily fixed relative to each other as a unitary assembly. While the ESR measurement instrument is arranged in its Blood Collection Configuration, a Leur® type connector is then connected to the vacuum-sealed blood collection tube and a sample of whole blood from a patient is drawn and injected into the blood collection tube of the ESR measurement instrument.

It is another object of the present invention to provide such an ESR measurement instrument, wherein after the sample of anti-coagulated blood has been collected in the sealed blood collection container and the Leur® type connector is disconnected therefrom, the air-seal of the sedimentation measurement tube is broken and then the sedimentation measurement tube is manually plunged into and to the bottom of the blood collection tube, using a single-handed operation, so as to rearrange the ESR measurement instrument into its ESR Measurement Configuration. This causes the liquid seal between the two tubes to be broken and the anti-coagulated sample of collected blood to mix with the physiologic (0.145 mol/L; 8.5 g/L; "0.85%") NaCl solution contained in the sedimentation measurement tube, thereby filling up a substantial portion thereof with the diluted blood sample and permitting the blood plasma/erythrocyte cell (P/E) interface level of the diluted anti-coagulated blood sample to settle downwards toward the blood collection tube by a measurable distance during a predetermined test time period (e.g. 60 minutes) when the ESR measurement instrument is oriented in a gravity vertical position. Using this ESR measurement instrument, the ESR of the colleted blood sample can be determined by measuring the distance that the P/E interface level travels against graduation markings on the sedimentation measurement tube, during the 60 minute test period.

Another object of the present invention is to provide such an ESR measurement instrument, wherein the blood collection tube has (i) a hollow interior cylindrical volume of a predetermined internal diameter for receiving the sample of whole human blood during blood collection operations, (ii) a pair of low-relief flanges projecting about the outer end surface of the blood collection tube for gripping a rubber needle-pierceable cap with a thick self-sealing end portion and thinner wall portions that snap fit over the low-relief flanges and the outer end portion of the blood collection tube during assembly, and (iii) a large annular flange projecting from the outer end of the blood collection tube at its opposite end, for engagement with the fingers of a person pushing the sedimentation measurement tube within the blood collection tube with his or her thumb.

Another object of the present invention is to provide such an ESR measurement instrument, wherein the sedimentation measurement tube has (i) a hollow central bore of a predetermined diameter and an outer diameter slightly smaller than the internal diameter of the hollow interior volume of the blood collection tube, (ii) a series of graduation marks formed along the exterior surface of the sedimentation measurement tube for indicating the ESR of a whole blood sample in accordance with the ESR measurement method of the present invention, (iii) a plurality of low-relief plunger gripping flanges projecting from the opposite end of the sedimentation measurement tube for retaining a rubber plunger having a hollow interior volume bounded on its closed end by a thin, rupturable wall membrane, and having outer wall surfaces which slide over the free end of the sedimentation measurement tube and engage the flanges projecting therefrom.

Another object of the present invention is to provide such an ESR measurement instrument, wherein the sedimentation measurement tube has a large annular flange projecting from its outer end at the end opposite the rubber plunger, for engagement with the thumb of the person pushing the sedimentation measurement tube within the blood collection tube when rearranging the ESR measurement instrument into its ESR Measurement Configuration.

Another object of the present invention is to provide such an ESR measurement instrument, wherein an air/fluid flow restriction plug is insertable into the top end portion of the sedimentation measurement tube so as to restrict or occlude the flow of blood diluting agent out of the sedimentation measurement tube while the ESR measurement instrument is arranged in its Blood Collection Configuration.

Another object of the present invention is to provide such an ESR measurement instrument, wherein a rubber washer is slidable over the plunger gripping flanges, before the rubber plunger is attached to the end of the sedimentation measurement tube, for creating a liquid seal between outer walls of the sedimentation measurement tube and the inner walls of blood collection tube.

Another object of the present invention is to provide such an ESR measurement tube, wherein a tube holder and restraint assembly, is provided for holding the plunger portion of the sedimentation measurement tube is inserted within the upper portion of the blood collection tube, and maintains these tubes in a stationary position with respect to each other while the small quantity of anti-coagulant (e.g. K3EDTA) is contained within the vacuum-sealed blood collection tube while the ESR measurement instrument is arranged in its Blood Collection Configuration.

Another object of the present invention is to provide a novel method of ESR measurement using an ESR measurement instrument having a unitary construction, with a syringe-like form factor.

Another object of the present invention is to provide such an ESR measurement method, wherein the needle of blood collecting apparatus is injected through a rubber cap associated with a blood collection tube that is vacuum-sealed and contains a predetermined quantity of anti-coagulant within the hollow interior volume of said blood collection tube and which is further integrated with a sedimentation measurement tube that is air/fluid-sealed and contains a predetermined quantity of blood sample diluting agent (e.g. physiologic NaCl solution or sodium citrate solution), wherein a liquid seal is disposed between the interior volume of said blood collection tube and the interior volume of said sedimentation measurement tube.

Another object of the present invention is to provide such an ESR measurement method, wherein a sample of whole blood is drawn from a patient's body under vacuum pressure and the blood sample is collected through the needle and into the blood collection tube, wherein the collected sample of whole blood mixes with the predetermined quantity of anti-coagulant within the blood collection tube.

Another object of the present invention is to provide such an ESR measurement method, wherein the needle is withdrawn from the blood collecting device, and then the air/fluid seal of sedimentation measurement device is broken.

Another object of the present invention is to provide such an ESR measurement method, wherein the liquid seal between the sedimentation measurement tube and the blood collection tube is broken by manually pushing the sedimentation measurement tube into the hollow interior volume of the blood collection tube, thereby causing the sample of anti-coagulated blood to fill up a substantial portion of the sedimentation measurement tube, and mix with the predetermined quantity of blood sample diluting agent (e.g. physiologic NaCl solution or sodium citrate solution), whereby the P/E interface (of the erythrocyte sediment) is permitted to settle down towards the blood collection tube over a predetermined time period when the ESR instrument is supported in a gravity vertical direction during the predetermined time period, so that the erythrocyte sedimentation rate (ESR) of the collected blood sample can be measured by determining the distance that the P/E interface level moved against graduation markings of the sedimentation measurement tube during the predetermined test period.

Yet another object of the present invention is to provide an improved erythrocyte sedimentation rate (ESR) measurement instrument having a syringe-like form factor, wherein an empty sedimentation measurement tube is coupled to a vacuum-sealed blood collection tube containing both an anti-coagulating agent (i.e. anti-coagulant) and a blood diluting agent (i.e. dilutent), so that such sealed tubes are stationarily fixed relative to each other as a unitary assembly during Blood Collection Operations, but are intercoupled into each other and arranged in fluid communication when the ESR measurement instrument is manually configured into its ESR Measurement Configuration. This embodiment of the present invention is most suitable for practicing the Westergren ESR method, wherein blood sample dilution is employed.

Yet another object of the present invention is to provide an improved erythrocyte sedimentation rate (ESR) measurement instrument having a syringe-like form factor, wherein an empty sedimentation measurement tube is coupled to a vacuum-sealed blood collection tube containing only an anti-coagulating agent (i.e. anti-coagulant), so that such sealed tubes are stationarily fixed relative to each other as a unitary assembly during Blood Collection Operations, but are intercoupled into each other and are arranged in fluid communication when the ESR measurement instrument is manually configured into its ESR Measurement Configuration. This embodiment of the present invention is most suitable for practicing the Wintrobe ESR method, wherein blood sample dilution is not employed.

These and other objects of the present invention will become apparent hereinafter and in the Claims to Invention appended hereto.

BRIEF DESCRIPTION OF THE DRAWINGS

FIG. 2 sets forth a flow chart illustrating the steps involved in the method of ESR measurement of the present invention carried out using the ESR measurement instrument of the first illustrative embodiment;

FIG. 4B1 shows the locking seal mechanism provided on the top cover portion of the tube holder and restraint assembly, which surrounds the flange projecting from the top portion of the sedimentation measurement tube;

FIG. 4B2 shows the locking seal mechanism disposed on the top cover portion of the removable tube holder and restraint assembly, broken off so that the top cover portion can be removed from around the flange projecting from the top portion of the sedimentation measurement tube;

FIG. 5D1 is a perspective view of the air/fluid flow restriction plug inserted within the aperture formed in the top flange of sedimentation measurement tube, shown in FIG. 5C;

FIG. 5D2 is a perspective view of the top flange of sedimentation measurement tube, with the air/fluid flow restriction plug removed from the top opening formed therein, shown in FIG. 5C;

FIG. 10 sets forth a flow chart illustrating the steps involved in the method of ESR measurement of the present invention carried out using the ESR measurement instrument of the second illustrative embodiment;

FIG. 12A1 is a perspective view of the disposable ESR measurement instrument of the second illustrative embodiment, shown arranged in its Blood Collection Configuration, and its tube holder/retainer assembly being unlocked from about the sedimentation measurement tube and blood collection tube structures of the instrument (e.g. by breaking its thermosplastic sealing tab);

FIG. 12A2 is a perspective view of the air/fluid flow restriction plug inserted within the aperture formed in the top flange of sedimentation measurement tube;

FIG. 12A3 is a perspective view of the top flange of sedimentation measurement tube, with the air/fluid flow restriction plug removed within the top opening formed therein;

DETAILED DESCRIPTION OF ILLUSTRATIVE EMBODIMENTS OF THE PRESENT INVENTION

Figure 1A:
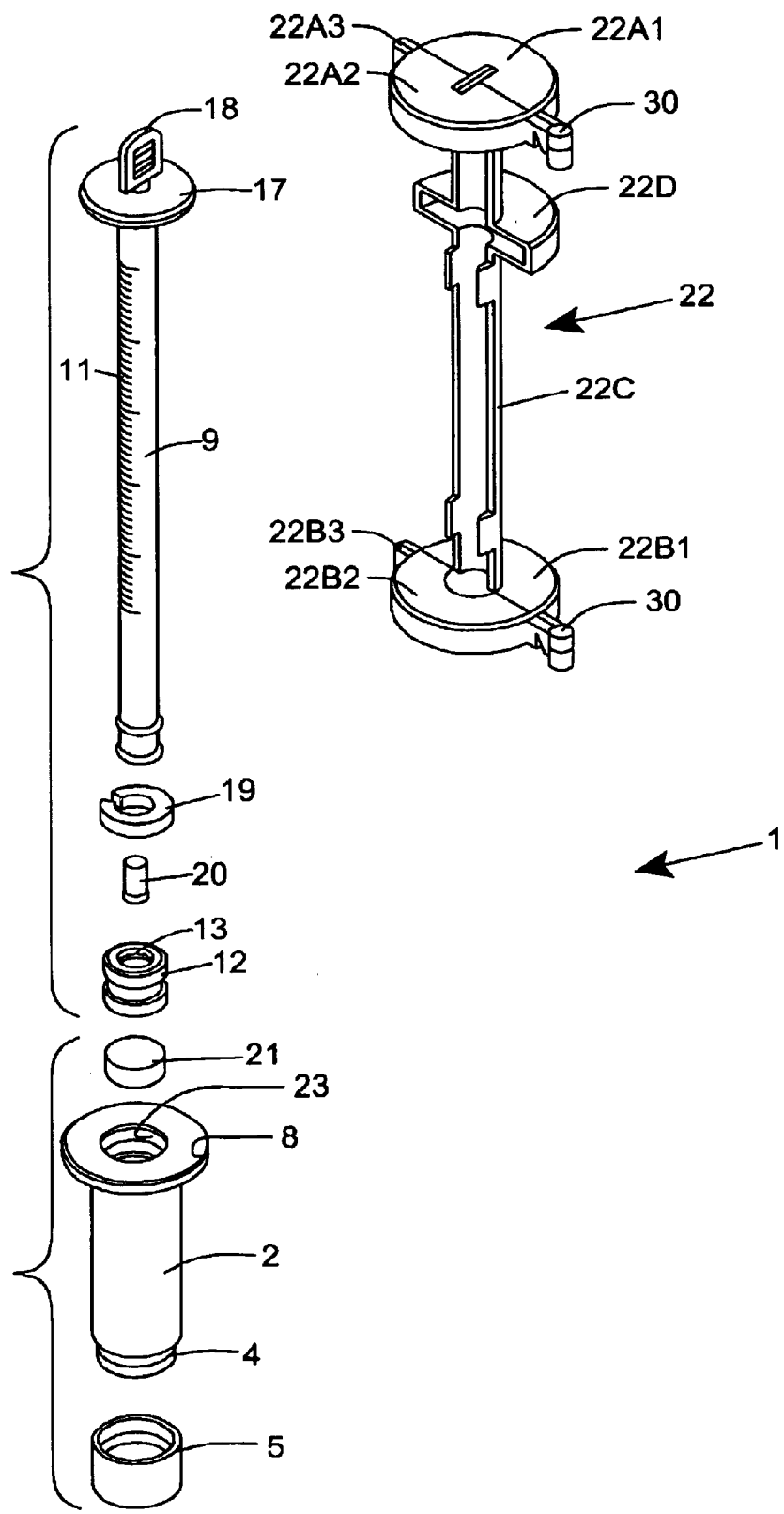
FIG. 1A is an exploded view of the portable and disposable ESR measurement instrument of the present invention, showing that its rubber gasket ring and a rubber plunger element are attached to the end of the sedimentation measurement tube after a small quantity of anti-coagulant (e.g. EDTA or citrate) is injected into the interior volume of the sedimentation measurement tube, and that a rubber cap is attached to the distal end of the blood collection tube and thereafter the blood collection tube is filled with a premeasured quantity of anti-coagulant prior to insertion of the plunger end of an assembled sedimentation measurement tube under a vacuum condition during the assembly of the ESR measurement instrument.

The Detailed Description of the Illustrative Embodiments will now be described in detail with reference to the accompanying Drawings, wherein like structures and elements shown throughout the figures thereof shall be indicated with like reference numerals.

The Detailed Description set forth below discloses a detailed specification of two illustrative embodiments of the ESR measurement instrument of the present invention. In general, these ESR measurement instruments are both portable and disposable in nature, and are designed for quickly performing precise ESR measurements in diverse environments including, for example, doctor offices, laboratories, hospitals, medical clinics, battlefields, and the like.

First Illustrative Embodiment of the ESR Measurement Instrument of the Present Invention As shown in FIGS. 1C through 1F, the ESR measurement instrument of the first illustrative embodiment 1 comprises an assembly of components, namely: a blood collection tube 2 having (i) a hollow interior cylindrical volume 3 of a predetermined internal diameter for receiving a sample of whole human blood during blood collection operations, (ii) a pair of low-relief flanges 4 projecting about the outer end surface of the blood collection tube for gripping a rubber needle-piercable cap 5 with a thick self-sealing end portion 6 and thinner wall portions 7 that snap fit over the low-relief flanges 4 and the outer end portion of the blood collection tube during assembly, and (iii) a large annular flange 8 projecting from the outer end of the blood collection tube at its opposite end, for engagement with the fingers of a person pushing a sedimentation measurement tube 9 within the blood collection tube 2 with his or her thumb; the sedimentation measurement tube 9 having (i) a hollow central bore 10 of a predetermined diameter, (ii) a series of graduation marks 11 formed along the exterior surface thereof for indicating the ESR of a whole blood sample in accordance with the ESR measurement method of the present invention, (iii) a plurality of low-relief plunger gripping flanges 12 projecting from the opposite end of the sedimentation measurement tube for retaining a rubber plunger 13 having a hollow inner volume 14 bounded on its closed end by a thin, rupturable wall membrane 15, and having outer wall surfaces 16 which slide over the free end of the sedimentation measurement tube and engage the flanges 12 projecting therefrom; and (iv) a large annular flange 17 projecting from the outer end of the sedimentation measurement tube at the end opposite the rubber plunger 13, for engagement with the thumb of the person pushing the sedimentation measurement tube 9 within the blood collection tube when rearranging the ESR measurement instrument into its ESR Measurement Configuration, as shown in FIGS. 3A through 6F; an air/fluid flow restriction plug 18 insertable into the top end portion of the sedimentation measurement tube 9 so as to restrict or occlude the flow of air from the ambient environment into the interior of the hollow central bore 10, and blood diluting agent 20 from flowing out of the sedimentation measurement tube, while the ESR measurement instrument is arranged in its Blood Collection Configuration shown in FIGS. 1B through 1F; a rubber washer 19 slidable over the plunger gripping flanges 12, before rubber plunger 13 is attached to the end of the sedimentation measurement tube, for creating a liquid seal between outer walls of the sedimentation measurement tube and the inner walls of blood collection tube; a predetermined quantity of blood diluting agent (e.g. physiologic NaCl solution or sodium citrate solution) 20 inserted within the sedimentation measurement tube 9 after air/fluid flow restriction plug 18 is inserted within central bore 10 but before rubber plunger 13 is snap-fitted over the other end of the sedimentation measurement tube 9; and a predetermined quantity of anti-coagulation agent (e.g. K3EDTA) 21 inserted within the blood collection tube 2 after the rubber needle-pierceable plunger 5 is snap-fitted over the other end of the blood collection tube 2, but before the plunger end of the sedimentation measurement tube assembly is inserted within open end portion of the blood collection tube 2; and a tube holder and restraint assembly 22 for holding the plunger portion 13 of the sedimentation measurement tube within the upper portion of the blood collection tube 2, and maintaining these tubes in a stationary position with respect to each other while the small quantity of anti-coagulant is contained within the vacuum-sealed blood collection tube while the ESR measurement instrument is arranged in its Blood Collection Configuration.

In FIGS. 1B through 1F, the ESR measurement instrument of the present invention is shown arranged in its Blood Collection Configuration. Typically, the instrument would be arranged in this assembled state when packaged and shipped from its manufacturer to the end user (e.g. doctor, hospital, medical clinic, etc.). In this arrangement, the plunger portion 13 of the sedimentation measurement tube 9 is inserted within the upper portion of the blood collection tube 2, and held in a stationary position with respect to the blood collection tube 2 by way of the tube holder and restraint assembly 22. The small quantity of anti-coagulant (e.g. K3EDTA) contained within the vacuum-sealed blood collection tube 2 prevents a sample of whole blood contained therein from coagulation after collection. As illustrated in the cross-sectional view of FIG. 1C, the primary function of the tube holder and restraint assembly 22 is to prevent relative movement between the sedimentation measurement tube and the blood collection tube while the ESR measurement instrument is arranged in its Blood Collection Configuration. As shown, the rubber washer 19 is received within an annular recess 23 formed in the upper portion of the blood collection tube 2, slightly beneath the plane in which annular flange 8 projects from the outer walls of the blood collection tube. The function of the washer 19 is to create an improved liquid seal between the end portion of the sedimentation measurement tube 9 and the walls of the blood collection tube 2.

Figure 1B:
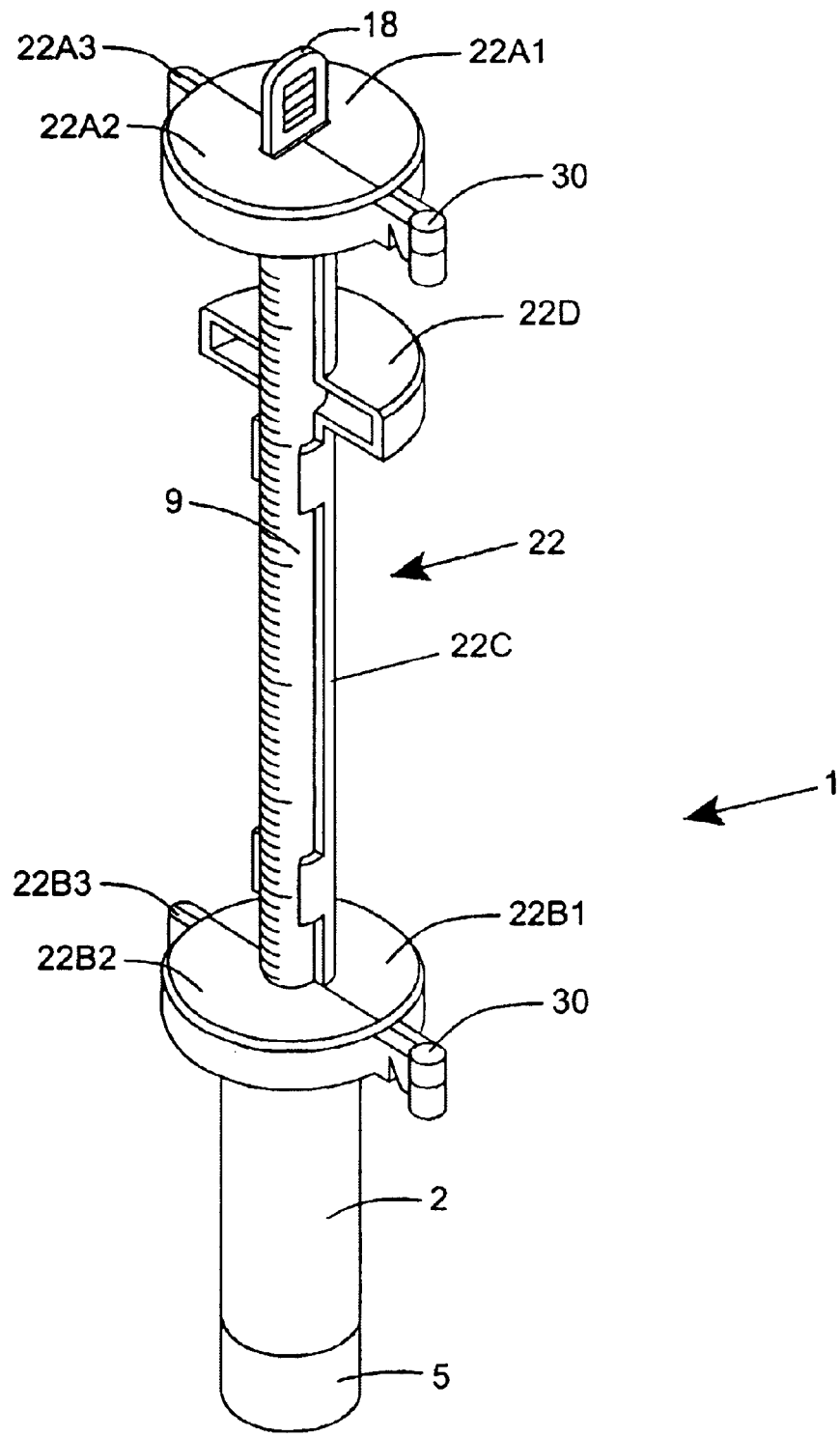
FIG. 1B is a first perspective view of the portable and disposable ESR measurement instrument of the first illustrative embodiment, shown arranged in its Blood Collection Configuration, wherein the plunger portion of the sedimentation measurement tube is inserted within the upper portion of the blood collection tube, and held in a stationary position with respect to the blood collection tube by way of a removable tube holder and restraint assembly, so as to not break the liquid seal created within the pressurized blood collection tube during blood collection operations.
Figure 1C:
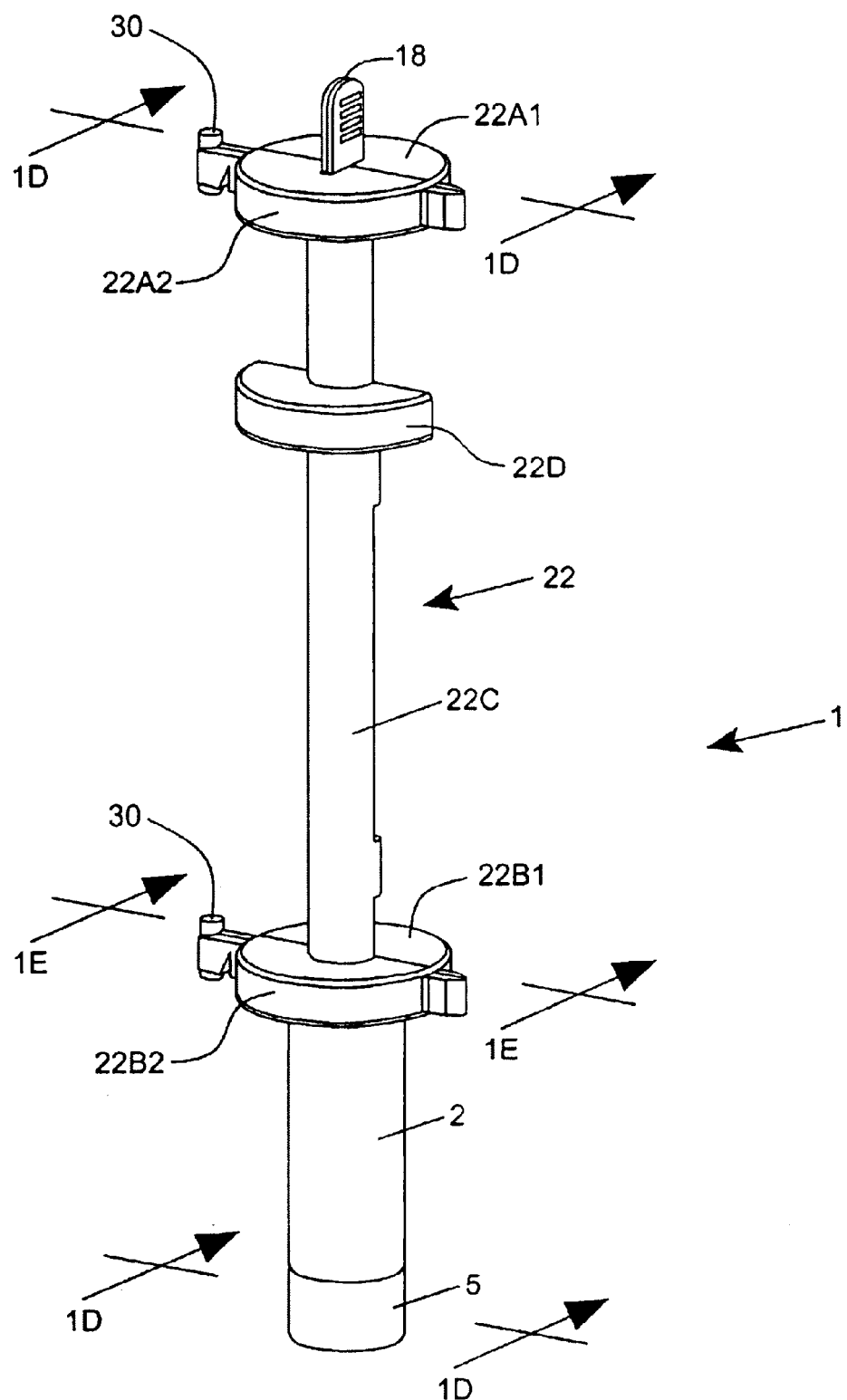
FIG. 1C is a second perspective view of the ESR measurement instrument of the first illustrative embodiment, arranged in its Blood Collection Configuration, as shown in FIG. 1B, wherein the air/fluid flow restriction plug inserted into the top opening of the sedimentation measurement tube is permitted to extend through an aperture formed within the top cover portion of the sedimentation measurement tube holder/restraint assembly, which surrounds the flange projecting from the top portion of the sedimentation measurement tube.
Figure 1D:
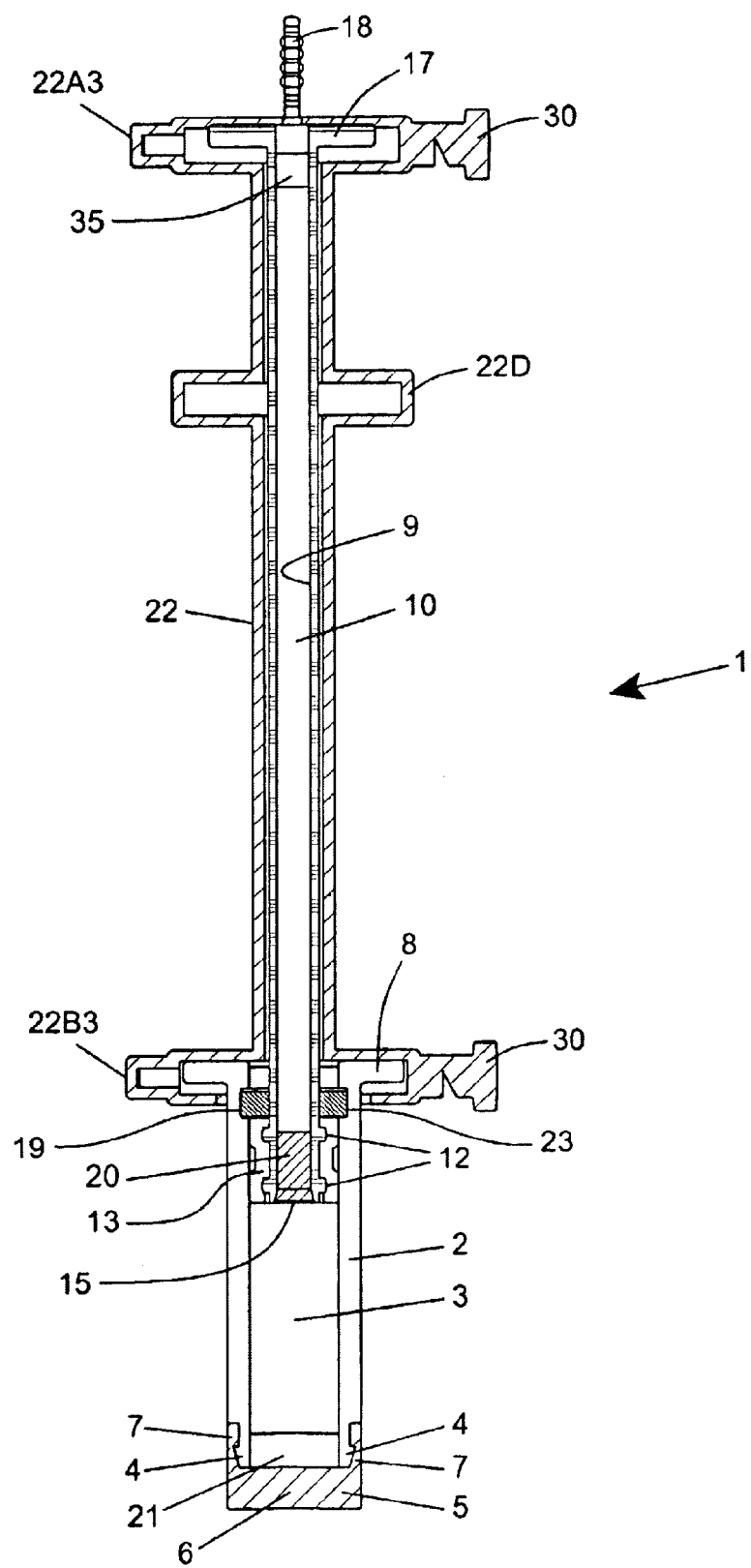
FIG. 1D is a cross-sectional view of the ESR measurement instrument of the first illustrative embodiment taken along line 1D—1D of FIG. 1C, wherein the plunger portion of the sedimentation measurement tube is inserted within the upper portion of the blood collection tube and held in a stationary position with respect to the pressurized blood collection tube by way of the tube holder and restraint assembly, and wherein the air/fluid flow restriction plug inserted into the top opening of the sedimentation measurement tube is permitted to extend through an aperture formed within the top cover portion of the tube holder and restraint assembly, while the top cover portion surrounds the flange projecting from the top portion of the sedimentation measurement tube and the lower cover portion surrounds the flange projecting from the top portion of the blood collection tube, so as to not break the liquid seal created within the blood collection tube while the ESR measurement instrument is arranged in its Blood Collection Configuration.
Figure 1E:
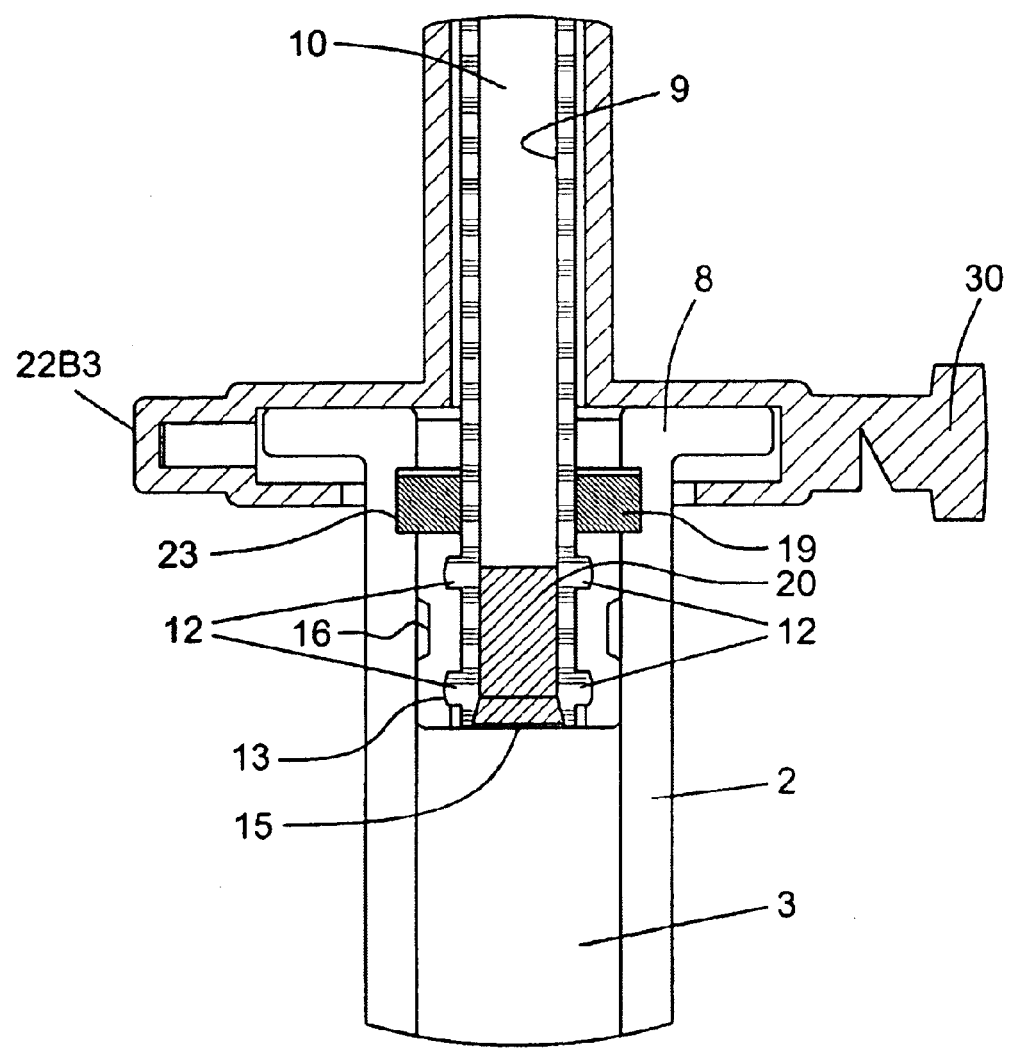
FIG. 1E is a cross-sectional enlarged view of the portion of the ESR measurement instrument of the first illustrative embodiment taken along line 1E—1E of FIG. 1B, showing in greater detail that the plunger portion of the sedimentation measurement tube comprises a rubber plunger element affixed to the free end of the hollow sedimentation measurement tube, and rubber frangible membrane covering the end opening thereof at the distal end of rubber plunger, so as to retain a premeasured quantity of blood sample diluting agent (e.g. physiologic NaCl solution or trisodium citrate solution) within the sedimentation measurement tube while the ESR measurement instrument is arranged in its Blood Collection Configuration.
Figure 1F:
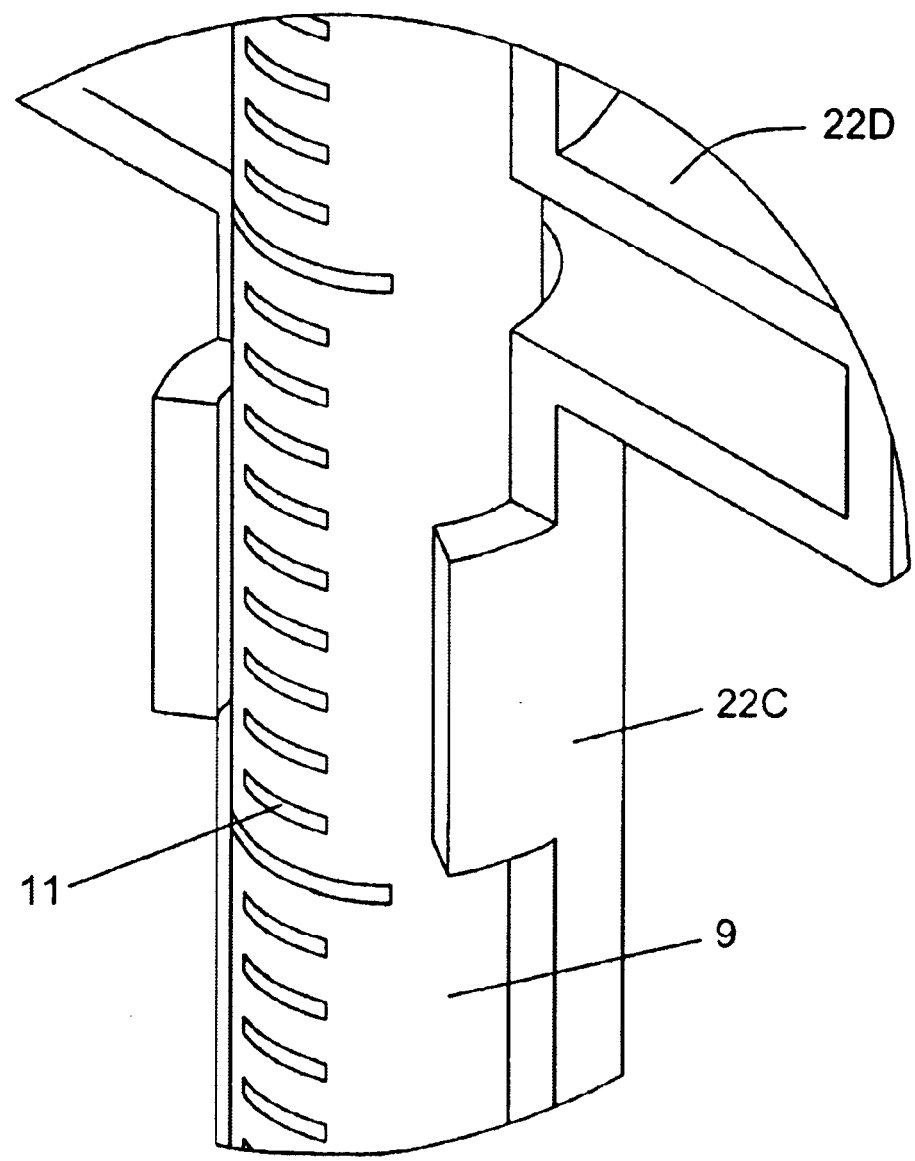
FIG. 1F is a perspective view of the sedimentation tube while the ESR instrument is arranged in its Blood Collection Configuration, showing the graduation markings along the length of the sedimentation measurement tube.

As shown in FIG. 1E, the rupturable membrane 15 is integrally formed with the plunger structure 13 and covers the end opening of the sedimentation measurement tube 9, so as to completely close off the upper portion of the blood collection tube and enable the blood collection tube to be evacuated to a predetermined extent during the instrument assembly process, in a manner well know in the art. As shown, the anti-coagulant 20 contained within hollow interior volume of the sedimentation measurement tube 9 between the air/fluid flow restriction plug 18 and the rupturable membrane 15 of the rubber plunger 13. Notably, it is this vacuum within the blood collection tube 2 that automatically draws a predetermined sample of whole blood (e.g. 1.0 ml or 0.5 ml) from a subject when blood collection apparatus 25 is connected between the blood collection tube and the human subject, as shown in FIG. 3A, 3B, 3C and 3D.

As shown in FIG. 1B, tube holder and restraint assembly 22 has a first portion 22A releasably surrounding flange 17 during blood collection configuration; a second portion 22B for releasably surrounding flange 8 during the blood collection configuration; a third portion 22C for releasably surrounding sedimentation measurement tube 9 during the blood collection configuration; and a third portion 22D for permanently surrounding flange 8 during the ESR measurement configuration and all times thereafter during disposal. By preventing relative movement between the sedimentation measurement tube 9 and the blood collection tube 2, the tube holder and restraint assembly 22 prevents breaking or rupturing the liquid vacuum seal that is created within the pressurized blood collection tube 2 either before or during the drawing of a whole blood sample. This ensures that a collected whole blood sample will not coagulate before the ESR measurement instrument is rearranged into its ESR Measurement Configuration, shown in FIGS. 5C through 6F, which is achieved by removing the tube holder and restraint assembly 2 and manually pushing the sedimentation measurement tube 9 to the bottom of the blood collection tube 2, as shown in FIGS. 6D through 6F.

In the illustrative embodiment, the sedimentation measurement tube 9, the blood collection tube 2 and the air/fluid flow restriction plug 18 can be injection-molded using high-quality medical-grade plastics as currently used to manufacturer plastic blood collection tubes and the like. Rubber cap 5, rubber plunger 13 and washer seal 19 can be made from medical-grade rubber materials in a manner well known in the art.

Referring to FIG. 2, the steps involved in carrying out the method of ESR measurement according to the present invention will now be described in detail.

Figure 3A:
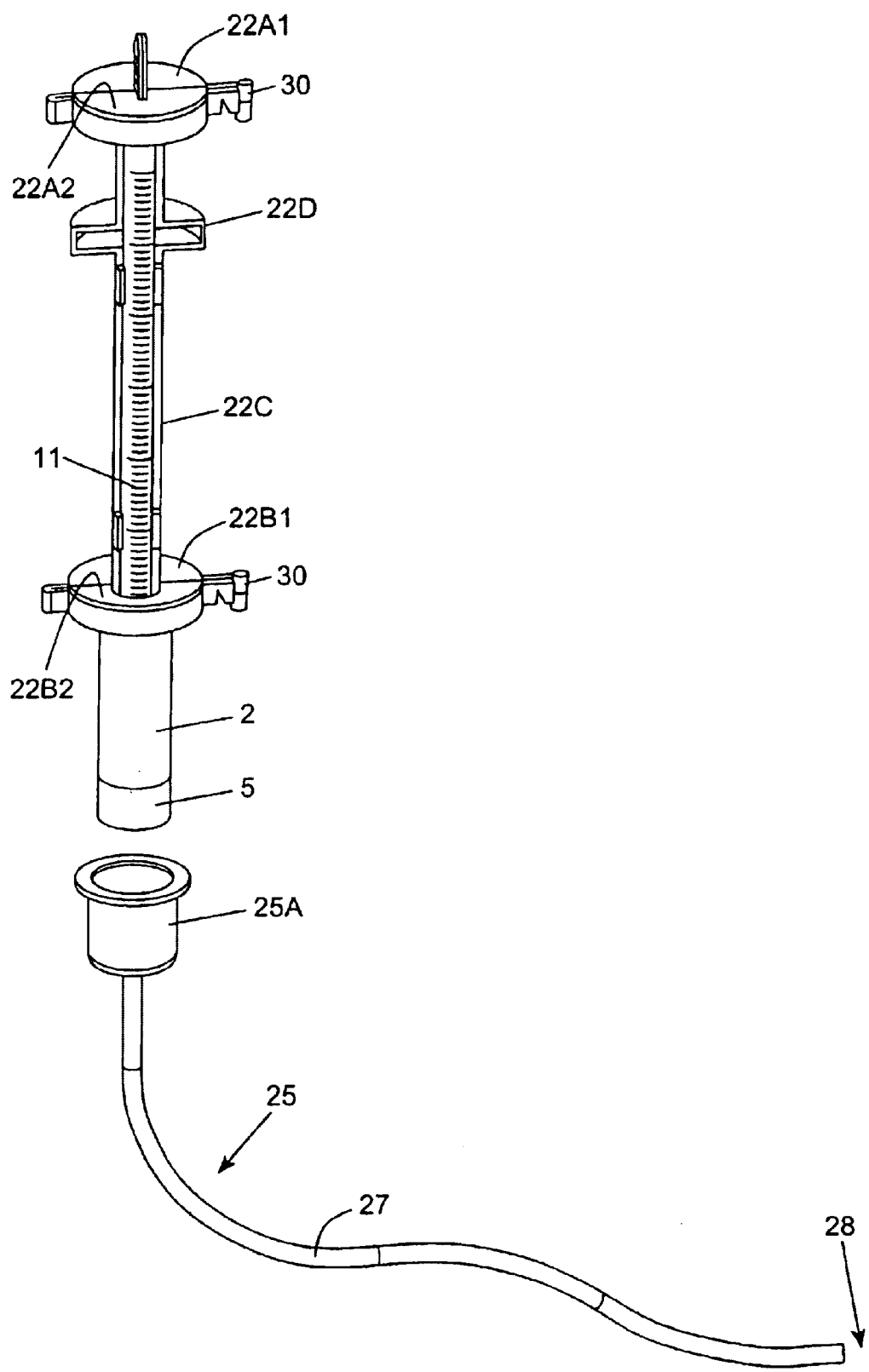
FIG. 3A is a perspective view of the ESR measurement instrument of the first illustrative embodiment, shown arranged in its Blood Collection Configuration and connected to a Vacutainer™ type connector for the drawing of a whole blood sample from a living human being, by venipuncture, in accordance with the method of the present invention.
Figure 3B:
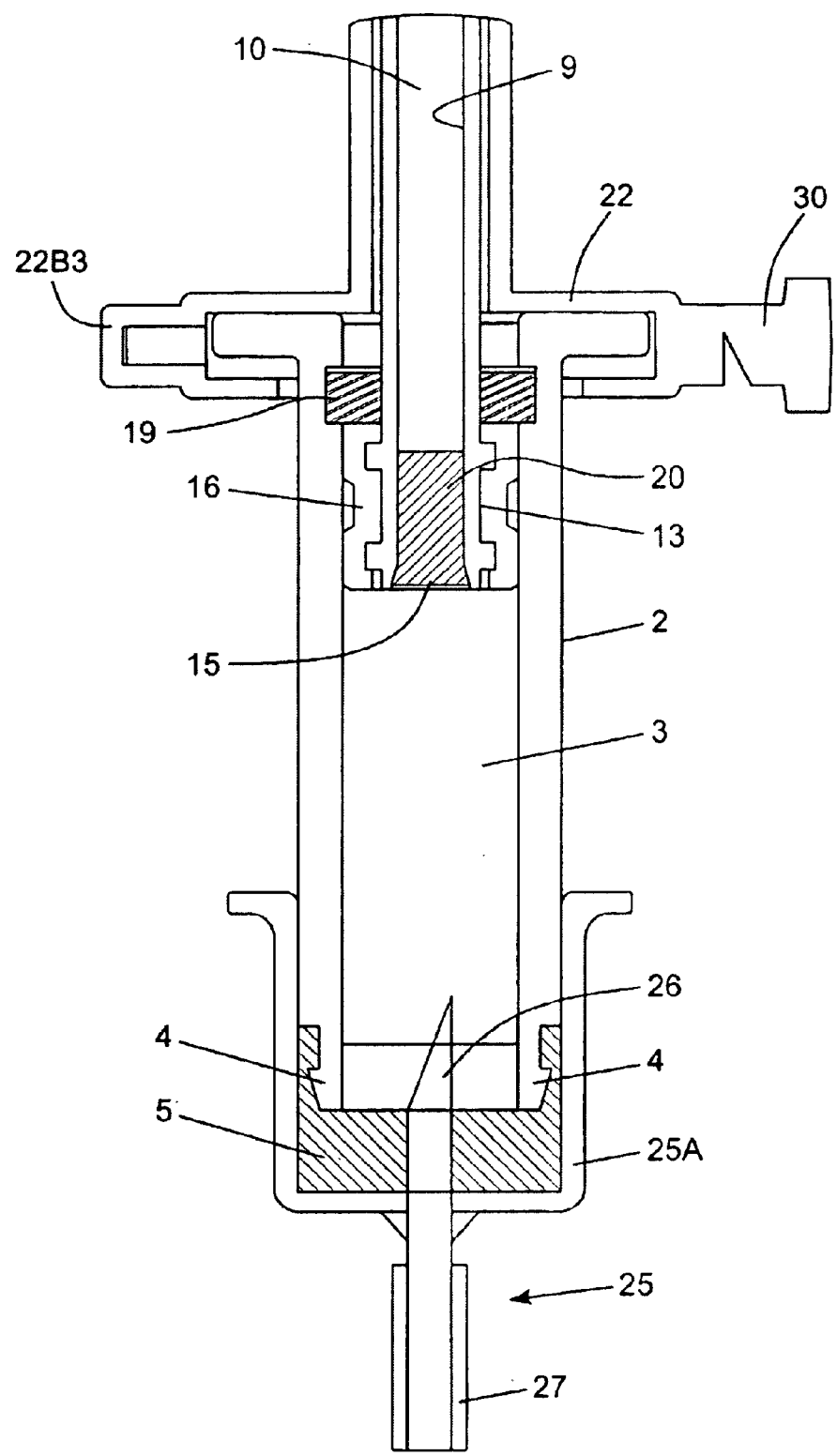
FIG. 3B is a cross-sectional view of the lower portion of the ESR measurement instrument of the first illustrative embodiment, with the Vacutainer™ connector shown connected to the blood collection tube of the ESR measurement instrument, the needle of the connector being pierced through its rubber cap, and a sample of whole blood being automatically drawn into the blood collection tube by virtue of the premeasured vacuum provided within the sealed blood collection tube.
Figure 3C:
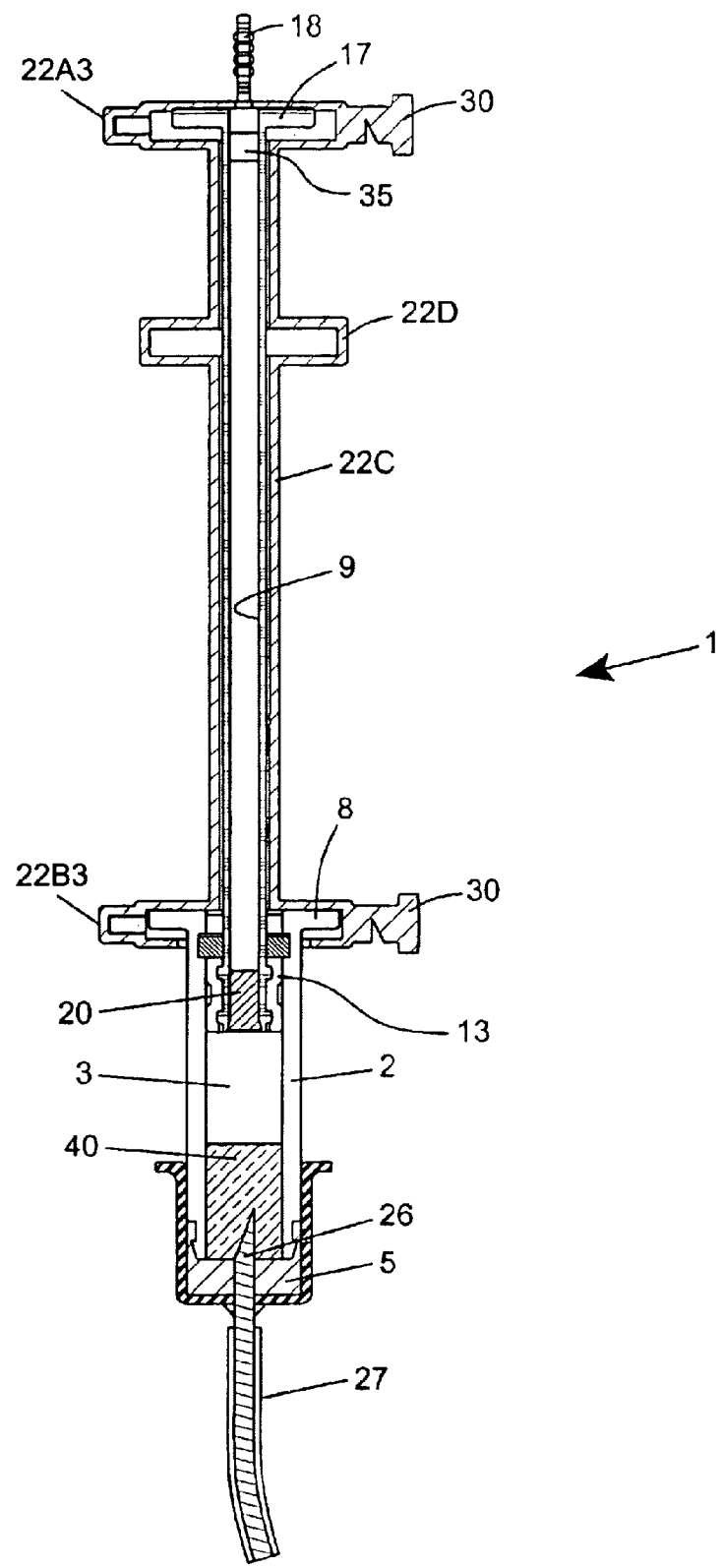
FIG. 3C is a cross-sectional view of the ESR measurement instrument of the first illustrative embodiment, with the Vacutainer™ connector shown connected to the blood collection tube of the ESR measurement instrument, the needle of the connector being pierced through the rubber cap, and the blood collection tube partially filled with a sample of whole blood.

As indicated at Block A of FIG. 2, the first step of the ESR measurement method involves injecting the needle 26 of a Leur® lock type blood collecting apparatus 25 through the rubber cap 5 of the blood collection tube, as shown in FIG. 3B. This connection apparatus occurs with the tube holder and restraint assembly 22 installed about the sedimentation measurement tube 9 and blood collection tube 2, and the air/fluid flow restriction plug 18 remains inserted within the top opening 17A of the sedimentation measurement tube. The blood collection apparatus employed during this step of the method typically will include a section of flexible tubing 27 that is connected to a Leur® lock connector 25A on one end, and terminates in a hypodermic needle 28 on the other. The hypodermic needle should be suitable for safely drawing blood from a human subject. One or more medical connectors may be inserted in-line between the blood collection tube 2 and the hypodermic needle 28, in a manner well known in the art. Once the hypodermic needle punctures the skin of the human subject, the vacuum pressure within the blood collection tube 2 automatically draws a predetermined sample of whole human blood 40, which flows through the tubing and fills up the blood collection container.

As indicated at Block B in FIG. 2, during this blood drawing operation, blood 40 entering the blood collection tube 2 mixes with the quantity of anti-coagulant 21 in the blood collection tube 2 to prevent coagulation of the blood sample within the blood collection tube.

Figure 3D:
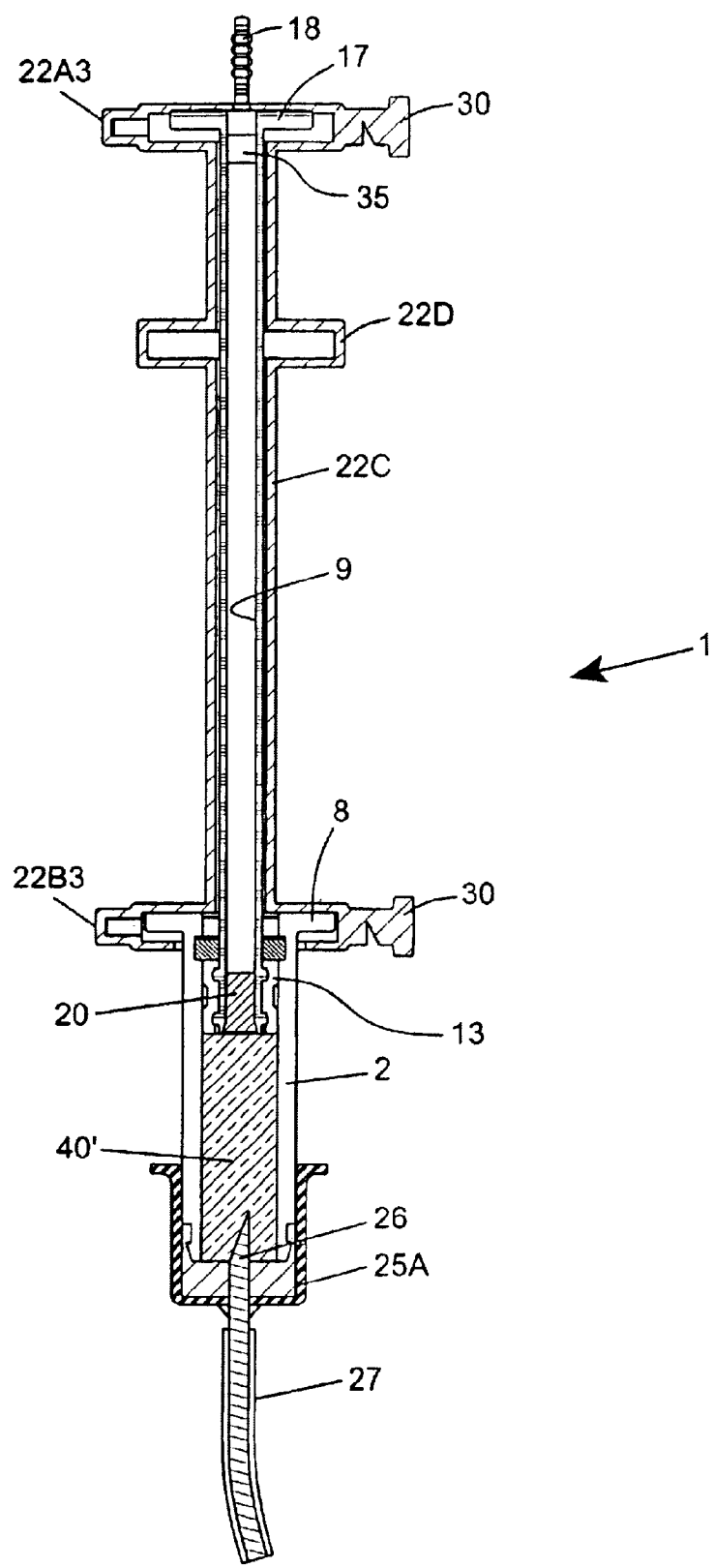
FIG. 3D is a cross-sectional view of the ESR measurement instrument of the first illustrative embodiment, with the Vacutainer™ connector shown connected to the blood collection tube of the ESR measurement instrument, the needle of the connector being pierced through the rubber cap, and the blood collection tube completely filled with a sample of whole blood.
Figure 3E:
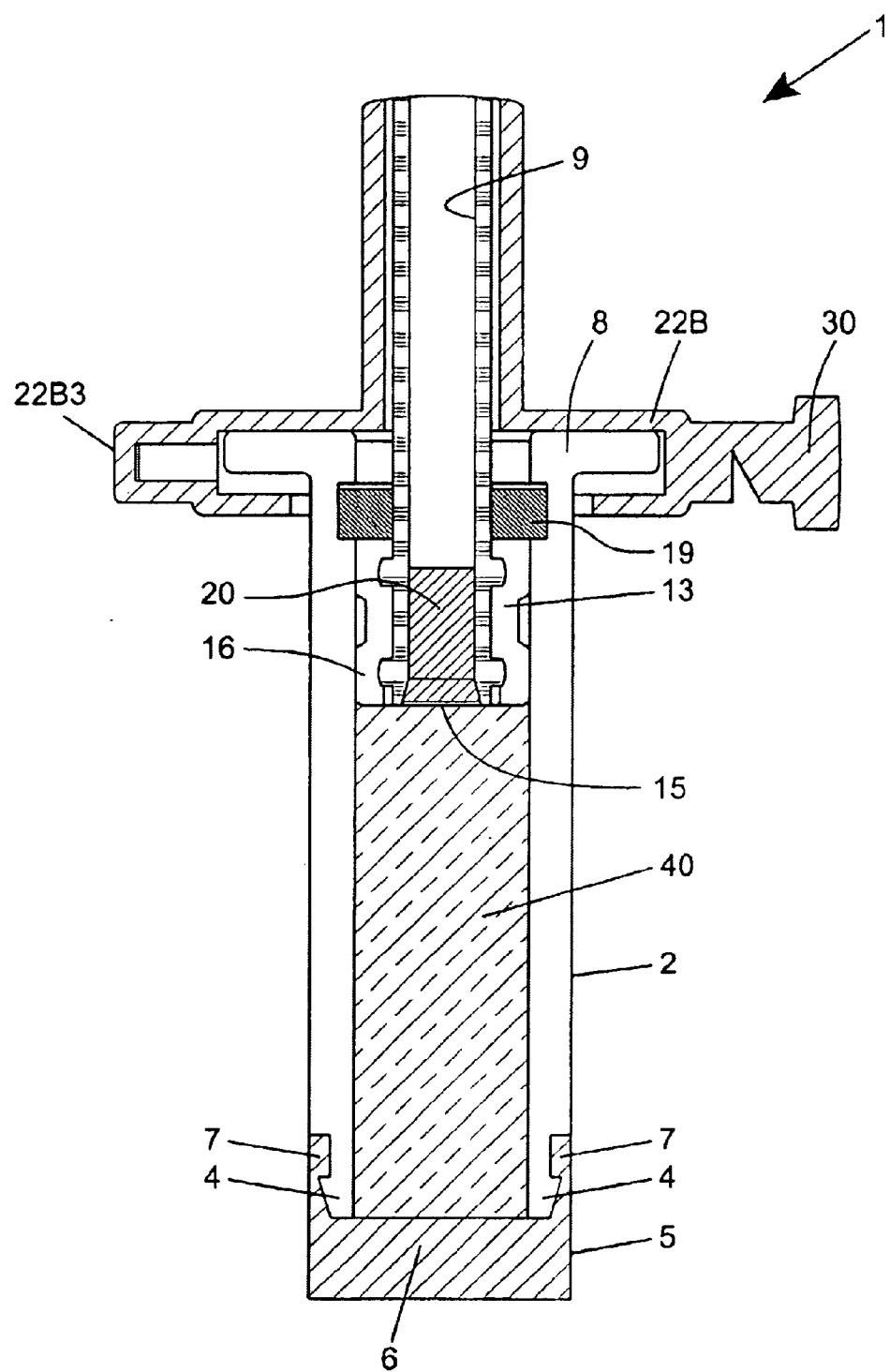
FIG. 3E is an enlarged partially cut-away view of the blood collection tube portion of the ESR measurement instrument of the first illustrative embodiment, shown completely filled with a sample of whole blood, with the rubber plunger, membrane, and washer ring collectively creating a liquid seal between the filled blood collection tube and the dilutent, containing sedimentation measurement tube.
Figure 4A:
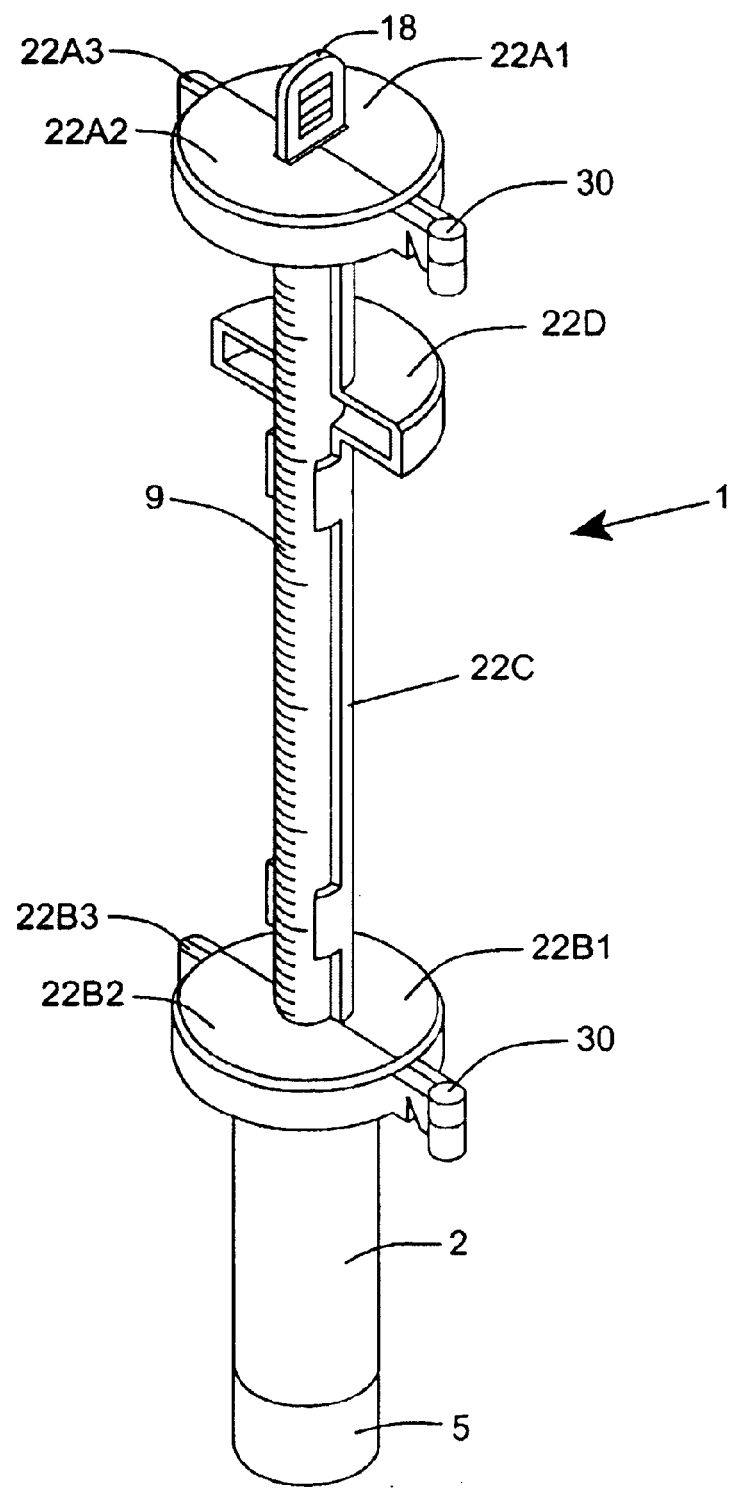
FIG. 4A is a perspective view of the ESR measurement instrument first illustrative embodiment, shown arranged in its Blood Collection Configuration with its tube holder and retainer assembly locked about the sedimentation measurement tube and blood collection tube of the instrument.

As indicated at Block C in FIG. 2, as the blood collection tube 2 is filled to its predetermined volume (e.g. 1 ml) by the vacuum created at the time of instrument assembly, as shown in FIGS. 3D and 3E, the blood from the human subject will stop flowing into the blood collection measurement tube 2, and the needle 28 can be then removed from the human subject and the Leur® lock connector 25A can be withdrawn and removed from the blood collection tube.

Figure 5A:
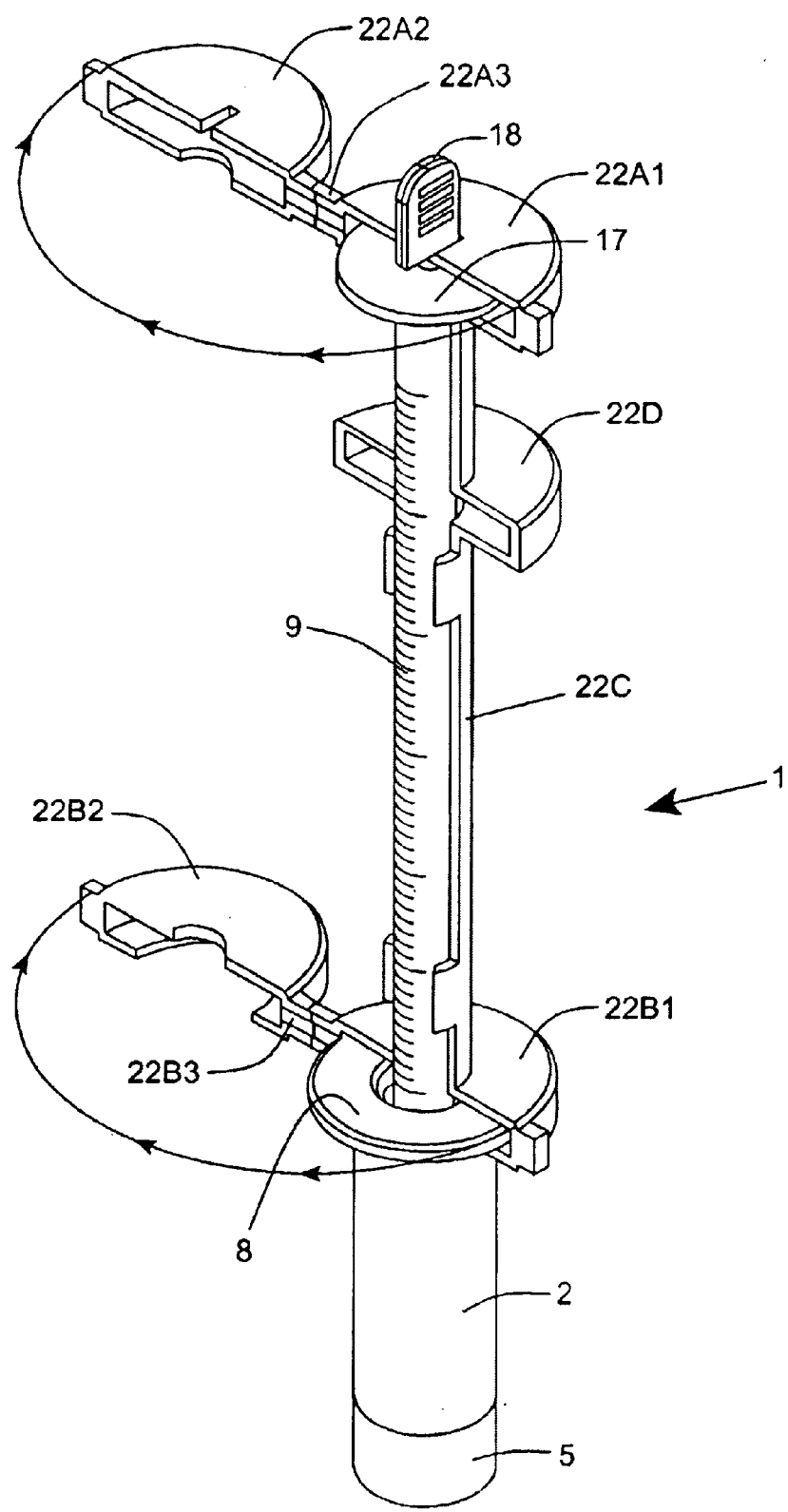
FIG. 5A is a perspective view of the ESR measurement instrument first illustrative embodiment, shown arranged in its Blood Collection Configuration with its tube holder and retainer assembly unlocked from about the sedimentation measurement tube and blood collection tube structures of the instrument so that its top and bottom cover portions can be opened and removed from the respective flanges on the sedimentation measurement tube and blood collection tube structures.
Figure 5B:
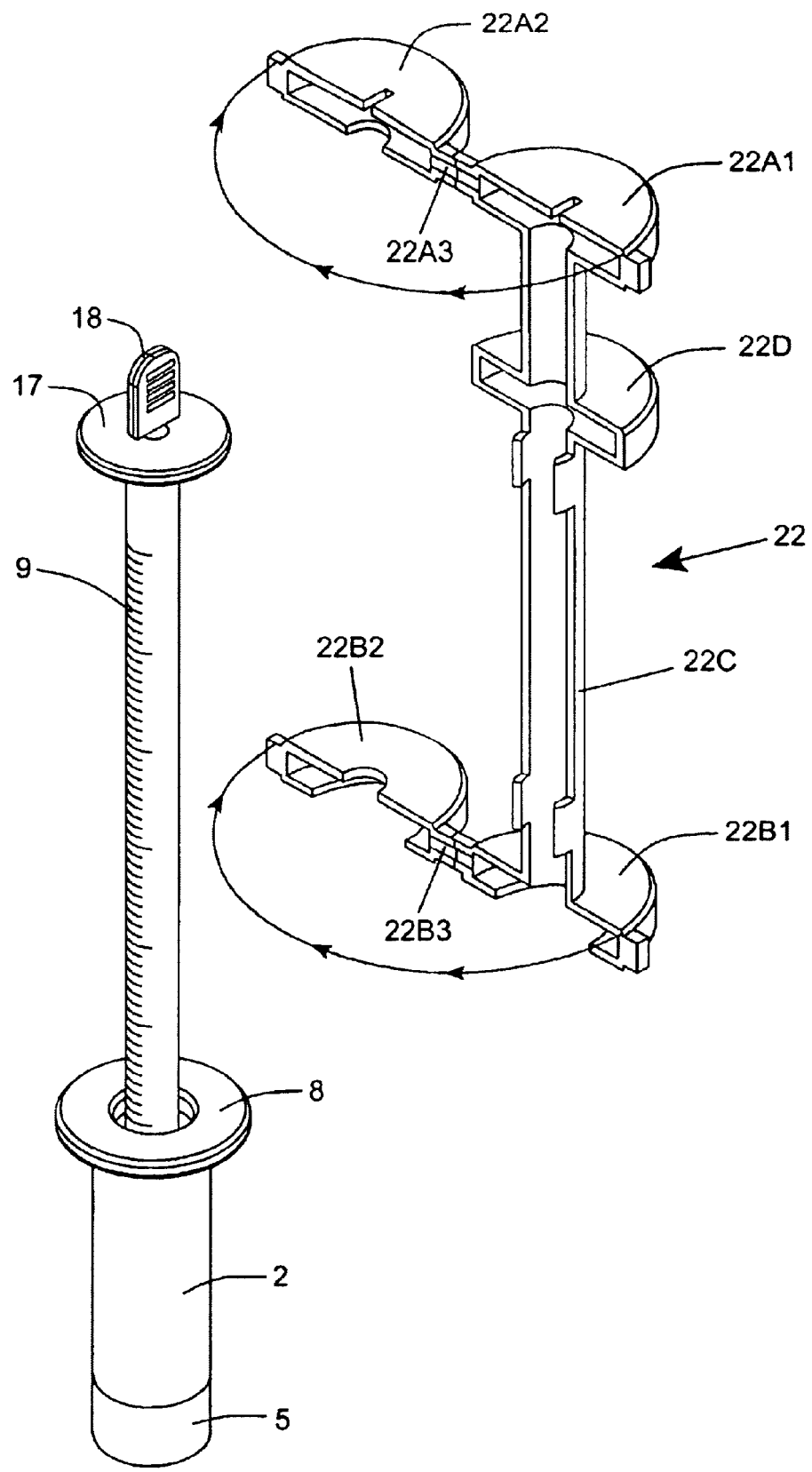
FIG. 5B is a perspective view of the portable/disposable ESR measurement instrument first illustrative embodiment, shown arranged in its Blood Collection Configuration with its tube holder and retainer assembly shown removed from the sedimentation measurement tube and blood collection tube structures of the instrument, and its air/fluid flow restriction plug still inserted within the top aperture of the sedimentation measurement tube.
Figure 5C:
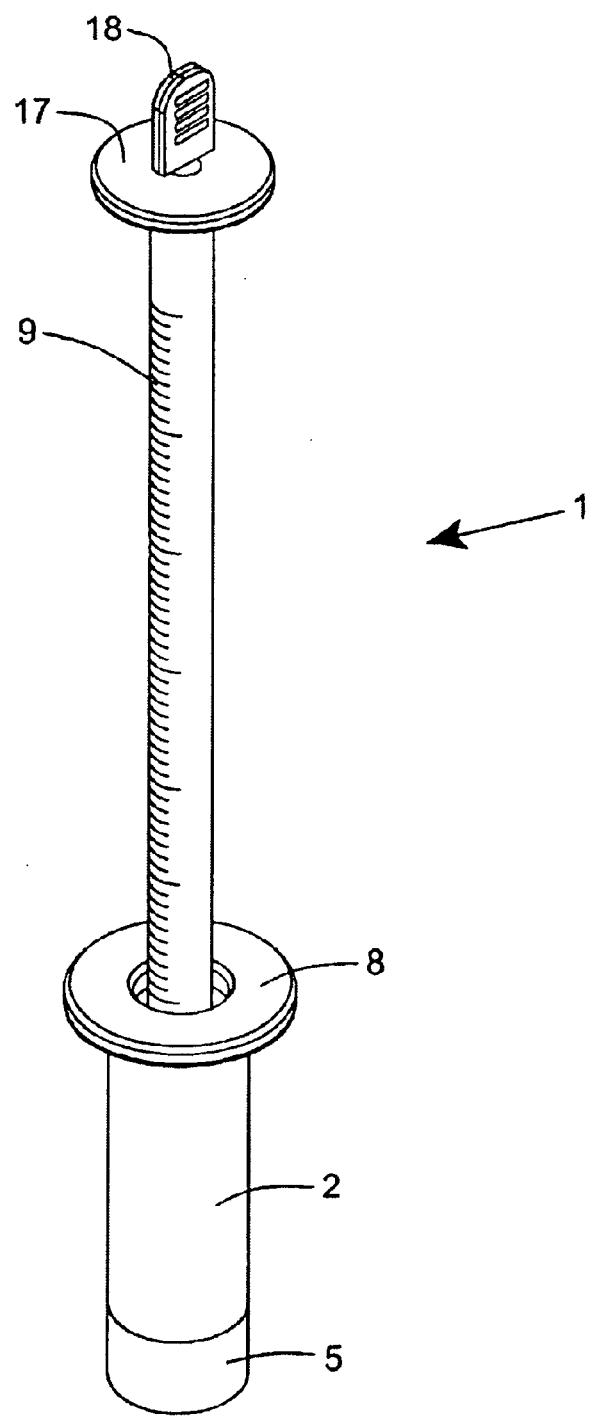
FIG. 5C is a perspective view of the ESR measurement instrument first illustrative embodiment, shown arranged in its ESR Measurement Configuration with the sedimentation measurement tube arranged for manual insertion within the blood collection tube structure of the ESR measurement instrument.
Figure 5E:
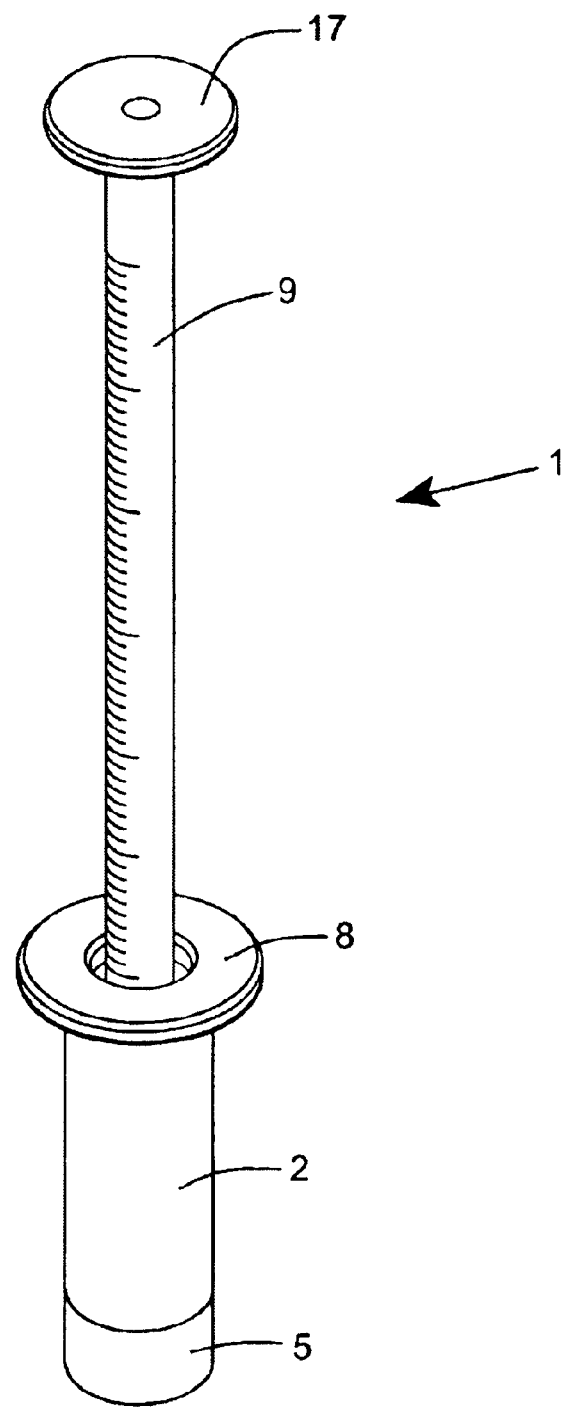
FIG. 5E is a perspective view of the ESR measurement instrument first illustrative embodiment, shown arranged in its Blood Collection Configuration with its tube holder and retainer assembly shown removed from the sedimentation measurement tube and blood collection tube structures of the instrument, and its air/fluid flow restriction plug removed from the top opening in the sedimentation measurement tube.
Figure 5F:
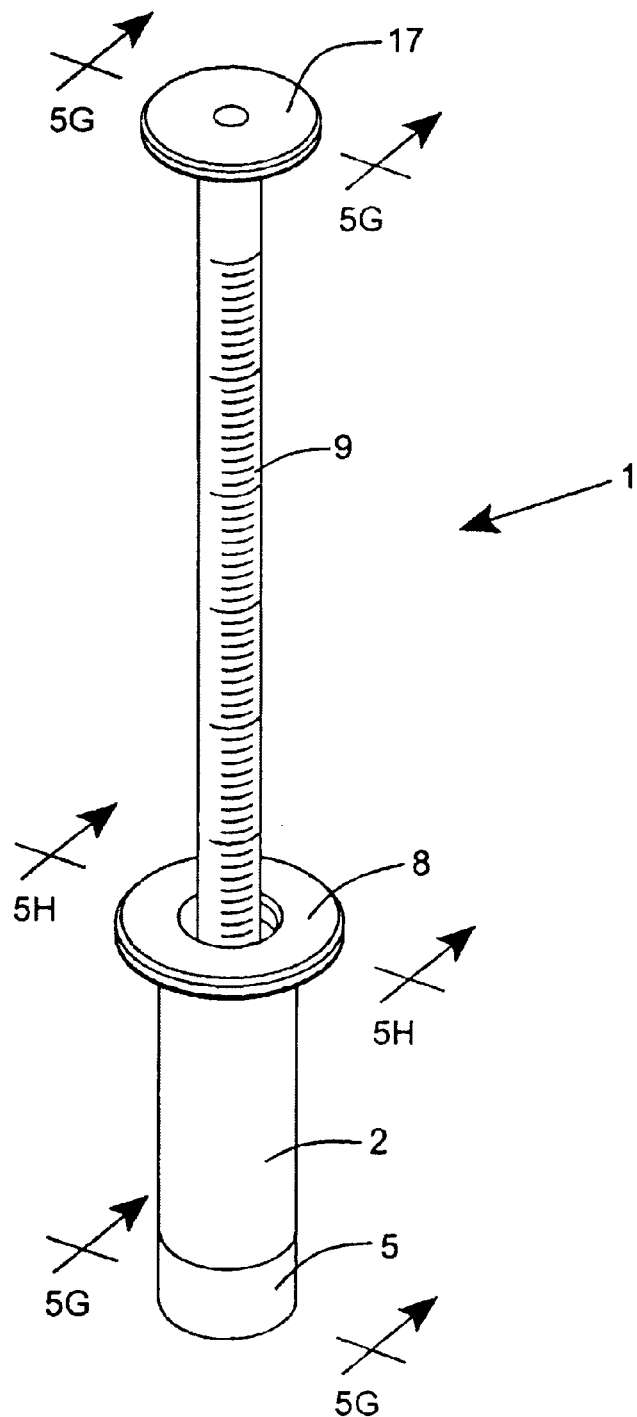
FIG. 5F is a perspective view of the ESR measurement instrument first illustrative embodiment shown arranged in its Blood Collection Configuration with its tube holder and retainer assembly shown removed from the sedimentation measurement tube and blood collection tube structures of the ESR measurement instrument, its air/fluid flow restriction plug removed from the top opening in the sedimentation measurement tube, and the sedimentation measurement tube being manually pushed slightly downward into the blood collection tube.
Figure 5G:
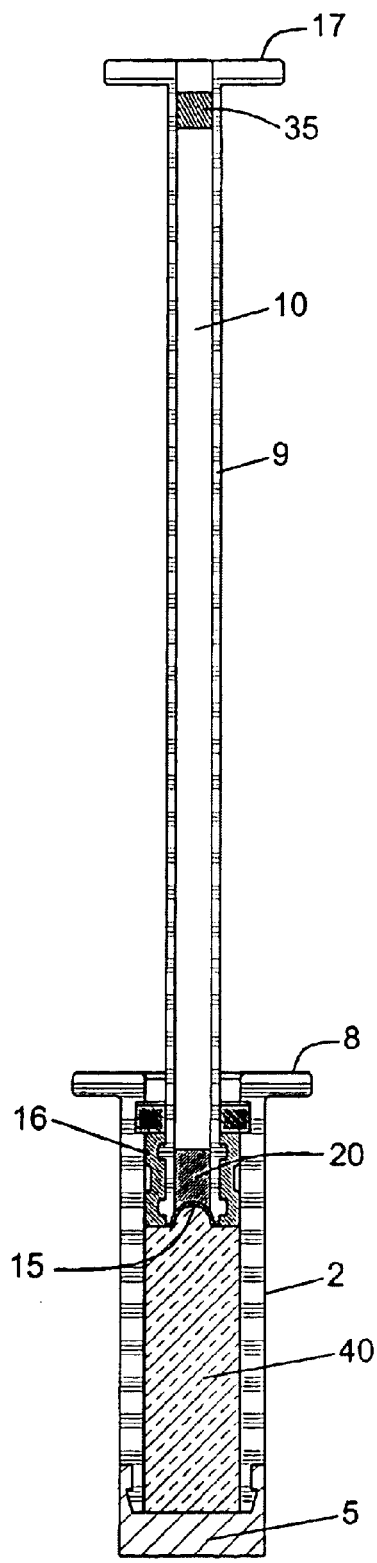
FIG. 5G is a cross-sectional view of the ESR measurement instrument illustrated in FIG. 5F, showing the membrane at the end of the rubber of the plunger being stretched and distorted under pressure, prior to its rupture.

As indicated at Block D of FIG. 2, the next step of the ESR measurement method involves removing the tube holder and restraint assembly 22 from the sedimentation measurement and blood collection tubes as shown in FIGS. 4A through 5B. This is achieved by manually breaking the plastic seal 30 formed at the end portions of the top flange cover halves 22A, 22B, and then opening the cover halves 22A1, 22A2 and 22B1, 22B2 about their respective hinges 22A2 and 22B3 so that the assembly can be removed from the instrument by removing cover halves 22A1, 22A2 and 22B1, 22B2 from top and bottom flanges 17 and 8 respectively, and cover stem portion 22C from sedimentation measurement tube 9. Notably, flange cover half 22D is disposed between stem portion 22C and top cover halves 22B1, 22B2. When the holder and restraint assembly 22 has been removed as shown in FIG. 5B, the instrument is ready to be rearranged into its ESR Measurement Configuration. To do this, the user (e.g. tester or clinician) manually removes the air/fluid flow restriction plug 18 from the top opening of the sedimentation measurement tube 9, as shown in FIGS. 5D1 and 5D2. Upon removal of the air/fluid flow restriction plug 18, ambient air is permitted to flow within the interior volume of the sedimentation measurement tube 9 so that pressure therewithin can be equalized with the air pressure of the ambient environment. In the illustrative embodiment, an air-permeable, blood-impermeable material 37 is inserted within the first inch or so of the hollow interior volume of the sedimentation measurement tube, just about a half inch from the top opening 17A, so that blood, when forced up along and occupying the hollow interior volume 10 during the ESR Measurement Configuration, cannot leak out of the sedimentation measurement tube portion of the ESR measurement instrument.

Figure 5H:
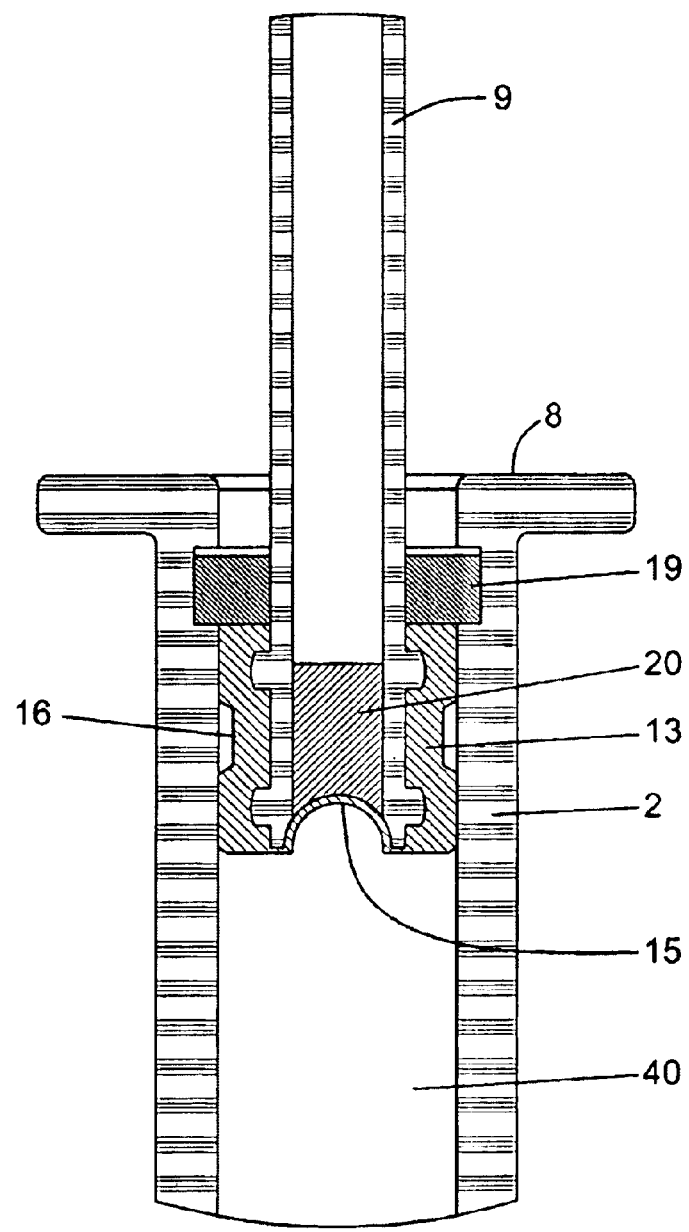
FIG. 5H is a partial enlarged view of the ESR measurement instrument taken along line 5H—5H in FIG. 5F.
Figure 6A:
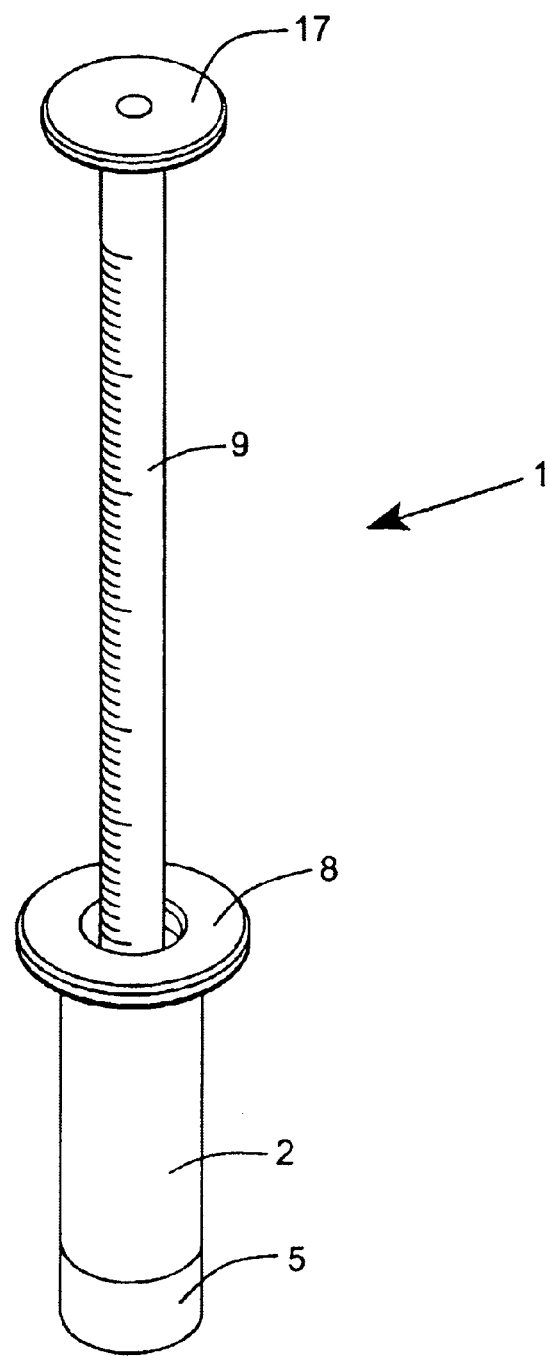
FIG. 6A is a perspective view of the ESR measurement instrument first illustrative embodiment, shown arranged in its Blood Collection Configuration with its tube holder and retainer assembly shown removed from the sedimentation measurement tube and blood collection tube structures of the instrument, its air/fluid flow restriction plug removed from the top opening in the sedimentation measurement tube, and the sedimentation measurement tube being manually pushed downward into the blood collection tube.
Figure 6B:
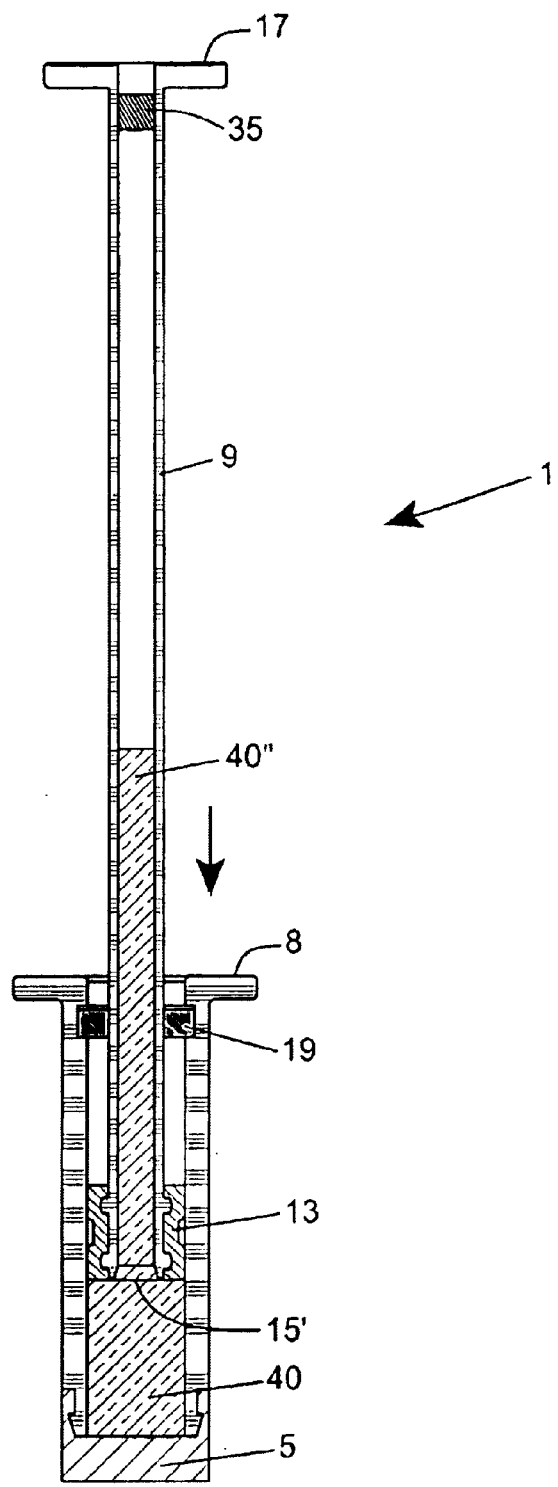
FIG. 6B is a cross-sectional view of the ESR measurement instrument illustrated in FIG. 6A, showing the membrane at the end of the rubber of the plunger ruptured and blood from the blood collection tube injected up about halfway along the interior volume of the sedimentation measurement tube.
Figure 6C:
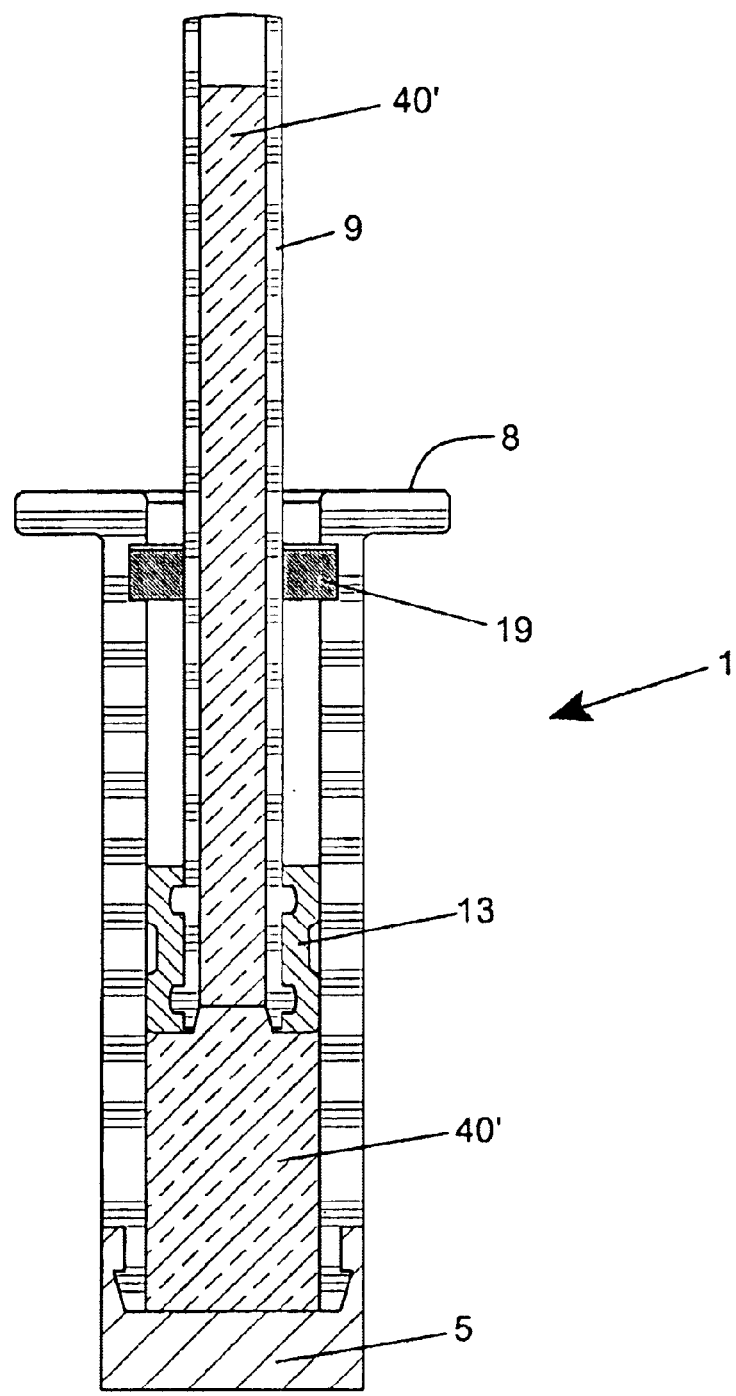
FIG. 6C is a partial enlarged view of the ESR measurement instrument of FIG. 6A.
Figure 6D:
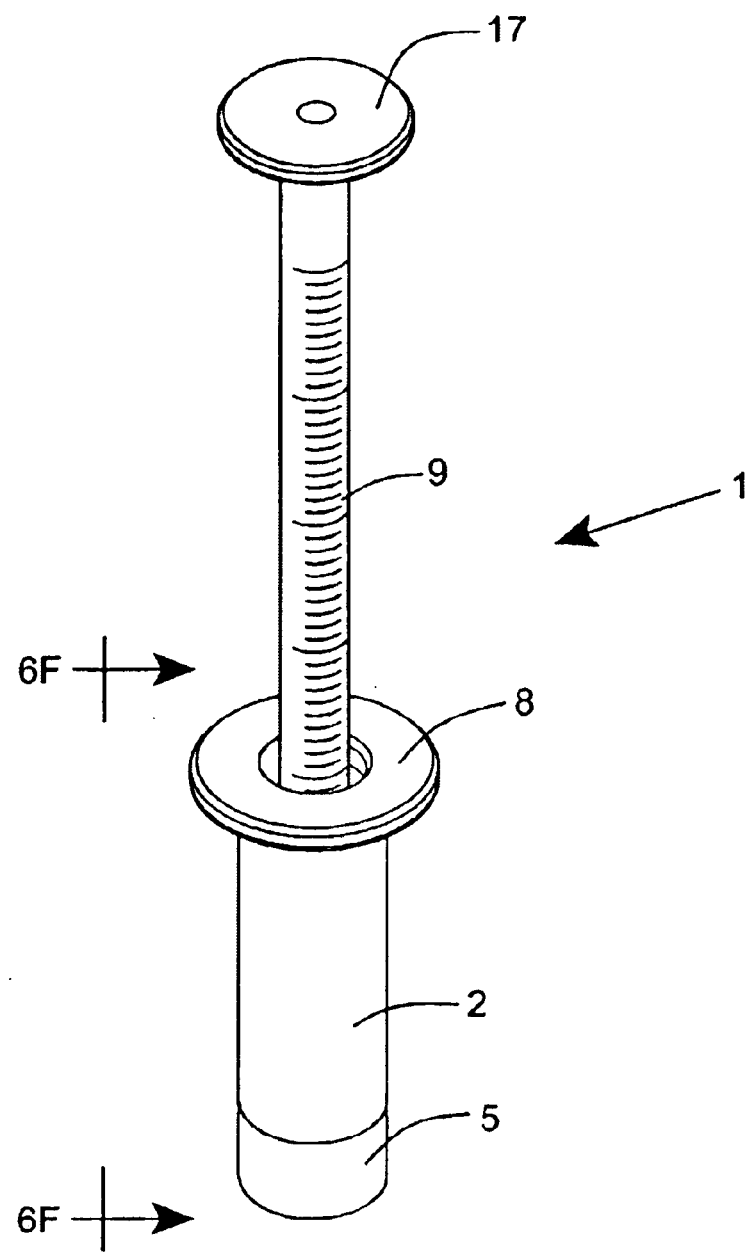
FIG. 6D is a perspective view of the ESR measurement instrument of the first illustrative embodiment shown arranged in its Blood Collection Configuration with its tube holder and retainer assembly shown removed from the sedimentation measurement tube and blood collection tube structures of the instrument, its air/fluid flow restriction plug removed from the top opening in the sedimentation measurement tube, and the sedimentation measurement tube being manually pushed downward to the bottom of the blood collection tube.
Figure 6E:
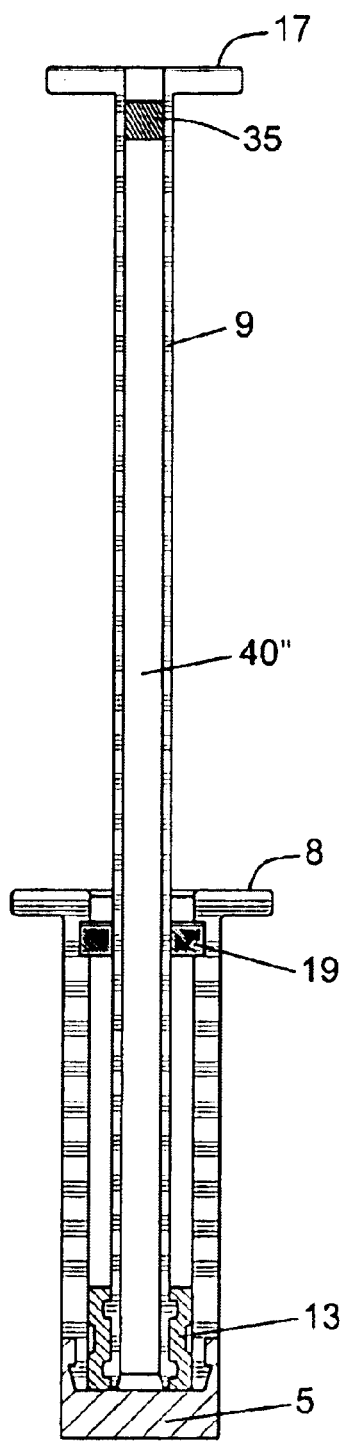
FIG. 6E is a cross-sectional view of the ESR measurement instrument illustrated in FIG. 6D, showing the membrane at the end of the rubber of the plunger ruptured and blood from the blood collection tube injected up along the entire length of the interior volume of the sedimentation measurement tube.
Figure 6F:
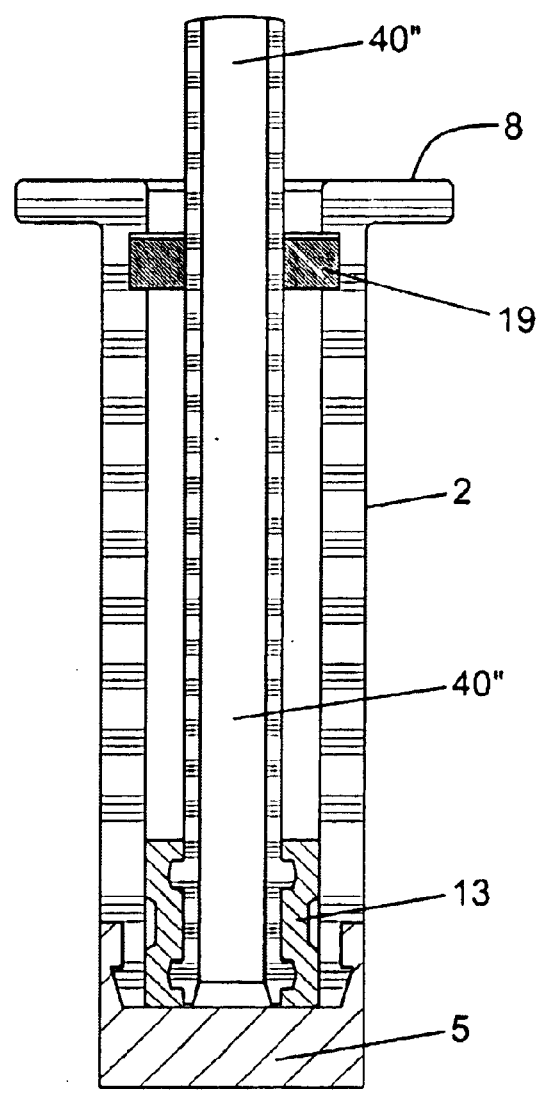
FIG. 6F is a partial enlarged view of the ESR measurement instrument taken along line 6F–6P in FIG. 6D.

As indicated at Block E in FIG. 2, the ESR measurement method involves the user (e.g. tester or clinician) manually grasping the ESR measurement instrument with the lower flange 8 positioned between the user's index and middle fingers, and the user's thumb positioned on the top (i.e. upper) flange 17, as when handling a conventional syringe. In this instrument handling arrangement, the user pushes the sedimentation measurement tube 9 down into the blood collection tube 2 using his or her thumb, just as when expressing liquid from a conventional syringe, as illustrated in FIGS. 5E through 6F. This action causes the rupturable membrane 15 to rupture, and the sample of anti-coagulated blood 40' in the blood collection tube is forced to rush up into the hollow interior volume 10 of the sedimentation measurement tube 9, and mix with the blood sample diluting agent (e.g. physiologic NaCl solution or sodium citrate solution) 20 contained therein. The process of the membrane 15 rupturing in response to the rubber plunger 13 being plunged into the blood collection tube 2 is schematically illustrated in FIG. 5H. As shown, during this process, the membrane 15 stretches as the hydrostatic pressure beneath its surface increases with increasing downward pressure, up until a point where the membrane material fails and ruptures, without compromising the overall structural integrity of the wall portions of the rubber plunger component. As the sedimentation measurement tube 9 is plunged into the blood collection tube 2, the pressure of the blood sample therein increases, causing the blood sample 40' to flow up through the ruptured membrane 15' and along the hollow interior volume of the sedimentation measurement tube to mix with the diluting agent (e.g. physiologic NaCl solution or sodium citrate solution). At the same time, the rubber walls of the plunger 13 and gasket 19 create a high-quality liquid seal that prevents no amount of the collected blood sample 40' to leak out from the combined contained volume 40" created by the hollow interior volume 10 of the sedimentation measurement tube 9 arranged in fluid communication with the hollow interior volume of the blood collection tube 2.

Figure 7A:
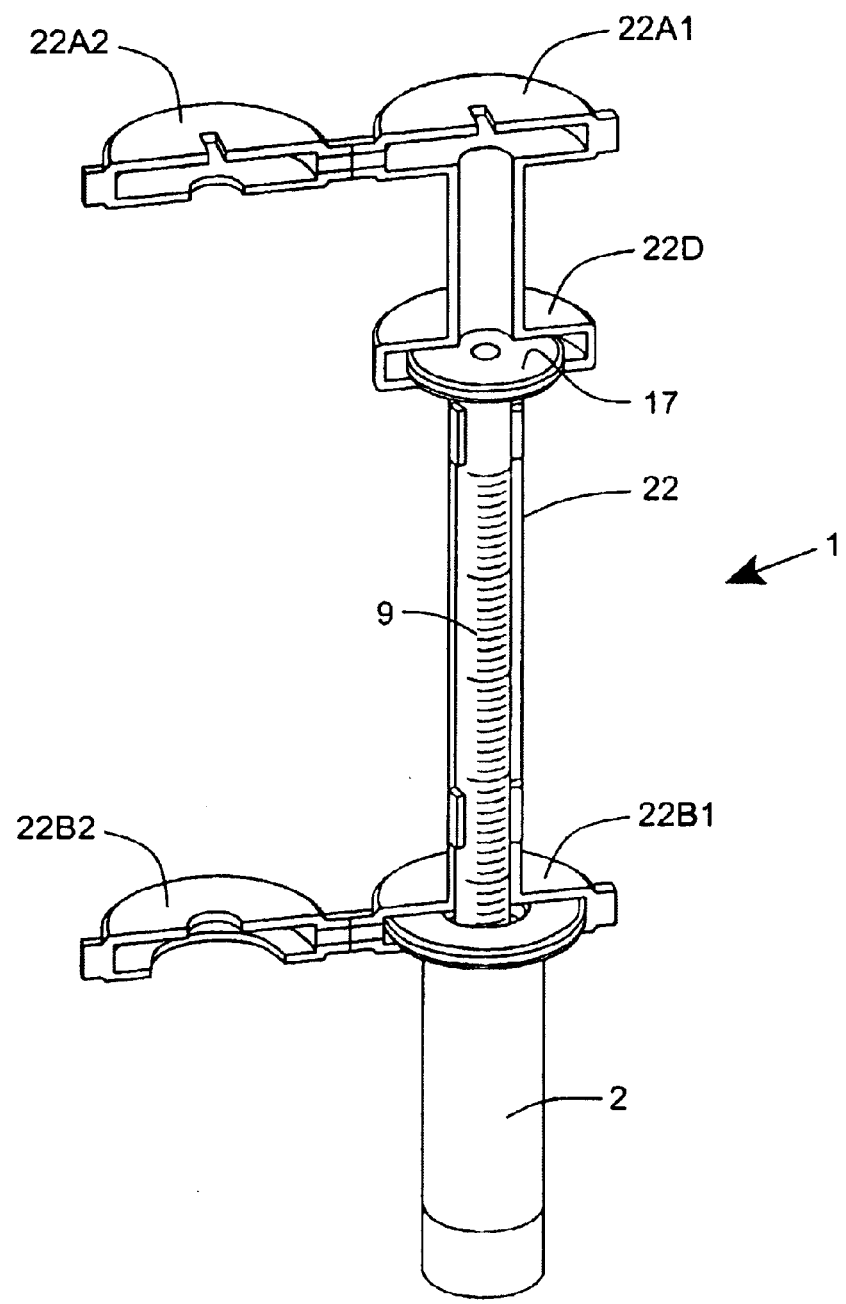
FIGS. 7A, 7B and 7C provide perspective views of the ESR measurement instrument of the first illustrative embodiment, arranged in its ESR Measurement Configuration, with the tube holder and retainer assembly being reinstalled about the sedimentation measurement tube and blood collection tube structures so that these components may be locked securely together, prior to reading of the ESR measurement (i.e. the distance the blood plasma/erythrocyte cell (P/E) interface level has fallen within 60 minutes) along the sedimentation measurement tube, while preventing the spillage of collected blood contained within the blood collection container during and after the time ESR measurements have been taken.
Figure 7B:
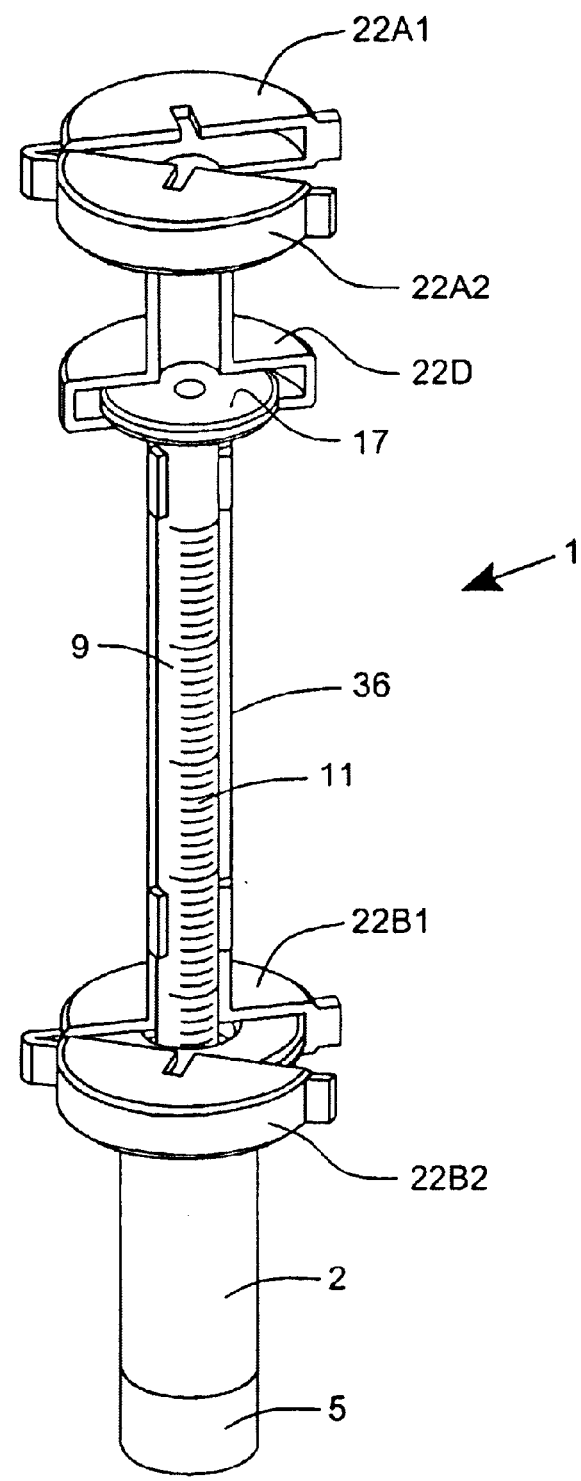
Figure 7C:
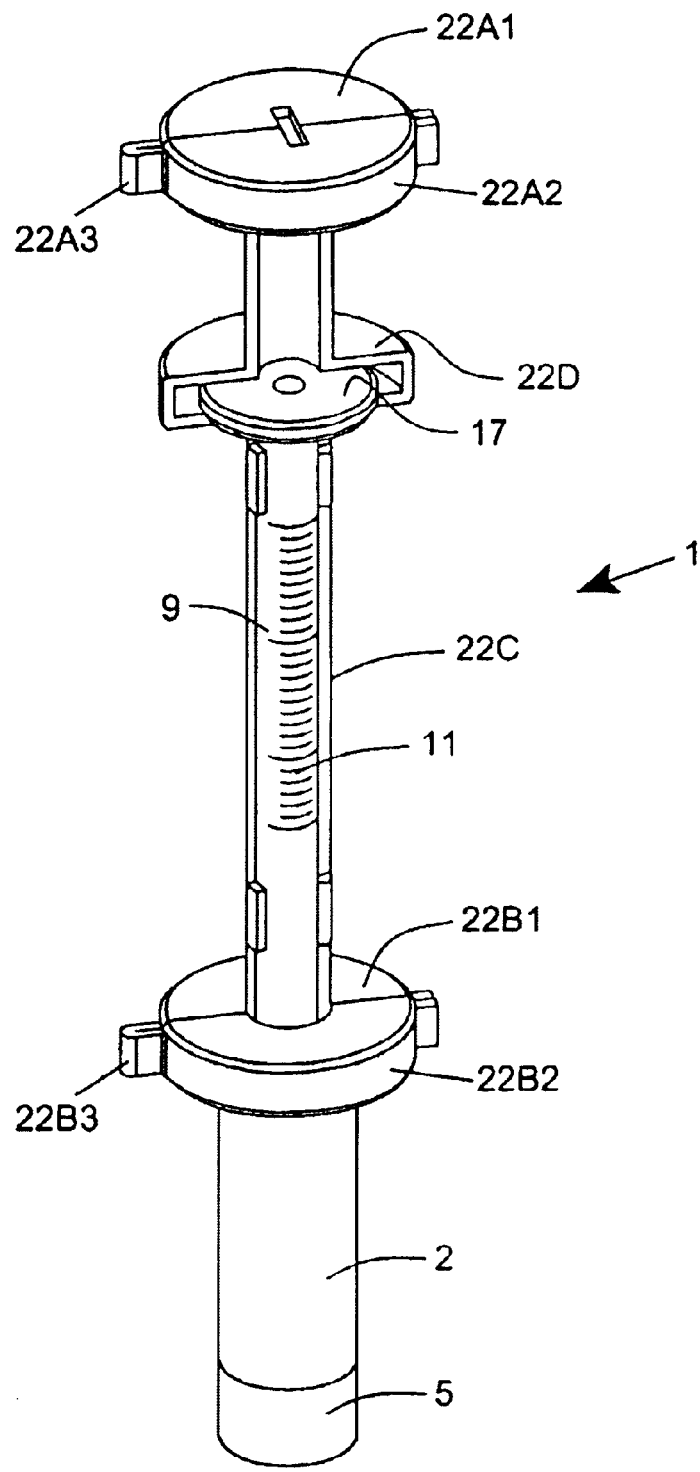
Figure 8:
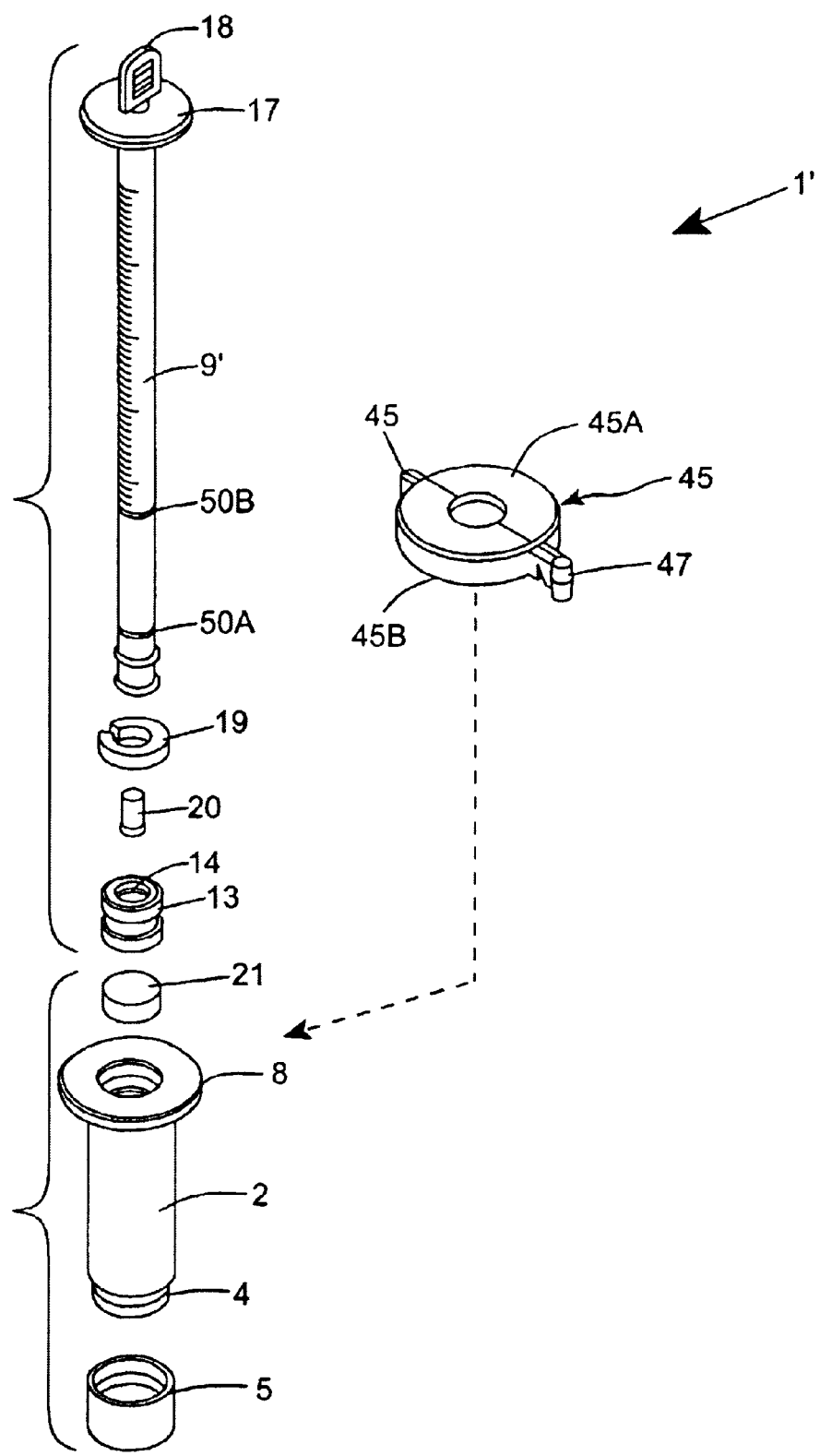
FIG. 8 is an exploded view of the portable/disposable ESR measurement instrument of the second illustrative embodiment, showing that the rubber gasket ring and plunger element are attached to the end of the sedimentation measurement tube after a quantity of blood sample diluting agent is injected into the interior volume of the tube, and that the rubber stopper is attached to the distal end of the blood collection tube and then the blood collection tube is filled with premeasured quantity of anti-coagulant prior to insertion of the plunger end of an assembled and sealed pressurized sedimentation measurement tube during the assembly of the ESR measurement instrument.

Thereafter, the cover halves 22D and 22B1, 22B2 of assembly 22 are reattached about the top and bottom flanges 17 and 8, respectively, as shown in FIGS. 7A and 7B, and then the cover halves are snapped permanently closed as shown in FIG. 7C. In this final state of configuration, the whole anti-coagulated blood sample contained in the ESR measurement instrument is thoroughly mixed with the blood sample diluting agent (e.g. physiologic NaCl solution or sodium citrate solution) 20 to produce a sample of diluted anti-coagulated whole blood (i.e. according to the formula: mix 4 parts of whole anti-coagulated blood with 1 part dilutent). At the same time, the diluted whole blood sample is safely sealed (i.e. entombed) within the locked ESR test instrument. To perform ESR measurement in accordance with the present invention, the ESR measurement instrument is positioned vertically upright, for example, inserted in a stand with a support aperture and bubble-level, (e.g., located on a table, lab bench, or other stable surface) for a time period of about 60 minutes so that the blood plasma/ erythrocyte cell (P/E) interface level is permitted to settle (i.e. fall) along the vertically-supported sedimentation measurement tube during the 60 minute test period, in response to gravitational forces in accordance with convention. At the end of this test period, an accurate ESR measurement can be read by measuring how far the plasma/erythrocyte (P/E) interface has settled in millimeters under the influence of gravity after sixty minutes, i.e. measured in [mm/hr] against the calibrated graduations 11 formed along the length of the sedimentation measurement tube.

After the ESR measurement is taken, and recorded in the patient's medical record, the locked ESR measurement instrument can be discarded as medical waste according to government regulations and/or safety standards.

As the collected blood sample is always contained within the instrument during the ESR measurement method of the present invention, there is little if any risk to the technician performing the ESR test measurement using the ESR measurement instrument of the present invention. Also, as the instrument is essentially locked, the risk of leakage or environmental contamination is substantially minimized.

Second Illustrative Embodiment of the ESR Measurement Instrument of the Present Invention As shown in FIGS. 8 through 17B, the disposable ESR test measurement instrument of the second illustrative embodiment comprises an assembly of components, essentially the same as in the test instrument of the first illustrative embodiment, namely: a blood collection tube 2 having (i) a hollow interior cylindrical volume of a predetermined internal diameter for receiving a sample of whole human blood during blood collection operations, (ii) a pair of low-relief flanges 4 projecting about the outer end surface of the blood collection tube for gripping a rubber needle-pierceable cap 5 with a thick self-sealing end portion 6 and thinner wall portions 7 that snap fit over the low-relief flanges 4 and the outer end portion of the blood collection tube during assembly, and (iii) a large annular flange 8 projecting from the outer end of the blood collection tube at its opposite end, for engagement with the fingers of a person pushing a sedimentation measurement tube 9' within the blood collection tube 2 with his or her thumb; the sedimentation measurement tube 9' having (i) a hollow central bore 10 of a predetermined diameter, (ii) a series of graduation marks 11 formed along the exterior surface thereof for indicating the ESR of a whole blood sample in accordance with the ESR measurement method of the present invention, (iii) a plurality of low-relief plunger gripping flanges 12 projecting from the opposite end of the sedimentation measurement tube for retaining a rubber plunger 13 having a hollow inner volume 14 bounded on its closed end by a thin, rupturable wall membrane 15, and having outer wall surfaces 16 which slide over the free end of the ESR measurement tube and engage the flanges 12 projecting therefrom, (iv) a large annular flange 17 projecting from the outer end of the sedimentation measurement tube at the end opposite the rubber plunger 13, for engagement with the thumb of the person pushing the sedimentation measurement tube 9 within the blood collection tube when rearranging the ESR test measurement instrument into its ESR Measurement Configuration, as shown in FIGS. 12A1 through 17B, and (v) a pair of spaced apart recessed channels 50A and 50B found in surface of sedimentation measurement tube 9' for use with a tube holding and restraint; an air/fluid flow restriction plug 18 insertable into the top end portion of the ESR measurement tube 9 so as to restrict or occlude the flow of air from the ambient environment and the interior of the hollow central bore 10 while the ESR measurement instrument is arranged in its Blood Collection Configuration shown in FIGS. 1B through 1F; a rubber washer 19 slidable over the plunger gripping flanges 12, before rubber plunger 13 is attached to the end of the sedimentation measurement tube, for creating a liquid seal between outer walls of the sedimentation measurement tube and the inner walls of blood collection tube; a predetermined quantity of blood sample diluting agent 20 (e.g. physiologic NaCl solution or sodium citrate solution) inserted within the sedimentation measurement tube 9' after air/fluid flow restriction plug 18 is inserted within central bore 10 but before rubber plunger 13 is snap-fitted over the other end of the sedimentation measurement tube 9'; and a predetermined quantity of anti-coagulation agent (e.g. K3EDTA) inserted within the blood collection tube 2 after the rubber needle-pierceable plunger 5 is snap-fitted over the other end of the blood collection tube 2, but before the plunger end of the ESR measurement tube assembly is inserted within open end portion of the blood collection tube 2.

However, in this second illustrative embodiment, its tube holder and restraint assembly 45 is realized in a markedly simpler construction than the tube holder and restraint assembly 22 used in the first illustrative embodiment. This tube holder and restraint assembly 45 will be described in detail below.

In FIGS. 9A through 11E, the ESR measurement instrument of the second illustrative embodiment is shown arranged in its Blood Collection Configuration. Typically, the instrument would be arranged in this assembled state when packaged and shipped from its manufacturer to the end user (e.g. doctor, hospital, medical clinic, etc.). In this arrangement, the plunger portion 13 of the sedimentation measurement tube 9' is inserted within the upper portion of the blood collection tube 2, and held in a stationary position with respect to the blood collection tube 2 by way of removable tube holder and restraint assembly 45. The small quantity of anti-coagulant (e.g. K3EDTA) contained within the vacuum-sealed blood collection tube prevents a sample of whole blood contained therein from coagulation after collection. As illustrated in the cross-sectional view of FIG. 9B, the primary function of the tube holder and restraint assembly 45 is to prevent relative movement between the ESR measurement tube and the blood collection tube while the ESR measurement instrument is arranged in its Blood Collection Configuration. As shown, the rubber washer 19 is received within an annular recess 23 formed in the upper portion of the blood collection tube 2, slightly beneath the plane in which annular flange 8 projects from the outer walls of the blood collection tube 2. The function of the rubber plunger 19 is to create a liquid seal between the end portion of the sedimentation measurement tube 9' and the walls of the blood collection tube 2.

Figure 9A:
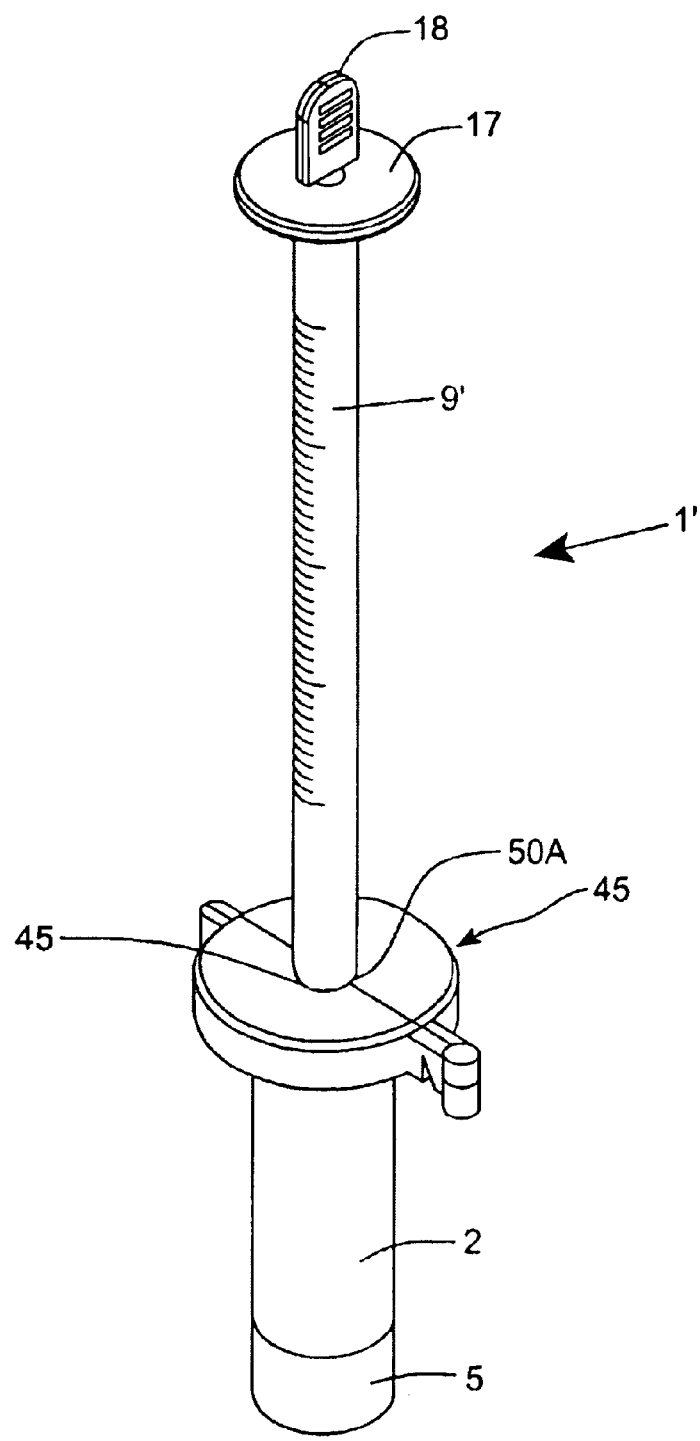
FIG. 9A is a first perspective view of the ESR measurement instrument of the second illustrative embodiment, shown arranged in its Blood Collection Configuration, wherein the plunger portion of the sedimentation measurement tube is inserted within the upper portion of the blood collection tube, and held in a stationary position with respect to the blood collection tube by way of an alternative type of removable tube holder and restraint assembly, so as to not break the liquid seal created within the pressurized blood collection tube containing a small quantity of anti-coagulant for preventing a whole blood sample contained therein from coagulation after collection.
Figure 9B:
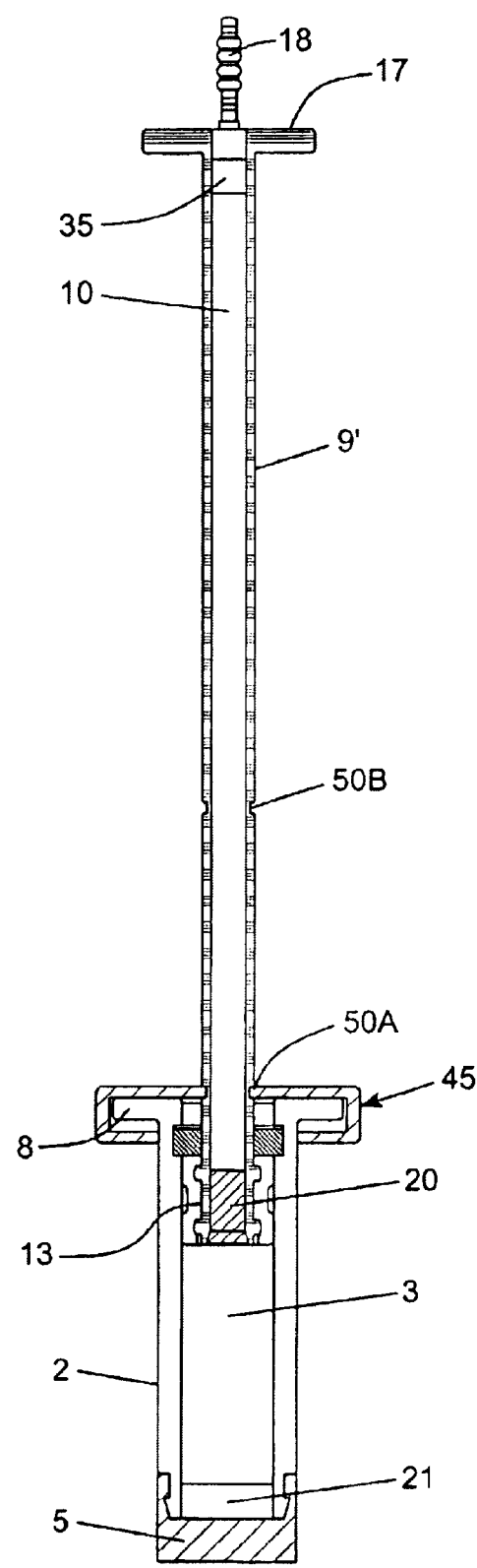
FIG. 9B is a cross-sectional view of the ESR measurement instrument of the second illustrative embodiment taken along line 9B—9B of FIG. 9A, wherein the plunger portion of the sedimentation measurement tube is inserted within the upper portion of the blood collection tube and held in a stationary position with respect to the pressurized blood collection tube by way of the tube holder and restraint assembly, so as to not break the liquid seal created between the blood collection tube and the sedimentation measurement tube, while the ESR measurement instrument is arranged in its Blood Collection Configuration.
Figure 9C:
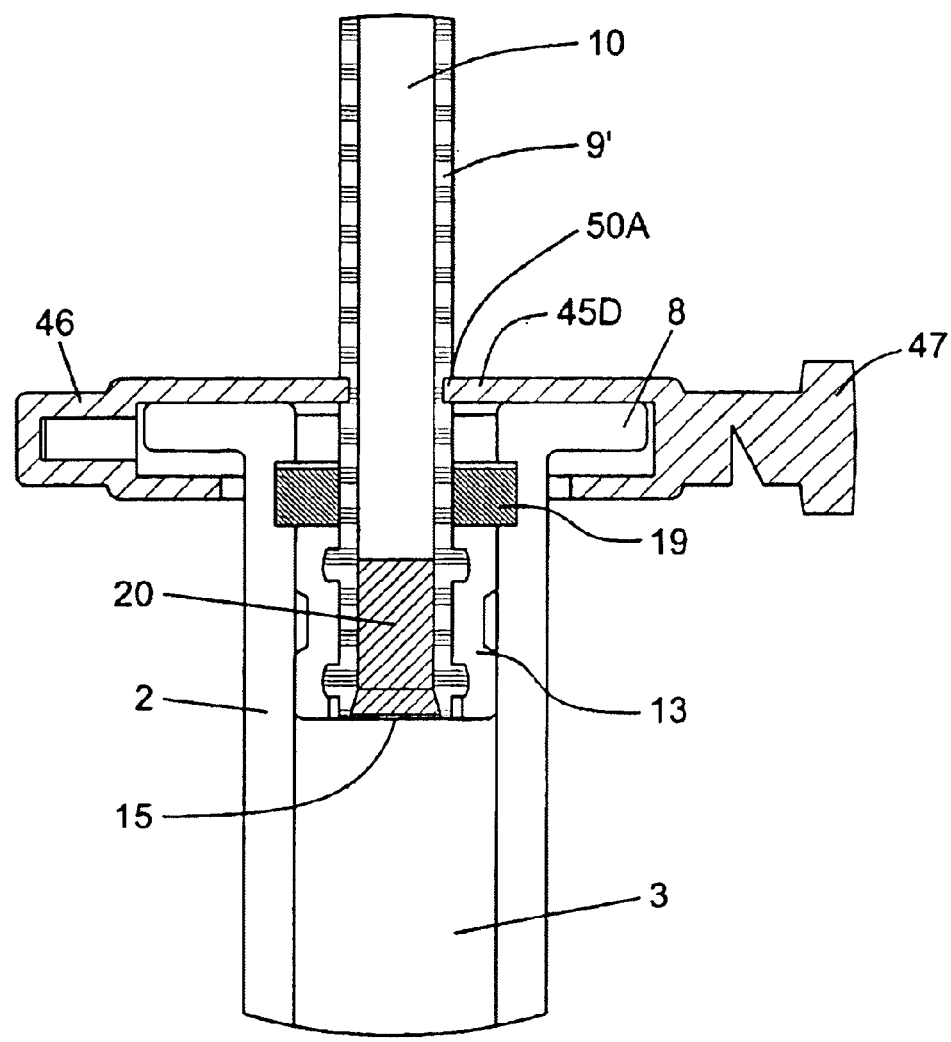
FIG. 9C is a cross-sectional enlarged view of the portion of the ESR measurement instrument of the second illustrative embodiment taken along line 9C—9C of FIG. 9C, showing in greater detail that the plunger portion of the sedimentation measurement tube comprises a rubber plunger element affixed to the free end of the hollow sedimentation measurement tube, and rubber frangible membrane covering the end opening thereof at the distal end of rubber plunger, so as to retain a premeasured quantity of blood sample diluting agent (i.e. physiologic NaCl solution or sodium citrate solution) within the sedimentation measurement tube while the ESR measurement instrument is arranged in its Blood Collection Configuration.

As shown in FIG. 9C, the rupturable membrane 15 is integrally formed with the plunger structure 13 and covers the end opening of the sedimentation measurement tube 9', so as to completely close off the upper portion of the blood collection tube and enable the blood collection tube to be evacuated to a predetermined extent during the instrument assembly process, in a manner well know in the art. As shown, the blood diluting agent (e.g. physiologic NaCl solution or sodium citrate solution) 20 contained within hollow interior volume of the sedimentation measurement tube 9' between the air/fluid flow restriction plug 18 and the rupturable membrane 15 of the rubber plunger 13. Notably, it is this vacuum within the blood collection tube that automatically draws a predetermined undiluted sample of anti-coagulated whole blood (e.g. 1.0 ml or 0.5 ml) from a subject when blood collection apparatus 25 is connected between the blood collection tube and the human subject, as shown in FIGS. 11A, 11B, 11C and 11D. By preventing relative movement between the sedimentation measurement tube 9' and the blood collection tube 2, the tube holder and restraint assembly 45 prevents breaking or rupturing the liquid vacuum seal that is created within the pressurized blood collection tube 2 either before or during the drawing of a whole blood sample. This ensures that a collected whole blood sample will not coagulate before the ESR instrument is rearranged into its ESR Measurement Configuration, shown in FIGS. 12A1 through 17B, which is achieved by removing the tube holder and restraint assembly 45 and manually pushing the sedimentation measurement tube 9 to the bottom of the blood collection tube 2, as shown in FIGS. 13 through 16B.

In the illustrative embodiment, the sedimentation measurement tube, the blood collection tube and the air/fluid flow restriction plug can be injection-molded using high-quality medical-grade plastics as currently used to manufacturer plastic blood collection tubes and the like. Rubber cap 5, rubber plunger 13 and washer seal 19 can be made from medical-grade rubbers in a manner well known in the art.

Referring to Blocks A and B in FIG. 10, the steps involved in carrying out the method of ESR measurement according to the present invention will now be described in detail using the ESR test measurement instrument of the second illustrative embodiment.

Figure 11A:
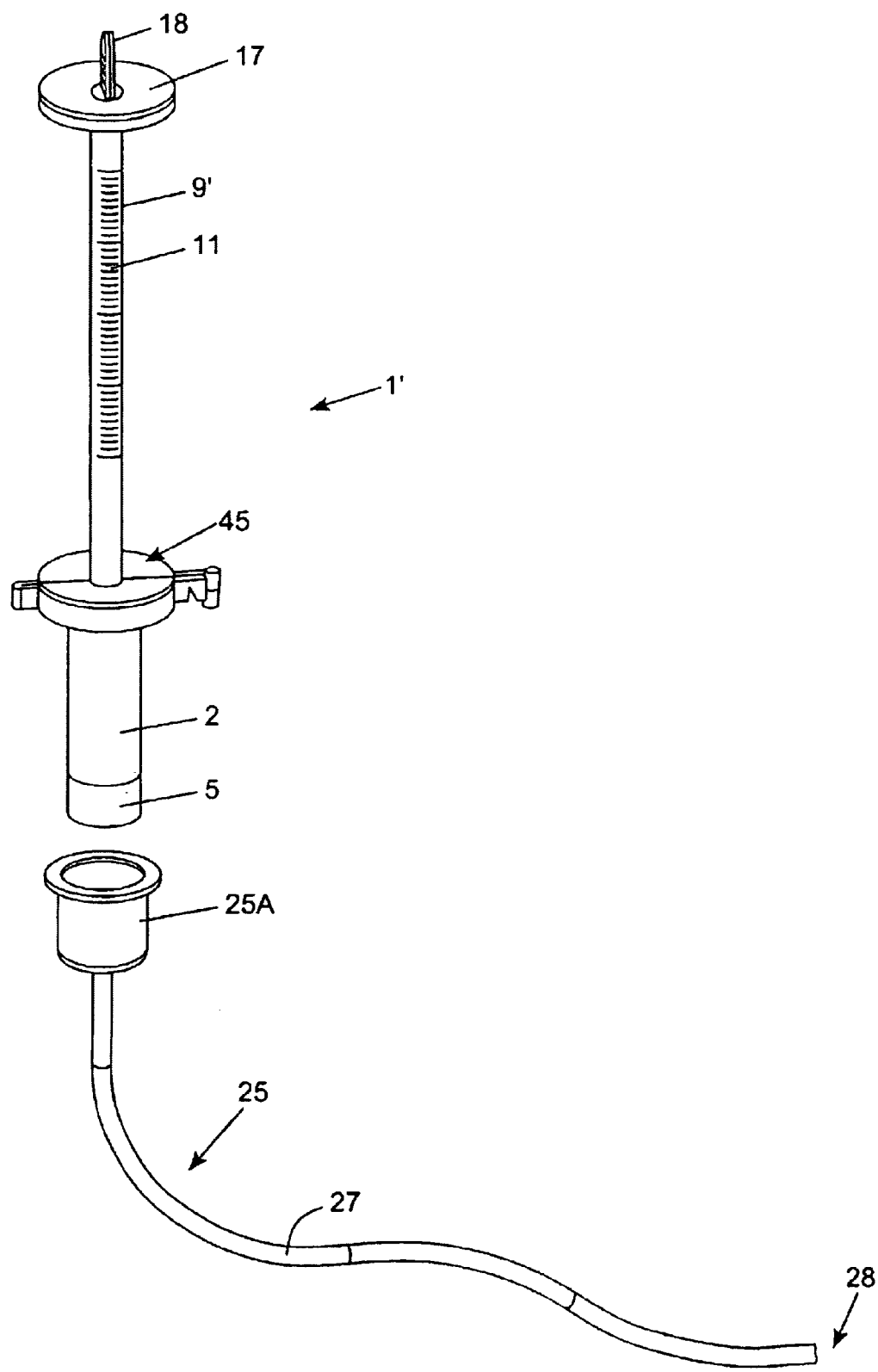
FIG. 11A is a perspective view of the ESR measurement instrument of the second illustrative embodiment, shown arranged in its Blood Collection Configuration and being connected to a Vacutainer™ type connector used during the drawing of a whole blood sample from a living human being, by venipuncture, in accordance with the present invention.
Figure 11B:
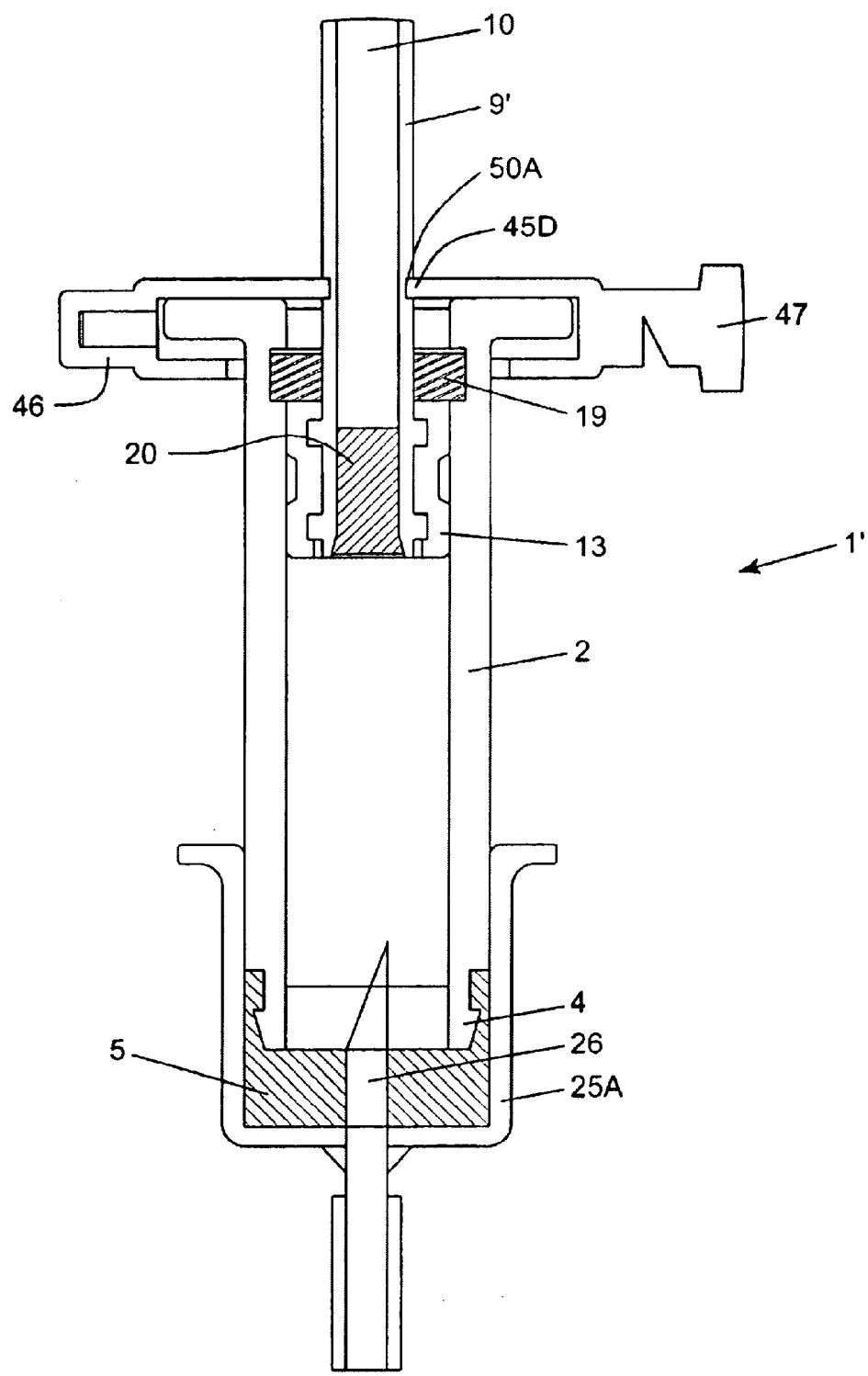
FIG. 11B is a cross-sectional view of the lower portion of the ESR measurement instrument of the second illustrative embodiment, with the Vacutainer™ connector shown connected to the blood collection tube of the ESR measurement instrument, the needle of the connector being pierced through the rubber stopper, and the blood collection tube containing the sample of anti-coagulant agent (i.e. K3EDTA)
Figure 11C:
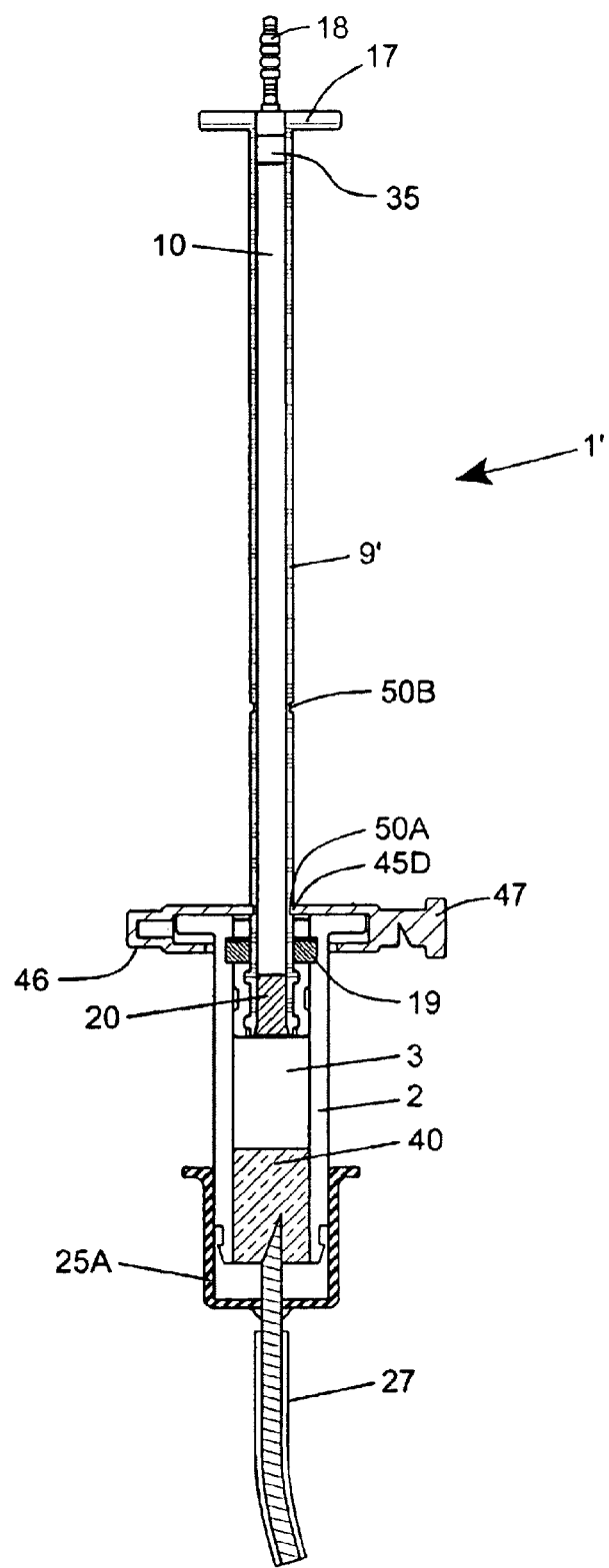
FIG. 11C is a cross-sectional view of the ESR measurement instrument of the second illustrative embodiment, with the Vacutainer™ connector shown connected to the blood collection tube of the ESR measurement instrument, the needle of the connector being pierced through the rubber stopper, and the blood collection tube partially filled with a sample of whole blood.

As indicated at Block A of FIG. 10, the first step of the ESR measurement method involves injecting needle of a Leur® lock type blood collecting apparatus 25 through the rubber cap 5 of the blood collection tube, as shown in FIG. 11A. This connection apparatus occurs with the tube holder and restraint assembly maintained installed about the sedimentation measurement and blood collection tubes, and the air/fluid flow restriction plug 19 remains inserted within the top opening 17A of the sedimentation measurement tube 9'. The blood collection apparatus employed during this step of the method typically will include a section of flexible tubing 27 that is connected to a Leur® lock connector on one end, and terminates in a hypodermic needle 28 on the other. The hypodermic needle should be suitable for safely drawing blood from a human subject. One or more medical connectors may be inserted in-line between the blood collection tube and the hypodermic needle, in a manner well known in the art. Once the hypodermic needle punctures the skin of the human subject, the vacuum pressure within the blood collection tube 2 automatically draws a predetermined sample of whole human blood 40, which flows through the tubing 27 and fills up the blood collection container 2.

As indicated at Block B in FIG. 10, during this blood drawing operation, blood 40 entering the blood collection tube 2 mixes with the quantity of anti-coagulant in the blood collection tube to prevent coagulation of the blood sample within the blood collection tube.

Figure 11D:
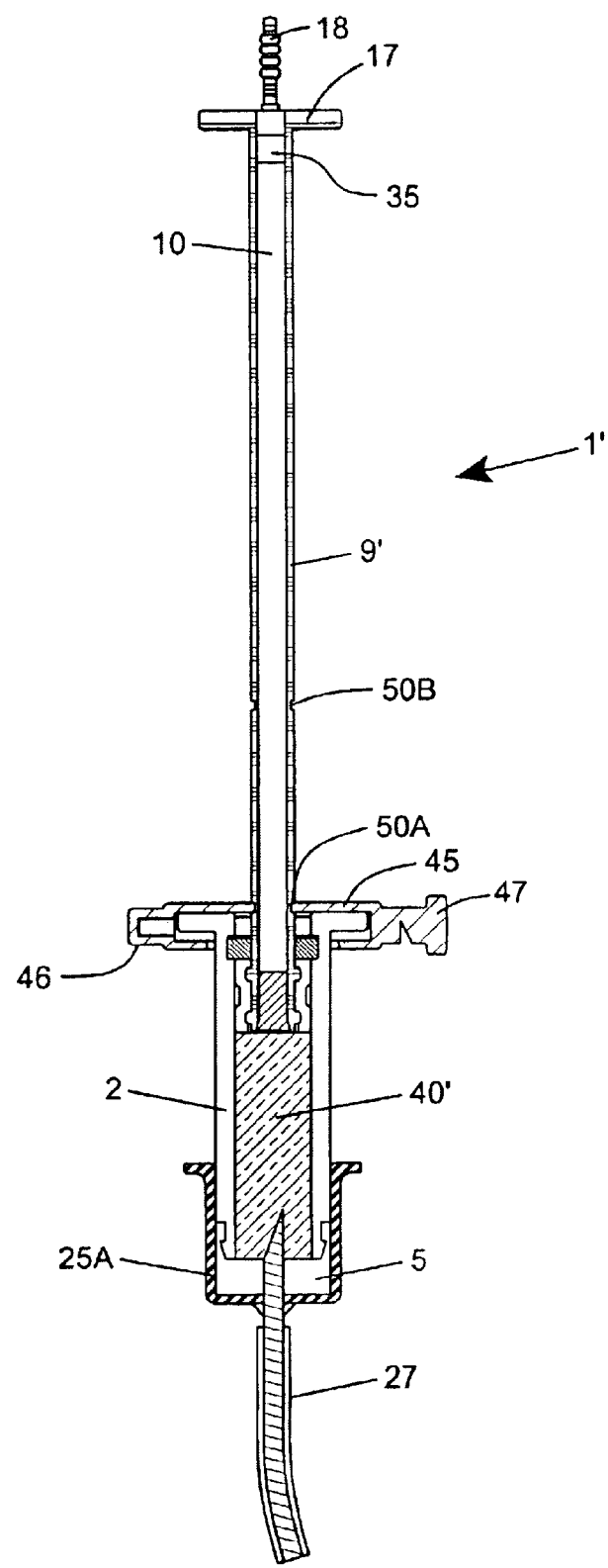
FIG. 11D is a cross-sectional view of the ESR measurement instrument of the second illustrative embodiment, with the Vacutainer™ connector shown connected to the blood collection tube of the ESR measurement instrument, the needle of the connector being pierced through the rubber stopper, and the blood collection tube completely filled with a sample of whole blood.
Figure 11E:
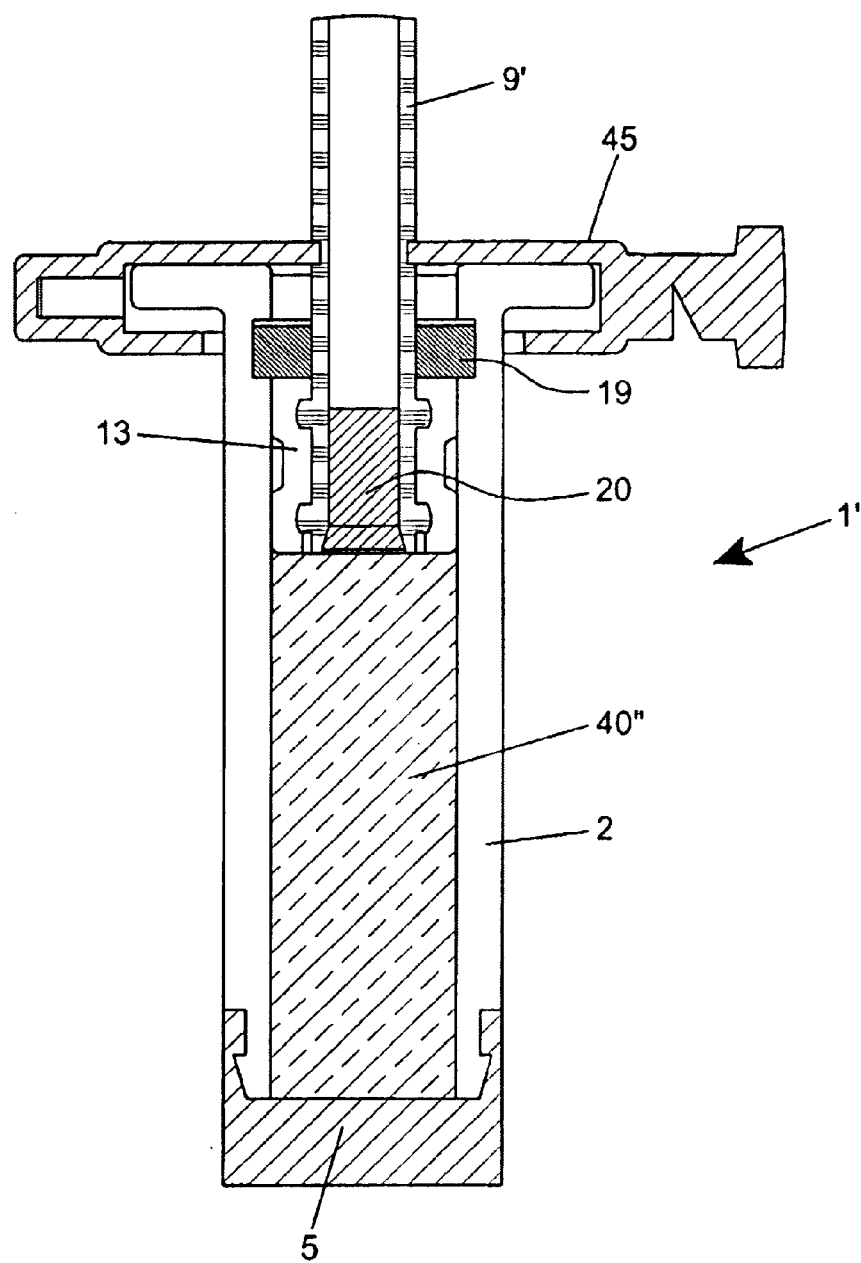
FIG. 11E is an enlarged partially cut-away view of the blood collection tube portion of the ESR measurement instrument of FIG. 11D shown completely filled with a sample of whole blood, and the rubber plunger, membrane, and washer ring, collectively creating a liquid seal between the filled blood collection tube and the empty sedimentation measurement tube.

As indicated at Block C in FIG. 10, as the blood collection tube is filled to its predetermined volume (e.g. 1 ml) by the vacuum created at the time of instrument assembly, as shown in FIGS. 11D and 11E, whole blood from the human subject will stop flowing into the blood collection measurement tube 2, and the needle 28 can be then removed from the human subject and the Leur® lock connector 25A can be withdrawn and removed from the blood collection tube 2.

Figure 13:
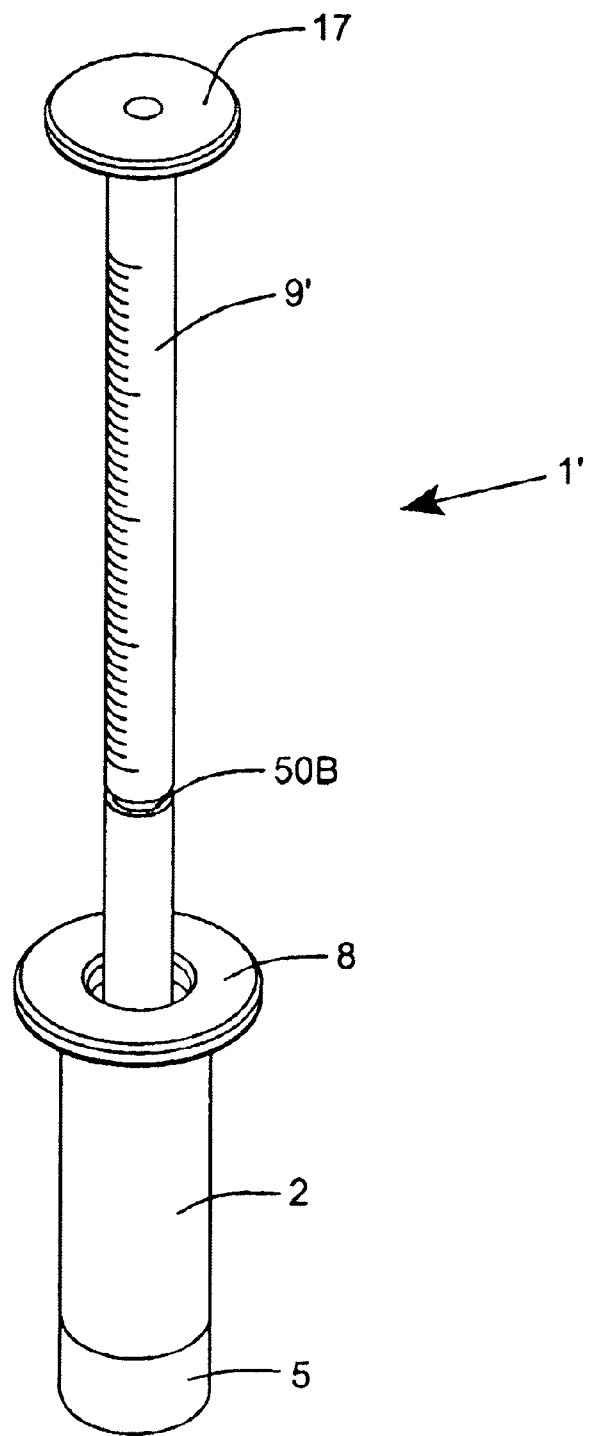
FIG. 13 is a perspective view of the ESR measurement instrument of the second illustrative embodiment shown arranged in its Blood Collection Configuration with its blood collection tube partially filled with a sample of whole anti-coagulated blood, its tube holder and retainer assembly shown removed from the sedimentation measurement tube and blood collection tube structures of the instrument, and its air/fluid flow restriction plug removed from the top opening in the sedimentation measurement tube.

As indicated at Block D of FIG. 10, the next step of the ESR measurement method involves removing the tube holder and restraint assembly 45 from the sedimentation measurement and blood collection tubes as shown in FIGS. 12A1. This is achieved by manually breaking the plastic seal 47 formed at the end portions of the flange cover halves 45, 45 and then opening the cover halves about their hinge 46 so that the assembly 45 can be removed from about flange 8 associated with the ESR measurement instrument. When the holder and restraint assembly 45 has been removed as shown in FIG. 13, the ESR measurement instrument is ready to be rearranged into its ESR Measurement Configuration. To do this, the user (e.g. tester or clinician) manually removes the air/fluid flow restriction plug 18 from the top opening of the sedimentation measurement tube 9', as shown in FIGS. 12A2 and 12A3. Upon removal of the air/fluid flow restriction plug 18, ambient air is permitted to flow within the interior volume 10 of the sedimentation measurement tube 9' so that pressure therewithin can be equalized with the air pressure of the ambient environment. In the illustrative embodiment, an air-permeable, blood-impermeable material 37 is inserted within the first inch or so of the hollow interior volume of the sedimentation measurement tube, just about a half inch from the top opening 17A, so that the sample of anti-coagulated blood, when forced up along and occupying the hollow interior volume 10 during the ESR Measurement Configuration, mixes with the blood diluting agent (e.g. physiologic NaCl solution or sodium citrate solution) and cannot leak out of the sedimentation measurement tube of the ESR test measurement instrument.

Figure 14A:
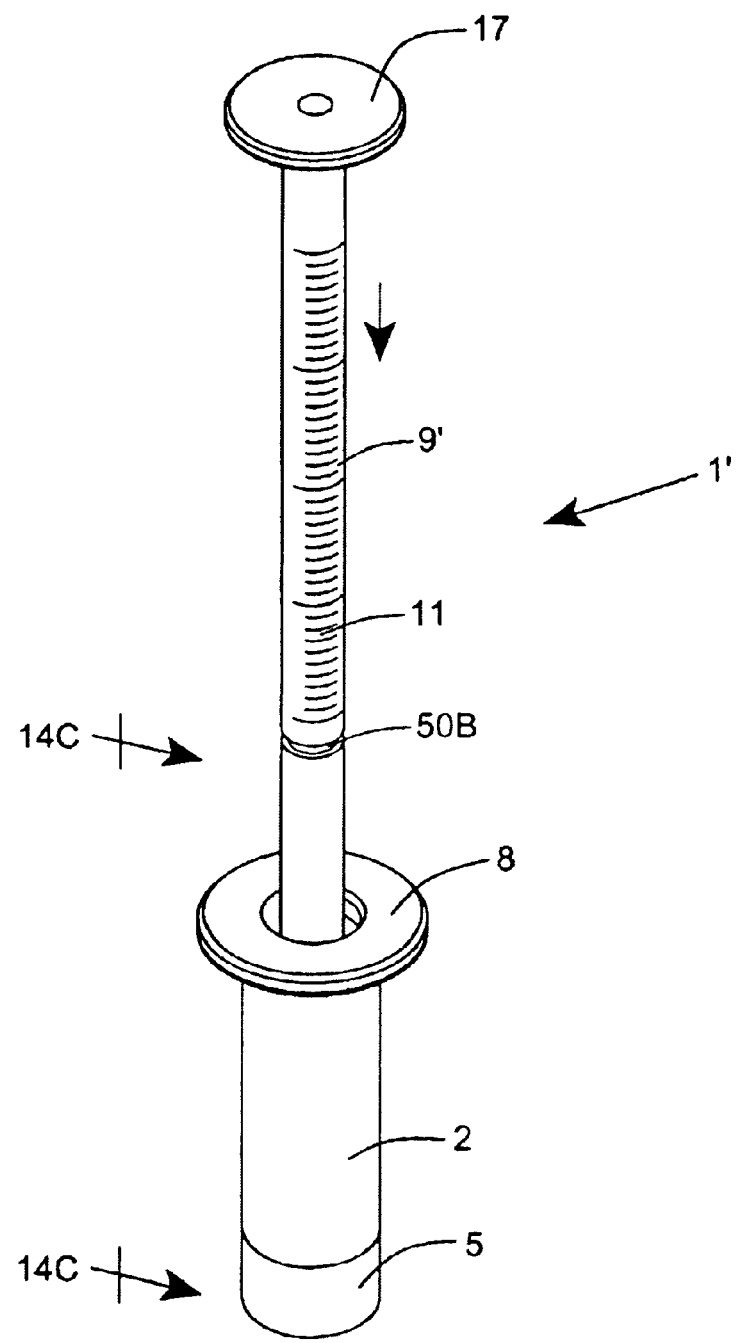
FIG. 14A is a perspective view of the ESR measurement instrument shown arranged in its Blood Collection Configuration with its blood collection tube partially filled with a diluted sample of whole anti-coagulated blood, its removable tube holder and retainer assembly shown removed from the sedimentation measurement tube and blood collection tube structures of the instrument, its air/fluid flow restriction plug removed from the top opening in the sedimentation measurement tube, and the sedimentation measurement tube just starting to be manually pushed slightly downward into the blood collection tube.
Figure 14B:
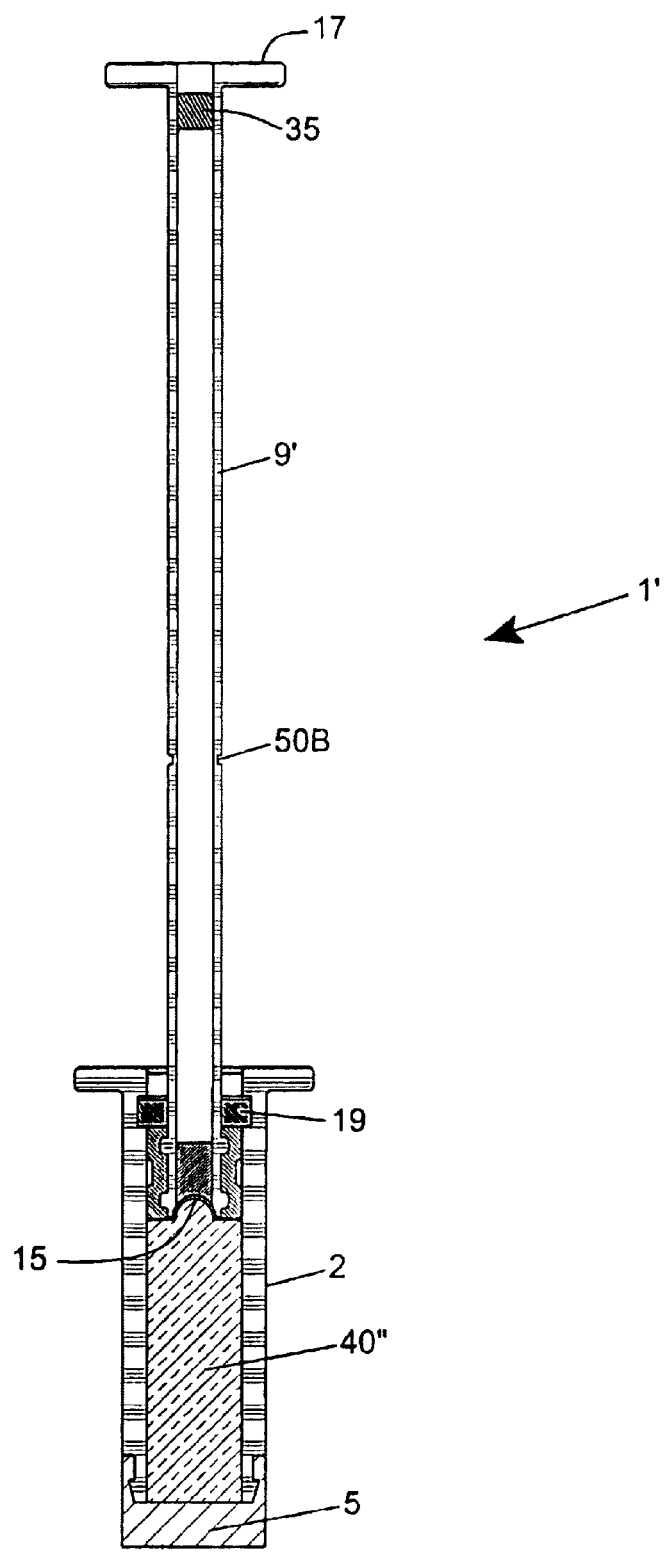
FIG. 14B is a cross-sectional view of the ESR measurement instrument illustrated in FIG. 14A, showing the membrane at the end of the rubber of the plunger being stretched and distorted under fluid pressure, prior to its rupture.
Figure 14C:
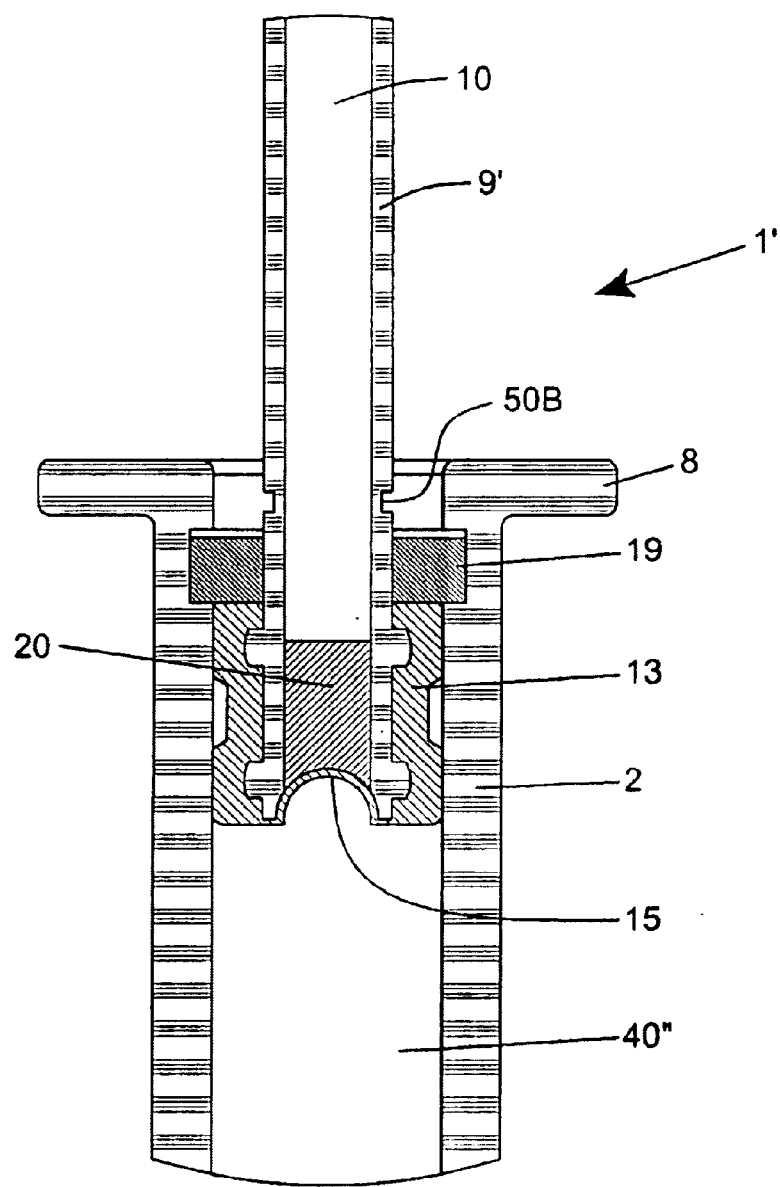
FIG. 14C is a partial enlarged view of the ESR measurement instrument taken along line 14C—14C in FIG. 14A.
Figure 15A:
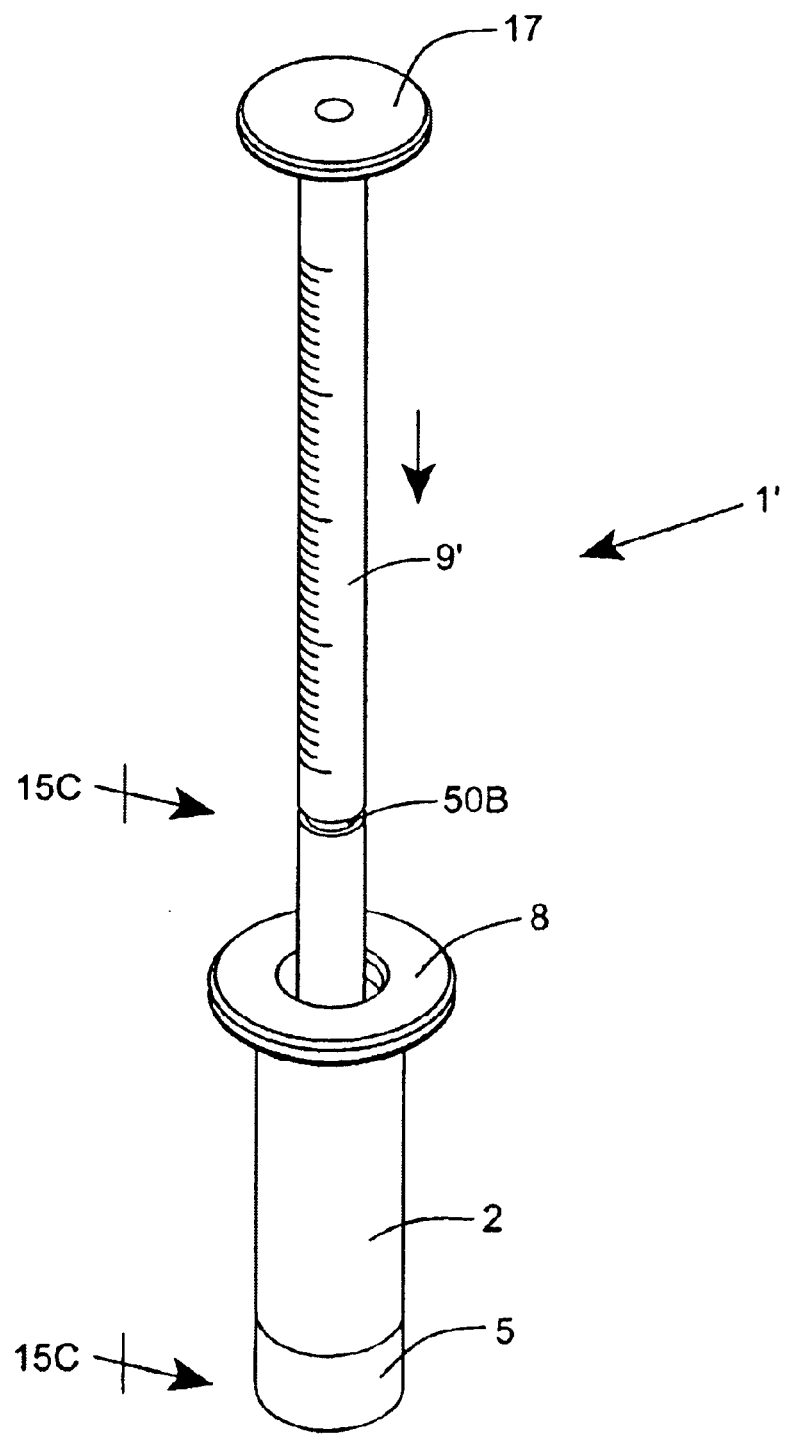
FIG. 15A is a perspective view of the ESR measurement instrument of the second illustrative embodiment shown arranged in its Blood Collection Configuration with its removable tube holder and retainer assembly shown removed from the sedimentation measurement tube and blood collection tube structures of the instrument, its air/fluid flow restriction plug removed from the top opening in the sedimentation measurement tube, and the sedimentation measurement tube being manually pushed downward into the blood collection tube, forcing blood to flow from the blood collection tube up into and along about halfway up the hollow interior volume of the sedimentation measurement tube, mixing with the blood diluting agent (e.g. physiologic NaCl solution or sodium citrate solution) contained therein.
Figure 15B:
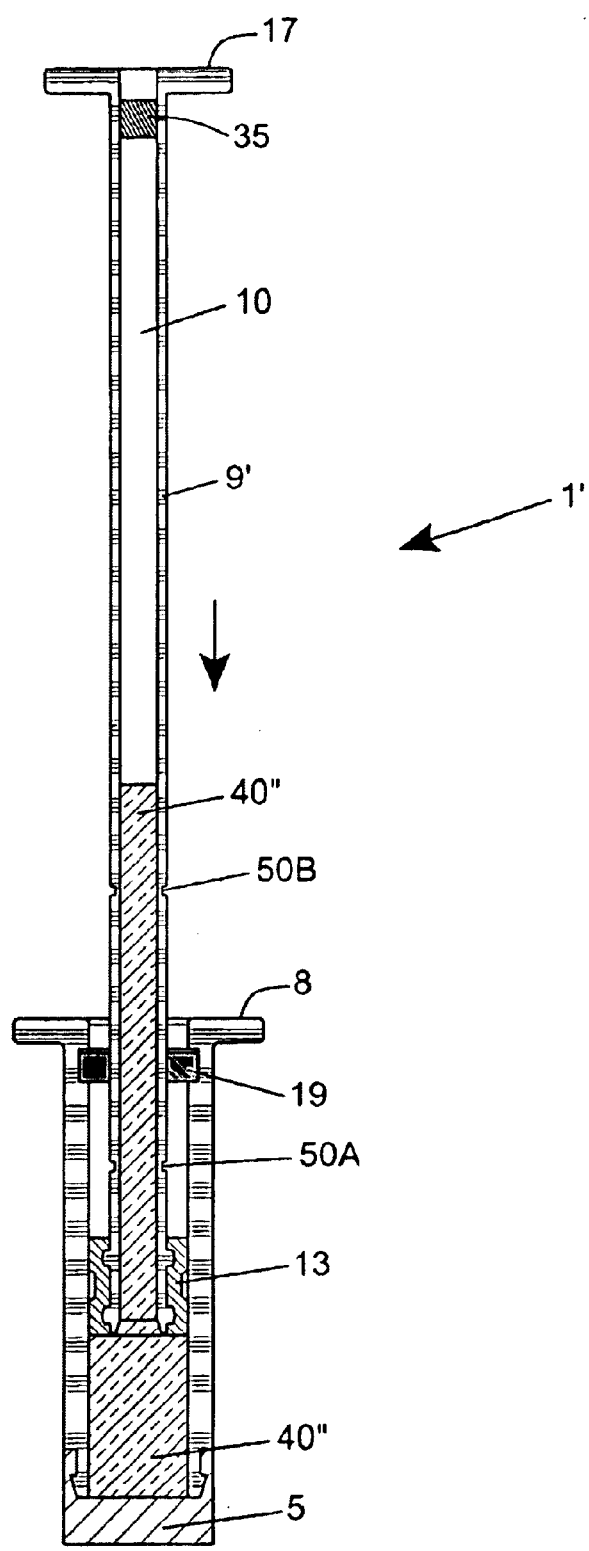
FIG. 15B is a cross-sectional view of the ESR measurement instrument illustrated in FIG. 15A, showing the membrane at the end of the rubber of the plunger ruptured and blood from the blood collection tube injected up about halfway along the interior volume of the sedimentation measurement tube.
Figure 15C:
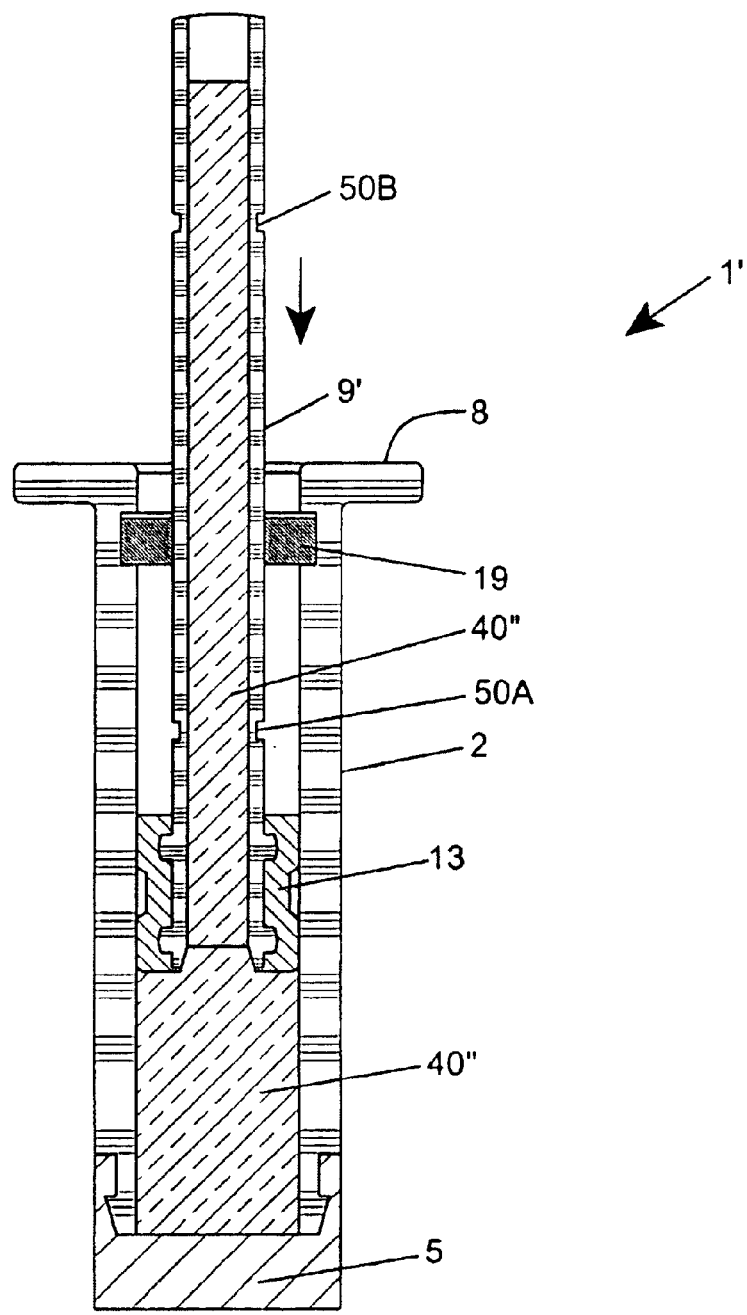
FIG. 15C is a partial enlarged view of the ESR measurement instrument taken along line 15C—15C in FIG. 15A.
Figure 16A:
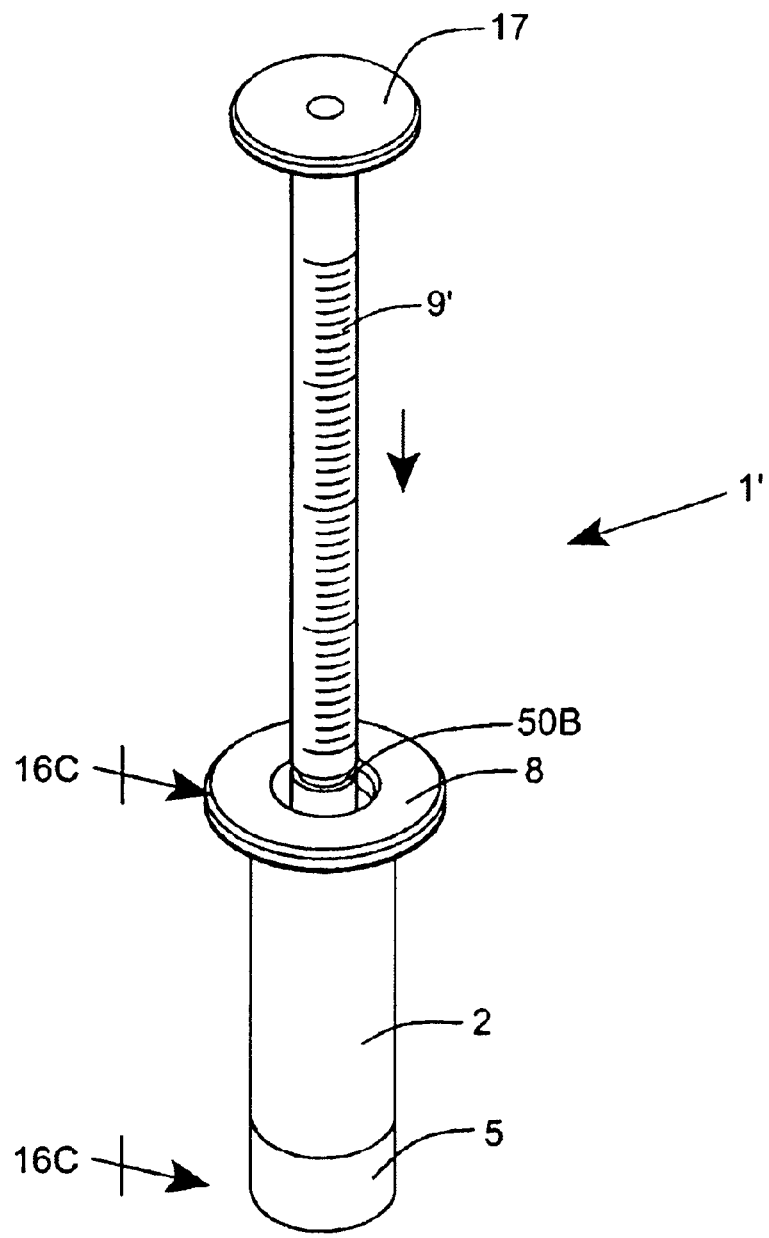
FIG. 16A is a perspective view of the ESR measurement instrument of the second illustrative embodiment shown arranged in its Blood Collection Configuration with its removable tube holder and retainer assembly shown removed from the sedimentation measurement tube and blood collection tube structures of the instrument, its air/fluid flow restriction plug removed from the top opening in the sedimentation measurement tube, and the sedimentation measurement tube being manually pushed downward to the bottom of the blood collection tube, causing the plunger's membrane to rupture under pressure, and blood to flow from the blood collection tube into and up along about the entire interior volume of the sedimentation measurement tube and mixing with the blood diluting agent contained therein.
Figure 16B:
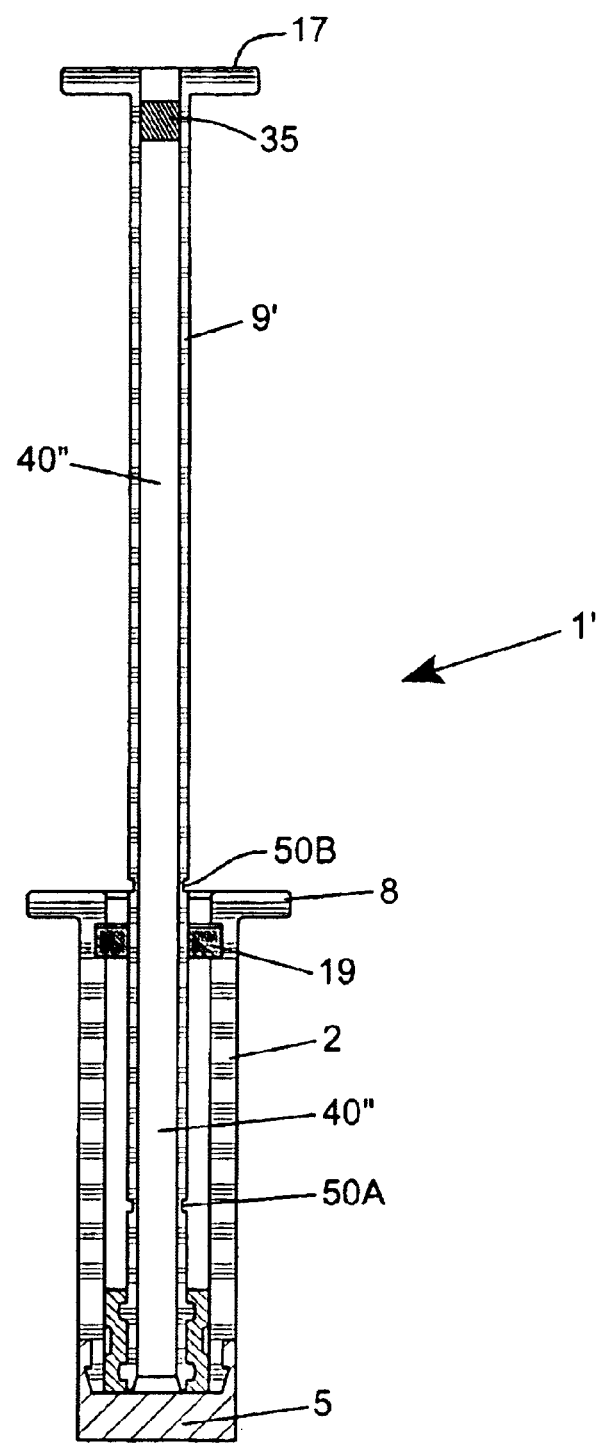
FIG. 16B is a cross-sectional view of the ESR measurement instrument illustrated in FIG. 16A, showing the membrane at the end of the rubber of the plunger ruptured and blood from the blood collection tube injected up along the entire length of the interior volume of the sedimentation measurement tube.
Figure 16C:
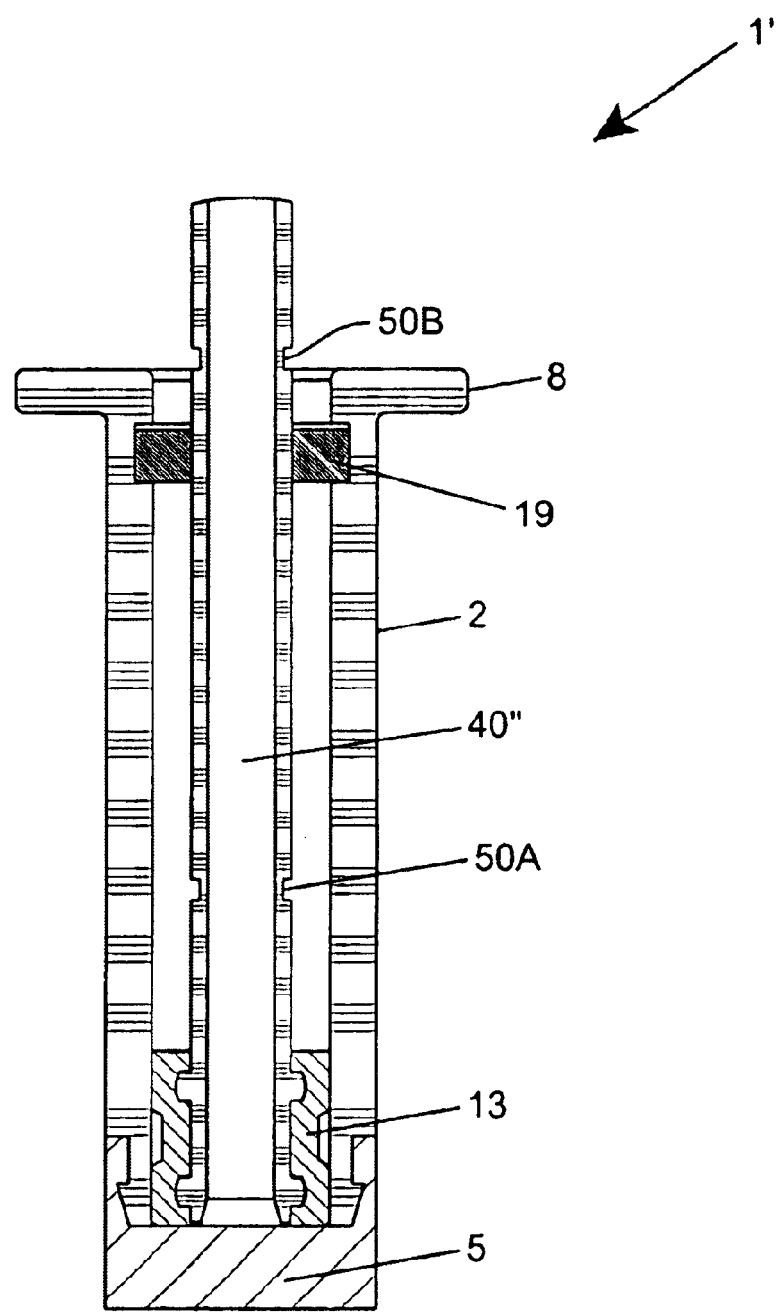
FIG. 16C is a partial enlarged view of the ESR measurement instrument taken along line 16C—16C in FIG. 16A.

As indicated at Block E in FIG. 10, the ESR measurement method involves the user (e.g. tester or clinician) manually grasping the ESR measurement instrument with the lower flange 8 positioned between the user's index and middle fingers, and the user's thumb positioned on the top (i.e. upper) flange 17 as when handling a conventional syringe. In this instrument handling arrangement, the user pushes the sedimentation measurement tube 9' down into the blood collection tube 2 using his or her thumb, just as when expressing liquid from a conventional syringe, as illustrated in FIGS. 13 through 15B. This action causes the rupturable membrane 15 to rupture, and forces the sample of anti-coagulated blood 40 in the blood collection tube 2 to rush up into the hollow interior volume of the sedimentation measurement tube 9', and mix with the blood diluting agent (e.g. physiologic NaCl solution or sodium citrate solution) contained therein. The process of the membrane 15 rupturing in response to the rubber plunger 13 being plunged into the blood collection tube 2 is schematically illustrated in FIG. 14C. As shown, during this process, the membrane 15 stretches as the hydrostatic pressure beneath its surface increases with increasing downward pressure, up until a point where the membrane material fails and ruptures, without compromising the overall structural integrity of the side wall portions of the rubber plunger component. As the sedimentation measurement tube 9' is plunged into the blood collection tube, the pressure of the blood sample therein increases, causing the anti-coagulated blood sample to flow through the ruptured membrane 15 and up along the hollow interior volume of the sedimentation measurement tube. At the same time, the rubber walls of the plunger 15 and gasket 19 create a high-quality liquid seal that prevents no amount of the collected blood sample to leak out from the combined contained volume created by the hollow interior volume of the sedimentation measurement tube being arranged in fluid communication with the hollow interior volume of the blood collection tube.

Figure 17A:
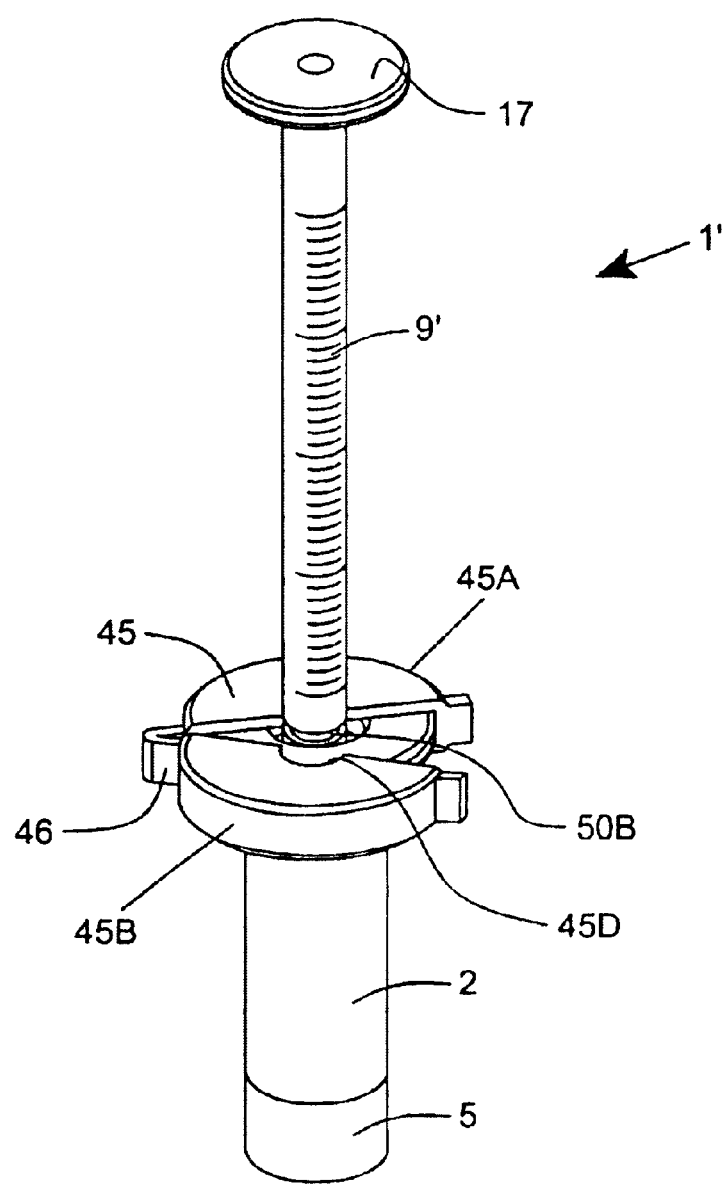
FIGS. 17A and 17B provide perspective views of the ESR measurement instrument of the second illustrative embodiment arranged in its ESR Measurement Configuration, with the removable tube holder and retainer assembly being reinstalled about the sedimentation measurement tube and blood collection tube structures so that these components may be locked securely together, prior to, during or after the reading of the ESR measurement along the sedimentation measurement tube, while preventing the spillage of collected blood contained within the blood collection container during and after ESR measurements have been taken.
Figure 17B:
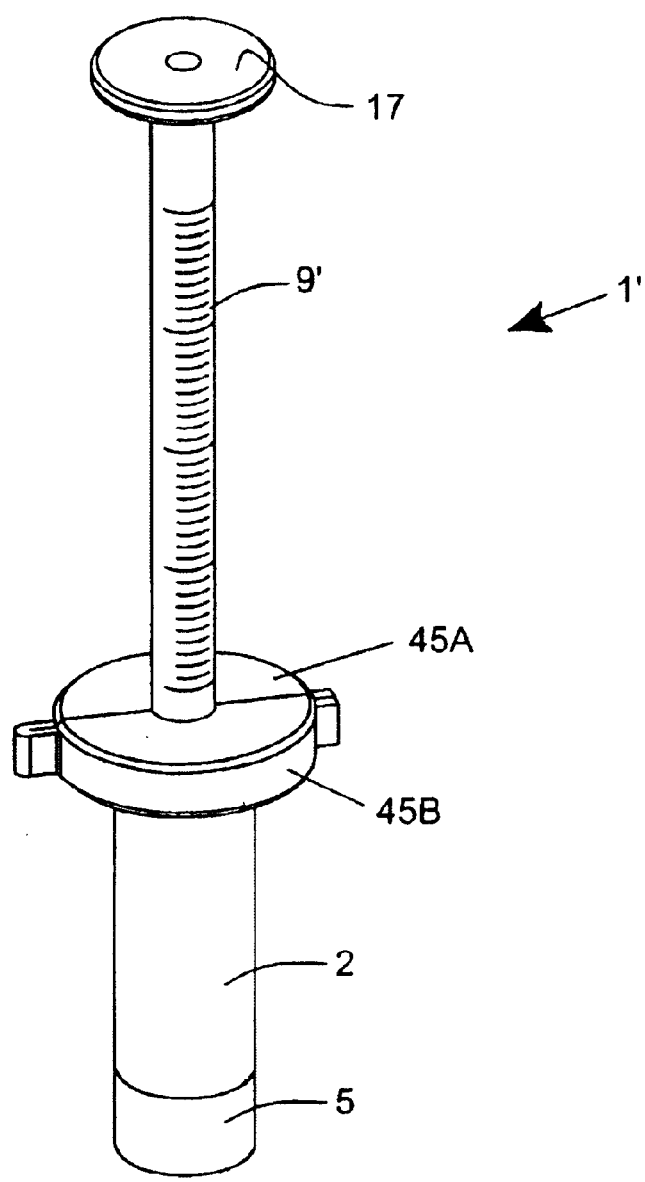

Thereafter, the cover halves 45, 45 are reattached about the bottom flange 8, as shown in FIG. 17A, and then the cover halves are snapped permanently closed as shown in FIG. 17B. When reattached, as shown, portion 45D of the cover halves 45A, 45B fit snugly into recess 50B formed on sedimentation measurement tube 9', securely locking sedimentation measurement tube 9' within the blood collection tube 2. In this final state of configuration, the whole anti-coagulated blood sample contained in the ESR measurement instrument is thoroughly mixed with the blood diluting agent (e.g. physiologic NaCl solution or sodium citrate solution) 20, and the blood plasma/erythrocyte cell (P/E) interface level begins to settle within the vertically-supported sedimentation measurement tube under the influence of gravitational forces. At the same time, the diluted anti-coagulated whole blood sample is safely sealed (i.e. entombed) within locked instrument. To perform ESR measurement in accordance with the Westergren or like method, the ESR measurement instrument is positioned upright, for example, inserted in a perfectly vertical support stand having a support aperture and bubble-level (e.g., located on a table, lab bench, or other stable surface) for a time period of about 60 minutes. At the end of this time period, an accurate ESR measurement ready can be read by measuring how far the plasma/erythrocyte (P/E) interface level has settled in millimeters under the influence of gravity after sixty minutes, i.e. measured in [mm/hr] against the calibrated graduations 11 formed along the length of the sedimentation measurement tube.

After the ESR measurement is taken (i.e. by reading the P/E interface level location) against the calibrated graduations 11 along the sedimentation measurement tube, and recorded in the patient's medical record, the locked ESR measurement instrument can be safely discarded as medical waste according to government regulations and/or safety standards.

As the collected blood sample is always contained within the instrument during the ESR measurement method of the present invention, there is little if any risk to the technician performing the ESR measurement using the ESR measurement instrument of the present invention. Also, as the instrument is essentially locked, the risk of leakage or environmental contamination is substantially minimized.

Figure 18A:
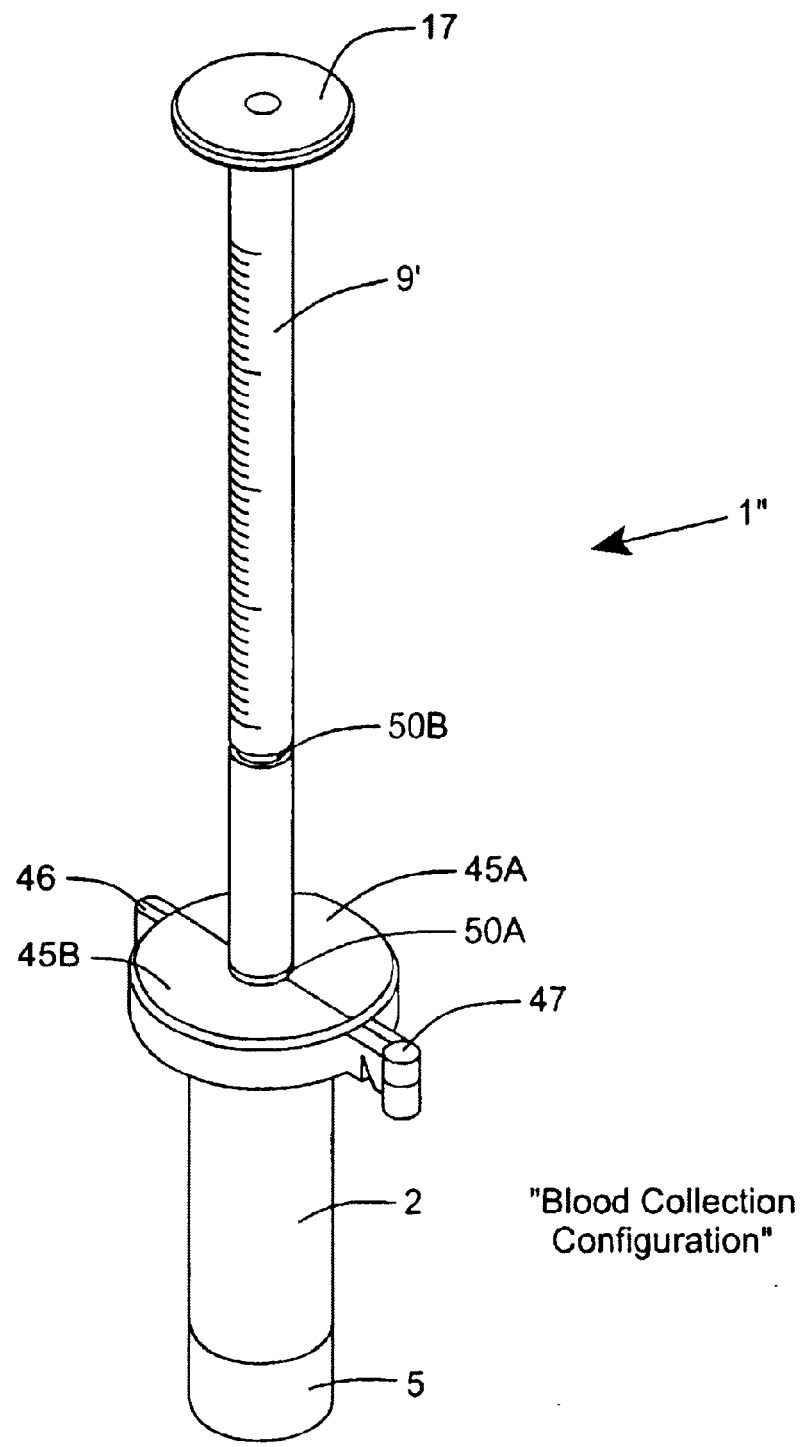
FIG. 18A is a first perspective view of the disposable ESR measurement instrument of the third illustrative embodiment, shown arranged in its Blood Collection Configuration, wherein the plunger portion of the empty sedimentation measurement tube is inserted within the upper portion of the blood collection tube, and held in a stationary position with respect to the blood collection tube by way of a removable tube holder and restraint assembly, so as to not break the liquid seal created within the pressurized blood collection tube containing (i) a small quantity of anti-coagulant (i.e. K3EDTA) for preventing a whole blood sample contained therein from coagulation after collection, as well as (ii) a predetermined quantity of dilutent (e.g. physiologic NaCl solution or sodium citrate solution) for diluting the sample of whole blood prior to ESR testing.
Figure 18B:
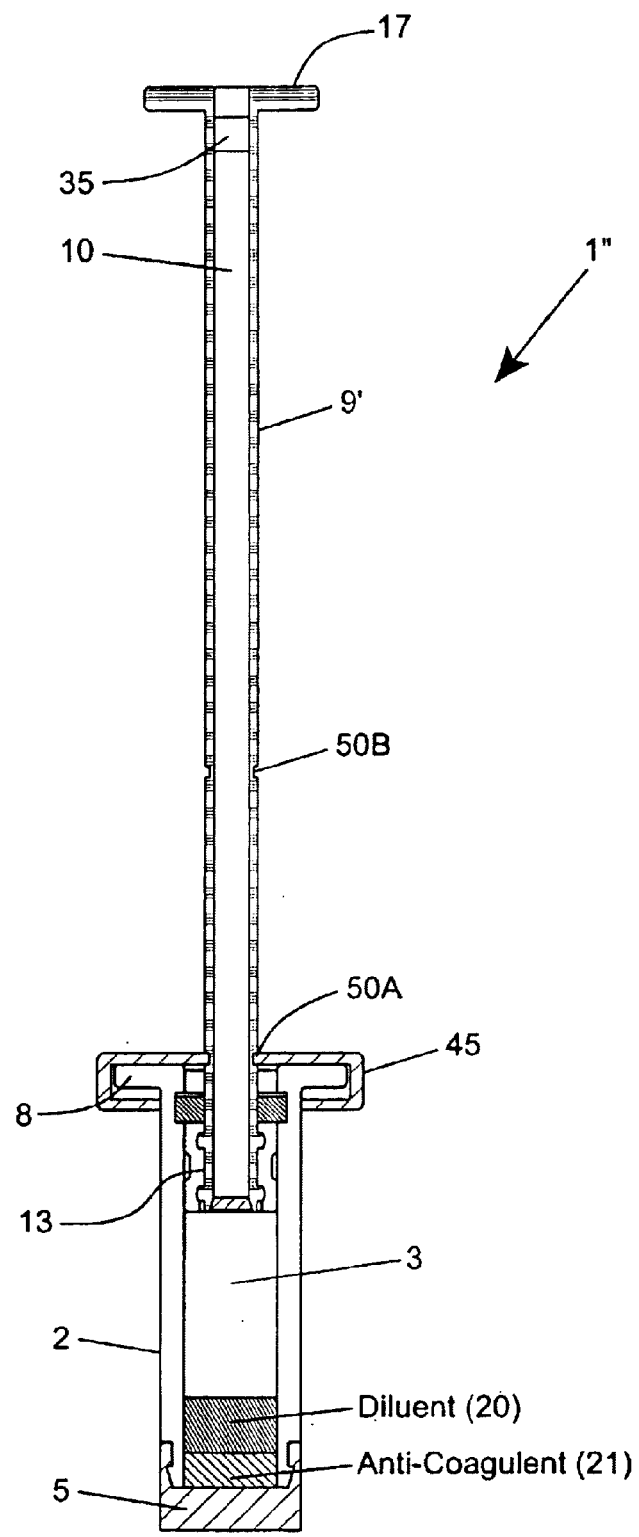
FIG. 18B is a cross-sectional view of the disposable ESR measurement instrument of the third illustrative embodiment taken along line 18B—18B of FIG. 18A, wherein the plunger portion of the sedimentation measurement tube is inserted within the upper portion of the blood collection tube and held in a stationary position with respect to the pressurized blood collection tube by way of the tube holder and restraint assembly, so as to not break the liquid seal created within the blood collection tube while the instrument is arranged in its Blood Collection Configuration.

Third Illustrative Embodiment of the ESR Measurement Instrument of the Present Invention In FIGS. 18A and 18B, the ESR test measurement instrument of the third illustrative embodiment is shown arranged in its Blood Collection Configuration. In this illustrative embodiment, the plunger portion of the sedimentation measurement tube is inserted within the upper portion of the blood collection tube, and held in a stationary position with respect to the blood collection tube by way of a removable tube holder and restraint assembly, and is constructed and assembled exactly the same way as in the second illustrative embodiment shown in FIGS. 12A1 through 17B. However, in this alternative ESR measurement instrument design, the pressurized blood collection tube employed therein contains both (i) a small quantity of anti-coagulant (i.e. K3EDTA) for preventing a whole blood sample contained therein from coagulation after collection, and (ii) a volume of blood diluting agent (e.g. physiologic NaCl solution or sodium citrate solution) for diluting the sample of whole blood prior to ESR testing. Preferably, this ESR measuring instrument is used to carry out the Westergren or like ESR methodology described hereinabove, wherein dilution of a collected sample of anti-coagulated whole blood occurs prior to ESR measurement.

Figure 19A:
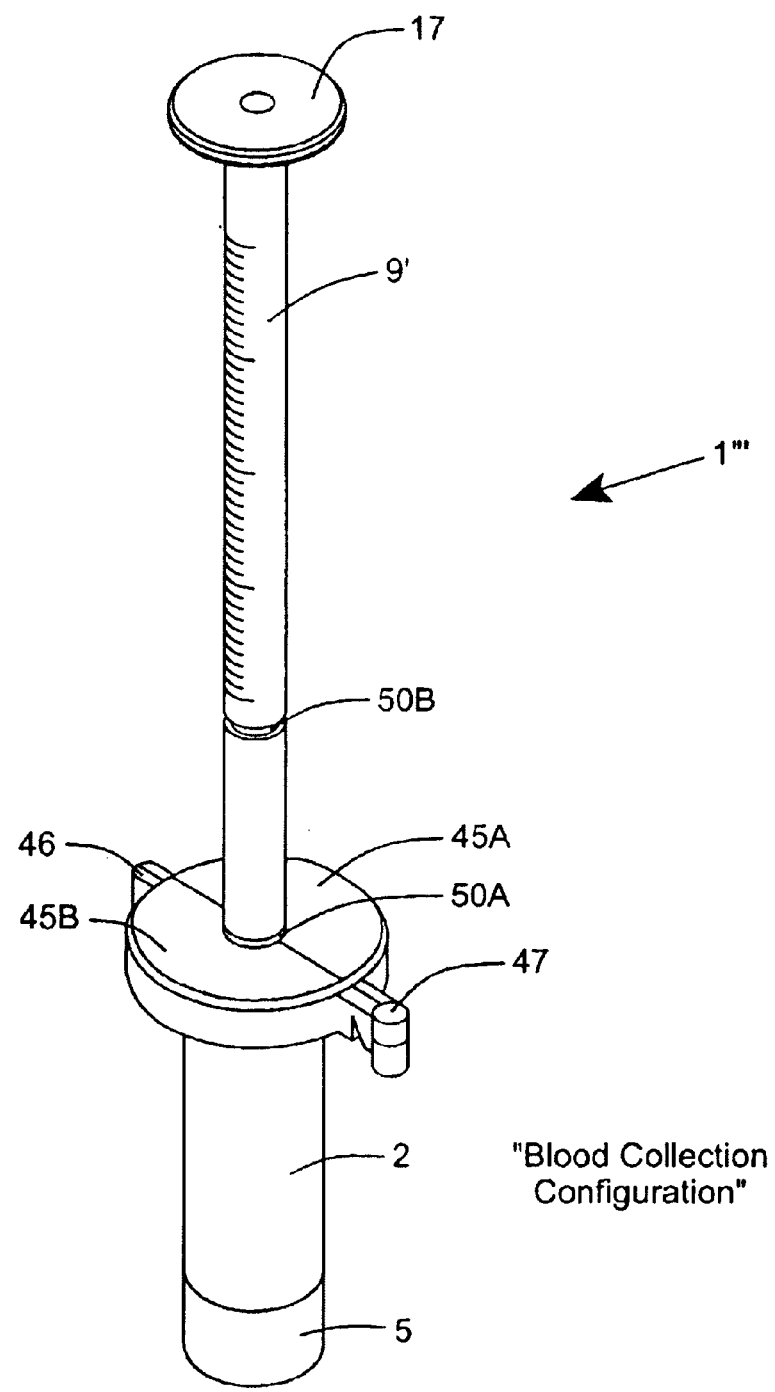
FIG. 19A is a first perspective view of the disposable ESR measurement instrument of the fourth illustrative embodiment, shown arranged in its Blood Collection Configuration, wherein the plunger portion of the empty sedimentation measurement tube is inserted within the upper portion of the blood collection tube, and held in a stationary position with respect to the blood collection tube by way of a removable tube holder and restraint assembly, so as to not break the liquid seal created within the pressurized blood collection tube containing only a small quantity of anti-coagulant (i.e. K3EDTA) for preventing the non-diluted whole blood sample contained therein from coagulation after collection.
Figure 19B:
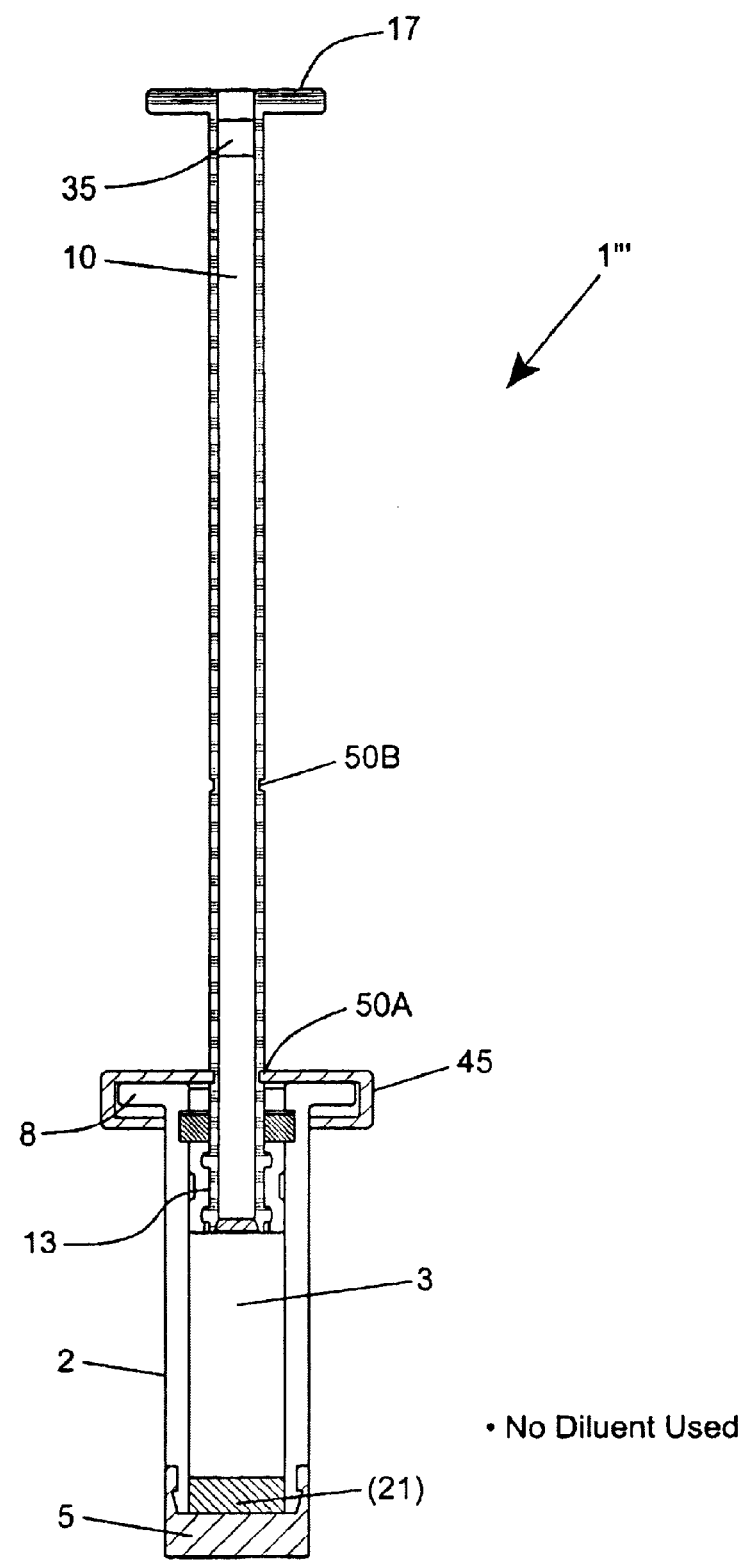
FIG. 19B is a cross-sectional view of the ESR measurement instrument of the fourth illustrative embodiment taken along line 19B—19B of FIG. 19A, wherein the plunger portion of the sedimentation measurement tube is inserted within the upper portion of the blood collection tube and held in a stationary position with respect to the pressurized blood collection tube by way of the tube holder and restraint assembly, so as to not break the liquid seal created within the blood collection tube while the instrument is arranged in its Blood Collection Configuration.

Fourth Illustrative Embodiment of the ESR Measurement Instrument of the Present Invention In FIGS. 19A and 19B, a first perspective view of the ESR test measurement instrument of the fourth illustrative embodiment is shown arranged in its Blood Collection Configuration. In this illustrative embodiment, the plunger portion of the sedimentation measurement tube is inserted within the upper portion of the blood collection tube, and held in a stationary position with respect to the blood collection tube by way of a removable tube holder and restraint assembly, and is constructed and assembled exactly the same way as in the second illustrative embodiment as shown in FIGS. 12A1 through 17B. However, in this alternative ESR measurement instrument design, the pressurized blood collection tube employed therein contains only a small quantity of anti-coagulant (i.e. K3EDTA) for preventing a whole blood sample contained therein from coagulation after collection, and the air/fluid flow sealed sedimentation measurement tube does not contain any amount of blood diluting agent (e.g. physiologic NaCl solution or sodium citrate solution) for diluting the sample of whole blood prior to ESR testing. Preferably, this ESR measuring instrument is used to carry out the Wintrobe or like ESR methodology, wherein unlike the Westergren ESR method, dilution of a collected sample of anti-coagulated whole blood does not occur prior to ESR measurement.

Instrument Design and Implementation Considerations

When designing and implementing any of the illustrative embodiments of the ESR test measurement instrument of the present invention described above, it is understood that the actual physical dimensions of the blood collection tube and the sedimentation measurement tube will depend on several factors, including: (1) the actual amount of the whole blood sample to be collected and treated by the instrument during ESR testing; and (2) the particular type and variation of the ESR testing method (e.g. Westergren, Wintrobe, etc.) to be carried out using the ESR measurement instrument.

In applications where large whole blood samples can be collected (e.g. as with adult patients), the blood collection tube can be designed to contain a standard volume (e.g. 1.0 ml) of collected whole blood and a negligible amount of K3EDTA anti-coagulating agent, whereas the sedimentation measurement tube can be designed to contain this same amount of anti-coagulated blood in addition to a blood diluting agent (e.g. physiologic NaCl solution or sodium citrate solution) mixed in the standard ratio of 1 part blood dilutent to 4 parts of anti-coagulated blood. Preferably, the final form factor of the disposable ESR test measurement instrument design will resemble a slightly-elongated syringe-like instrument. The final ESR measurement instrument design should be calibrated against the standard Westergren ESR test method and apparatus kit, as published by NCCLS, in the document entitled "Reference and Selected Procedure For The Erythrocyte Sedimentation Rate (ESR) Test; Approved Standard—Fourth Edition", (NCCLA Publication No. H2-A4), supra.

In applications where only small whole blood samples can be collected (e.g. as with infants and younger children), the blood collection tube can be designed to contain a smaller volume (e.g. 0.5 ml) of collected whole blood and a negligible amount of K3EDTA anti-coagulating agent, whereas the sedimentation measurement tube can be designed to contain this same amount of anti-coagulated blood in addition to a blood diluting agent (e.g. physiologic NaCl solution or sodium citrate solution) mixed in the standard ratio of 1 part blood dilutent to 4 parts of anti-coagulated blood. Preferably, the final form factor of the disposable ESR measurement instrument design will resemble a slightly-elongated syringe instrument. The final ESR measurement instrument design should be calibrated against the standard Westergren ESR test method and apparatus kit, as published in "Reference and Selected Procedure For The Erythrocyte Sedimentation Rate (ESR) Test; Approved Standard—Fourth Edition", supra, so that test results from the ESR test measurement instrument of the present invention are strong correlated with test results obtained from the standard Westergren ESR test method.

Modifications Which Come to Mind

While each embodiment of the disposable ESR test measurement instrument disclosed hereinabove has employed a rubber plunger element having a rupturable membrane, it is understood that in other embodiments of the present invention, the rupturable membrane may be realized using a blow-out type of plug or element which, in response to sufficient blood sample pressure, blows out permitting the blood sample to fill up the sedimentation measurement tube as the instrument is arranged in its ESR Measurement Configuration. Preferably, this blow-out type plug or element is hingedly connected to the walls of the rubber plunger so as to not interfere with the ESR test measurement. Clearly, other ways and means can be used to create this pressure-sensitive blood flow valve structure arranged between the hollow interior volume of the sedimentation measurement tube and the hollow interior volume of the blood collection tube of the instrument, in accordance with the general spirit of the present invention.

It is understood that the ESR instruments of the illustrative embodiments may be modified in a variety of ways which will become readily apparent to those skilled in the art, and having the benefit of the novel teachings disclosed herein. All such modifications and variations of the illustrative embodiments thereof shall be deemed to be within the scope and spirit of the present invention as defined by the accompanying claims to Invention.

What is claimed is:

1. An erythrocyte sedimentation rate (ESR) measurement instrument having a Blood Collection Configuration and an ESR Measurement Configuration, said ESR measurement instrument comprising:

a sedimentation measurement tube having a hollow interior volume containing a predetermined quantity of blood sample diluting agent therewithin and being air/fluid sealed with respect to the ambient environment; and a blood collection tube having a hollow interior cylindrical volume with predetermined internal diameter for receiving a sample of whole human blood during blood collection operations, and containing a predetermined quantity of anti-coagulant and being vacuum-sealed with respect to the ambient environment, and physically coupled to said air-sealed sedimentation measurement tube, by at least a portion of said sedimentation measurement tube being inserted within a portion of the hollow interior volume of said blood collection tube;

wherein said sedimentation measurement tube and said blood collection tube are maintained stationarily fixed relative to each other as a unitary assembly having a syringe-like form factor when said ESR measurement instrument is arranged in said Blood Collection Configuration, during which a needle-supporting connector is connected to said blood collection tube and a sample of whole blood from a patient vacuum-drawn and injected into said blood collection tube;

wherein said blood collection tube has (i) a pair of low-relief flanges projecting about an outer end surface of the the blood collection tube for gripping a rubber needle-pierceable cap with a thick self-sealing end portion and thinner wall portions that snap fit over the low-relief flanges and the outer end surface of the blood collection tube during assembly, and (ii) a large annular flange projecting from the outer end of the blood collection tube at an end opposite the low-relief flanges, for engagement with the fingers of a person pushing said sedimentation measurement tube within the blood collection tube with his or her thumb; and wherein after the sample of anti-coagulated blood has been collected in said blood collection tube and the needle-supporting connector is disconnected therefrom, the air/fluid seal of said sedimentation measurement tube is broken and then said sedimentation measurement tube is manually plunged into and to the bottom of the hollow interior volume of said blood collection tube, using a single handed operation, so as to rearrange said ESR measurement instrument into said ESR Measurement Configuration, whereby the anti-coagulated sample of blood fills up a substantial portion of said sedimentation measurement tube and mixes with said blood sample diluting agent to enable a blood plasma/erythrocyte cell (P/E) interface level within said sedimentation measurement tube to settle downwards toward said blood collection tube during a predetermined time period when said ESR measurement instrument is oriented in a gravity vertical position, so that the erythrocyte sedimentation rate (ESR) of said collected blood sample is measured by determining how far said P/E interface level has moved against graduation markings formed along the length of said sedimentation measurement tube during said predetermined time period.

2. The ESR measurement instrument of claim 1, wherein said sedimentation measurement tube has (i) a hollow central bore of a predetermined diameter and an outer diameter slightly smaller than the internal diameter of the hollow interior volume of the blood collection tube, (ii) a said series of graduation marks formed along an exterior surface of the sedimentation measurement tube for indicating the ESR of a whole blood sample, (iii) a plurality of low-relief plunger gripping flanges projecting from the end of the sedimentation measurement tube that is inserted into the blood collection tube, wherein said low-relief plunger gripping flanges retain a rubber plunger, wherein said rubber plunger has a hollow inner volume bounded on one end by a thin, rupturable wall membrane, and having outer wall surfaces which slide over the end of said sedimentation measurement tube and engage the flanges projecting therefrom.

3. The ESR measurement instrument of claim 2, wherein a rubber washer is placed over the plunger gripping flanges, before the rubber plunger is attached to the end of the sedimentation measurement tube, for creating a liquid seal between outer walls of said sedimentation measurement tube and inner walls of said blood collection tube.

4. An erythrocyte sedimentation rate (ESR) measurement instrument having a Blood Collection Configuration and an ESR Measurement Configuration, said ESR measurement instrument comprising:

a sedimentation measurement tube having a hollow interior volume containing a predetermined quantity of blood sample diluting agent therewithin and being air/fluid sealed with respect to the ambient environment; and a blood collection tube having a hollow interior volume containing a predetermined quantity of anti-coagulant and being vacuum-sealed with respect to the ambient environment, and physically coupled to said air-sealed sedimentation measurement tube, by at least a portion of said sedimentation measurement tube being inserted within a portion of the hollow interior volume of said blood collection tube;

wherein said sedimentation measurement tube and said blood collection tube are maintained stationarily fixed relative to each other as a unitary assembly having a syringe-like form factor when said ESR measurement instrument is arranged in said Blood Collection Configuration, during which a needle-supporting connector is connected to said blood collection tube and a sample of whole blood from a patient is vacuum-drawn and injected into said blood collection tube;

wherein said sedimentation measurement tube has (i) a hollow central bore of a predetermined diameter and an outer diameter slightly smaller than an internal diameter of the hollow interior volume of the blood collection tube, (ii) a series of graduation marks formed along an exterior surface of the sedimentation measurement tube for indicating the ESR of a whole blood sample, and (iii) a plurality of low-relief plunger gripping flanges projecting from the end of the sedimentation measurement tube that is inserted into the blood collection tube, wherein said low-relief plunger gripping flanges retain a rubber plunger, wherein said rubber plunger has a hollow inner volume bounded on one end by a thin, rupturable wall membrane, and having outer wall surfaces which slide over the end of said sedimentation measurement tube and engage the flanges projecting therefrom;

wherein said sedimentation measurement tube has a large annular flange projecting from its outer end at the end opposite the rubber plunger, for engagement with the thumb of a person pushing the sedimentation measurement tube within the blood collection tube when rearranging the ESR measurement instrument into said ESR Measurement Configuration; and wherein after the sample of anti-coagulated blood has been collected in said blood collection tube and the needle-supporting connector is disconnected therefrom, the air/fluid seal of said sedimentation measurement tube is broken and then said sedimentation measurement tube is manually plunged into and to the bottom of the hollow interior volume of said blood collection tube, using a single handed operation, so as to rearrange said ESR measurement instrument into said ESR Measurement Configuration, whereby the anti-coagulated sample of blood fills up a substantial portion of said sedimentation measurement tube and mixes with said blood sample diluting agent to enable a blood plasma/erythrocyte cell (P/E) interface level within said sedimentation measurement tube to settle downwards toward said blood collection tube during a predetermined time period when said ESR measurement instrument is oriented in a gravity vertical position, so that the erythrocyte sedimentation rate (ESR) of said collected blood sample is measured by determining how far said P/E interface level has moved against the graduation markings formed along the length of said sedimentation measurement tube during said predetermined time period.

5. The ESR measurement instrument of claim 4, wherein an air/fluid flow restriction plug is insertable into a top end portion of said sedimentation measurement tube so as to restrict or occlude the flow of air from the ambient environment into the hollow interior volume of the sedimentation measurement tube the ESR measurement instrument is arranged in said Blood Collection Configuration.

6. An erythrocyte sedimentation rate (ESR) measurement instrument having a Blood Collection Configuration and an ESR Measurement Configuration, said ESR measurement instrument comprising:

a sedimentation measurement tube having an hollow interior volume; and a blood collection tube having a hollow interior cylindrical volume with a predetermined internal diameter for receiving a sample of whole human blood during blood collection operation, and containing a predetermined quantity of anti-coagulant and a predetermined quantity of blood sample diluting agent therewithin, and physically coupled to said sedimentation measurement tube by at least a portion of said sedimentation measurement tube being inserted within a portion of the hollow interior volume of said blood collection tube;

wherein said sedimentation measurement tube and said blood collection tube are maintained stationarily fixed relative to each other as a unitary assembly having a syringe-like form factor when said ESR measurement instrument is arranged in said Blood Collection Configuration, during which a needle-supporting connector is connected to said blood collection tube and a sample of whole blood from a patient is vacuum-drawn and injected into said blood collection tube;

wherein said blood collection tube has (i) a pair of low-relief flanges projecting about an outer end surface of the blood collection tube for gripping a rubber needle-pierceable cap with a thick self-sealing end portion and thinner wall portions that snap fit over the low-relief flanges and the outer end surface of the blood collection tube during assembly, and (ii) a large annular flange projecting from an outer end of the blood collection tube at an end opposite the low-relief flanges, for engagement with the fingers of a person pushing said sedimentation measurement tube within the blood collection tube with his or her thumb; and wherein after the sample of whole blood has been collected in said blood collection tube and mixes with said anti-coagulating agent and said predetermined quantity of blood sample diluting agent, the needle-supporting connector is disconnected therefrom, and said sedimentation measurement tube is manually plunged into and to the bottom of the hollow interior volume of said blood collection tube, using a single handed operation, so as to rearrange said ESR measurement instrument into said ESR Measurement on Configuration, whereby the anti-coagulated sample of blood fills up a substantial portion of said sedimentation measurement tube to enable a blood plasma/erythrocyte cell (P/E) interface level within said sedimentation measurement tube to settle downwards toward said blood collection tube during a predetermined time period when said ESR measurement instrument is oriented in a gravity vertical position, so that the erythrocyte sedimentation rate (ESR) of said collected blood sample is measured by determining how far said P/E interface level has moved against graduation markings formed along the length of said sedimentation measurement tube during said predetermined time period.

7. The ESR measurement instrument of claim 6, wherein said sedimentation measurement tube has (i) a hollow central bore of a predetermined diameter and an outer diameter slightly smaller than the internal diameter of the hollow interior volume of the blood collection tube, (ii) said series of graduation marks formed along the exterior surface of the sedimentation measurement tube for indicating the ESR of a whole blood sample, and (iii) a plurality of low-relief plunger gripping flanges projecting from the end of the sedimentation measurement tube that is inserted into the blood collection tube, wherein said low-relief plunger gripping flanges retain a rubber plunger, wherein said rubber plunger has a hollow inner volume bounded on one end by a thin, rupturable wall membrane, and having outer wall surfaces which slide over the end of said sedimentation measurement tube and engage the flanges projecting therefrom.

8. The ESR measurement instrument of claim 7, wherein said sedimentation measurement tube has a large annular flange projecting from its outer end at the end opposite the rubber plunger, for engagement with the thumb of a person pushing the sedimentation measurement tube within the blood collection tube when rearranging the ESR measurement instrument into its ESR Measurement Configuration.

9. The ESR measurement instrument of claim 7, wherein a rubber washer is placed over the plunger gripping flanges, before the rubber plunger is attached to the end of the sedimentation measurement tube, for creating a liquid seal between outer walls of the sedimentation measurement tube and inner walls of blood collection tube.

10. The ESR measurement instrument of claim 6, wherein a tube holder and restraint assembly is provided for holding the portion of the sedimentation measurement tube that is inserted within the portion of the blood collection tube, and maintaining these tubes in a stationary position with respect to each other while the ESR measurement instrument is arranged in said Blood Collection Configuration.

11. An erythrocyte sedimentation rate (ESR) measurement instrument having a Blood Collection Configuration and an ESR Measurement Configuration, said ESR measurement instrument comprising:

a sedimentation measurement tube having a hollow interior cylindrical volume; and a blood collection tube having a hollow interior volume with a predetermined internal diameter for receiving a sample of whole blood during blood collection operations, and containing a predetermined quantity of anti-coagulating agent and bein vacuum-sealed with respect to the ambient environment, and physically coupled to said sedimentation measurement tube, by at least a portion of said sedimentation measurement tube being inserted within a portion of the hollow interior volume of said blood collection tube;

wherein said sedimentation measurement tube and said blood collection tube are maintained stationarily fixed relative to each other as a unitary assembly having a syringe-like form factor when said ESR measurement instrument is arranged in said Blood Collection Configuration, during which a needle-supporting connector is connected to said blood collection tube and a sample of whole blood from a patient is vacuum-drawn and injected into said blood collection tube;

wherein said blood collection tube has (i) a pair of low-relief flanges projecting about an outer end surface of the blood collection tube for gripping a rubber needle-pierceable cap with a thick self-sealing end portion and thinner wall portions that snap fit over the low-relief flanges and the outer end surface of the blood collection tube during assembly, and (ii) a large annular flange projecting from an outer end of the blood collection tube at an end opposite the low-relief flanges, for engagement with the fingers of a person pushing said sedimentation measurement tube within the blood collection tube with his or her thumb; and wherein after the sample of anti-coagulated blood has been collected in said blood collection tube and the needle-supporting connector is disconnected therefrom, said sedimentation measurement tube is manually plunged into and to the bottom of the hollow interior volume of said blood collection tube, using a single handed operation, so as to rearrange said ESR measurement instrument into said ESR Measurement Configuration, whereby the anti-coagulated sample of blood fills up a substantial portion of said sedimentation measurement tube to enable a blood plasma/erythrocyte cell (P/E) interface level within said sedimentation measurement tube to settle downwards toward said blood collection tube during a predetermined time period when said ESR measurement instrument is oriented in a gravity vertical position, so that the erythrocyte sedimentation rate (ESR) of said collected blood sample is measured by determining how far said P/E interface level has moved against graduation markings formed along the length of said sedimentation measurement tube during said predetermined time period.

12. The ESR measurement instrument of claim 11, wherein said sedimentation measurement tube has (i) a hollow central bore of a predetermined diameter and an outer diameter slightly smaller than the internal diameter of the hollow interior volume of the blood collection tube, (ii) said series of graduation marks formed along an exterior surface of the sedimentation measurement tube for indicating the ESR of a whole blood sample, and (iii) a plurality of low-relief plunger gripping flanges projecting from the end of the sedimentation measurement tube that is inserted into the blood collection tube, wherein said low-relief plunger gripping flanges retain a rubber plunger, wherein said rubber plunger has a hollow inner volume bounded on one end by a thin, rupturable wall membrane, and having outer wall surfaces which slide over the end of said sedimentation measurement tube and engage the flanges projecting therefrom.

13. The ESR measurement instrument of claim 12, wherein said sedimentation measurement tube has a large annular flange projecting from its outer end at the end opposite the rubber plunger, for engagement with the thumb of a person pushing the sedimentation measurement tube within the blood collection tube when rearranging said ESR measurement instrument into its ESR Measurement Configuration.

14. The ESR measurement instrument of claim 12, wherein a rubber washer is placed over the plunger gripping flanges, before the rubber plunger is attached to the end of the sedimentation measurement tube, for creating a liquid seal between outer walls of said sedimentation measurement tube and inner walls of said blood collection tube.

15. The ESR measurement instrument of claim 11, wherein a tube holder and restraint assembly is provided for holding the portion of the sedimentation measurement tube that is inserted within the portion of the blood collection tube, and maintaining these tubes in a stationary position with respect to each other while the ESR measurement instrument is arranged in said Blood Collection Configuration.

* * * * *